US008273704B2

(12) United States Patent
Kumar

(10) Patent No.: US 8,273,704 B2
(45) Date of Patent: *Sep. 25, 2012

(54) USE OF REPEAT SEQUENCE PROTEIN POLYMERS IN PERSONAL CARE COMPOSITIONS

(75) Inventor: Manoj Kumar, Fremont, CA (US)

(73) Assignee: Danisco US Inc., Palo Alto, CA (US)

( * ) Notice: Subject to any disclaimer, the term of this patent is extended or adjusted under 35 U.S.C. 154(b) by 1146 days.

This patent is subject to a terminal disclaimer.

(21) Appl. No.: 12/062,305

(22) Filed: Apr. 3, 2008

(65) Prior Publication Data

US 2008/0226706 A1    Sep. 18, 2008

Related U.S. Application Data

(63) Continuation of application No. 10/939,036, filed on Sep. 10, 2004, now abandoned, which is a continuation-in-part of application No. 10/800,179, filed on Mar. 12, 2004, now Pat. No. 7,297,678.

(60) Provisional application No. 60/454,077, filed on Mar. 12, 2003.

(51) Int. Cl.
*A61K 38/00* (2006.01)
*A61K 51/00* (2006.01)
*C07K 14/00* (2006.01)
*C07K 17/00* (2006.01)
*C07K 16/00* (2006.01)
*C07K 1/00* (2006.01)
*A23J 1/00* (2006.01)

(52) U.S. Cl. ......... 514/1.1; 530/350; 530/412; 530/427; 424/1.69

(58) Field of Classification Search ................. None
See application file for complete search history.

(56) References Cited

U.S. PATENT DOCUMENTS

| | | | |
|---|---|---|---|
| 3,755,560 A | 8/1973 | Dickert et al. | 424/78 |
| 3,929,678 A | 12/1975 | Laughlin et al. | 252/526 |
| 4,076,663 A | 2/1978 | Masuda et al. | 260/17.4 |
| 4,152,416 A | 5/1979 | Spitzer et al. | 424/46 |
| 4,325,741 A | 4/1982 | Otoi et al. | 106/308 N |
| 4,421,769 A | 12/1983 | Dixon et al. | 424/358 |
| 4,937,370 A | 6/1990 | Sabatelli | 560/45 |
| 4,999,186 A | 3/1991 | Sabatelli et al. | 424/60 |
| 5,011,681 A | 4/1991 | Ciotti et al. | 424/81 |
| 5,073,371 A | 12/1991 | Turner et al. | 424/401 |
| 5,073,372 A | 12/1991 | Turner et al. | 424/401 |
| 5,087,372 A | 2/1992 | Toyomoto et al. | 210/651 |
| 5,243,038 A | 9/1993 | Ferrari et al. | 536/23.1 |
| 5,382,431 A | 1/1995 | Pickart | 424/401 |
| 5,412,074 A | 5/1995 | Jones et al. | 530/353 |
| 5,606,019 A | 2/1997 | Cappello | 530/329 |
| 5,626,853 A | 5/1997 | Bara et al. | 424/401 |
| 5,627,148 A | 5/1997 | Dubief et al. | 510/122 |
| 5,679,543 A | 10/1997 | Lawlis | 435/69.1 |
| 5,723,588 A | 3/1998 | Donofrio et al. | 530/817 |
| 5,747,015 A | 5/1998 | Oshika et al. | 424/70.14 |
| 5,770,697 A | 6/1998 | Ferrari et al. | 530/353 |
| 5,808,012 A | 9/1998 | Donofrio et al. | 530/815 |
| 5,827,508 A | 10/1998 | Tanner et al. | 424/59 |
| 5,935,556 A | 8/1999 | Tanner et al. | 424/59 |
| 5,945,086 A | 8/1999 | Bassi et al. | 424/45 |
| 5,968,485 A | 10/1999 | Robinson | 424/59 |
| 5,972,316 A | 10/1999 | Robinson | 424/59 |
| 6,004,444 A | 12/1999 | Aksay et al. | 204/515 |
| 6,018,030 A | 1/2000 | Ferrari et al. | 530/353 |
| 6,033,654 A | 3/2000 | Stedronsky et al. | 424/78.02 |
| 6,034,220 A | 3/2000 | Stedronsky | 530/353 |
| 6,140,072 A | 10/2000 | Ferrari et al. | 435/69.1 |
| 6,153,602 A | 11/2000 | Dubief et al. | 514/63 |
| 6,175,053 B1 | 1/2001 | Tsubouchi | 602/43 |
| 6,184,348 B1 | 2/2001 | Ferrari et al. | 530/350 |
| 6,228,248 B1 | 5/2001 | Aksay et al. | 205/687 |
| 6,280,747 B1 | 8/2001 | Philippe et al. | 424/401 |
| 6,296,860 B1 | 10/2001 | Hasegawa et al. | 424/401 |
| 6,355,776 B1 | 3/2002 | Ferrari et al. | 530/350 |
| 6,358,501 B1 | 3/2002 | Dietz et al. | 424/70.12 |
| 6,365,661 B1 | 4/2002 | Fischer et al. | 524/445 |
| 6,365,877 B1 | 4/2002 | Chen et al. | 219/400 |
| 6,368,606 B1 | 4/2002 | Dubief et al. | 424/401 |
| 6,380,154 B1 | 4/2002 | Cappello et al. | 514/2 |
| 6,423,333 B1 | 7/2002 | Stedronsky et al. | 424/423 |
| 7,297,678 B2 * | 11/2007 | Kumar et al. | 514/18.8 |
| 7,456,147 B2 * | 11/2008 | Kumar et al. | 514/1.1 |
| 7,691,806 B2 * | 4/2010 | Collier et al. | 514/18.8 |
| 2001/0006664 A1 | 7/2001 | Ensley | 424/401 |

(Continued)

FOREIGN PATENT DOCUMENTS

DE          31 39 438 A1       4/1983

(Continued)

OTHER PUBLICATIONS

Alley, M. C. et al., "Feasibility of Drug Screening with Panels of Human Tumor Cell Lines Using a Microculture Tetrazolium Assay," *Cancer Research*, 48:589-601, 1988.
Andersson, L. et al., "Large-Scale Synthesis of Peptides," *Biopolymers (Peptide Science)*, 55:227-250, 2000.
Arkles, Barry, "Commercial Applications of Sol-Gel-Derived Hybrid Materials," *MRS Bulletin*, pp. 402-408 (May 2001).
Balsam, M. S. and Sagarin, E. (Eds.), *Cosmetics, Science and Technology*, 2nd Edition, vol. 1, pp. 32-43, 1972.
Brott et al., "Ultrafast holographic nanopatterning of biocatalytically formed silica," *Letters to Nature*, 413:291-293 (2001).
Cappello, J., "Genetically Engineered Protein Polymers, in *Handbook of Biodegradable Polymers*," Domb et al. (eds.), Harvard Acdemic Publishers, Amsterdam ; pp. 387-414, 1997.

(Continued)

*Primary Examiner* — Maury Audet
(74) *Attorney, Agent, or Firm* — Danisco US Inc.

(57) ABSTRACT

The present invention provides personal care compositions, and more particularly, personal care compositions comprising a bioactively effective amount of a repeat sequence protein polymer. In some particularly preferred embodiments, the present invention provides personal care compositions comprising an effective amount of at least one fragment of a repeat sequence protein polymer having bioactivity.

4 Claims, 20 Drawing Sheets

U.S. PATENT DOCUMENTS

| | | |
|---|---|---|
| 2001/0013294 A1 | 8/2001 | Bruno et al. .................. 101/327 |
| 2001/0027570 A1 | 10/2001 | Blees ............................. D18/15 |
| 2002/0045567 A1 | 4/2002 | Cappello et al. .................. 514/2 |
| 2002/0064539 A1 | 5/2002 | Philippe et al. ............... 424/401 |
| 2003/0104589 A1 | 6/2003 | Stedronsky et al. .......... 435/174 |
| 2003/0176355 A1 | 9/2003 | Cappello et al. ................ 514/17 |
| 2004/0180027 A1 | 9/2004 | Kumar et al. .............. 424/70.14 |
| 2004/0228913 A1 | 11/2004 | Kumar et al. ................. 424/468 |
| 2004/0234609 A1 | 11/2004 | Collier et al. ................. 424/488 |

FOREIGN PATENT DOCUMENTS

| | | |
|---|---|---|
| EP | 540 357 A2 | 5/1993 |
| EP | 0 699 431 A1 | 3/1996 |
| WO | WO 96/03964 | 2/1996 |
| WO | WO 96/16636 | 6/1996 |
| WO | WO 98/22085 | 5/1998 |
| WO | WO 00/06110 | 2/2000 |
| WO | WO 00/24372 | 5/2000 |
| WO | WO 00/35993 | 6/2000 |
| WO | WO 01/46213 A2 | 6/2001 |
| WO | WO 01/87825 A1 | 11/2001 |
| WO | WO 2004/044172 A2 | 5/2004 |

OTHER PUBLICATIONS

Capello et al., "In-situ self-assembling protein polymer gel systems for administration, delivery, and release of drugs," *Journal of Controlled Release*, 53:105-117 (1998).

Carini, M. et al., "Fluorescent probes as markers of oxidative stress in keratinocyte cell lines following UVB exposure," *Il Farmaco*, 55:526-534, 2000.

Chan, Wen-Hsiung et al., "Curcumin Inhibits UV Irradition-Induced Oxidative Stress and Apoptotic Biochemical Changes in Human Eidermoid Carcinoma A431 Cells," *Journal of Cellular Biochemistry*, 90:327-338, 2003.

Chardon, A. et al., "Skin colour typology and suntanning pathways," *International Journal of Cosmetic Science*, 13:191-208 (1991).

Coradin et al., "Biogenic Silica Patterning: Simple Chemistry or Subtle Biology," *ChemBioChem*, 3:1-9 (2003).

CTFA International Cosmetic Ingredient Dictionary, 6$^{th}$ Edition, pp. 1026-1028 (1995).

Deming, "Facile synthesis of block copolypeptides of defined architecture," *Letters to Nature*, 390:386-389 (1997).

Fan et al., "Rapid prototyping of patterned functional nanostructures," *Letters to Nature*, 405:56-60 (2000).

Gosline et al., "Elastic proteins: biological roles and mechanical properties," *The Royal Society*, 357:121-132 (2002).

Grove, G. L. et al.,"Optical profilometry: An objective method for quantification of facial wrinkles," *J. Am. Acad. Dermatol.*, 21:631-637, 1989.

Hartgerink et al., "Peptide-amphiphile nanofibers : A versatile scaffold for the preparation of self-assembling materials," 99(8):5133-5138 (2002).

Huo et al., "Generalized synthesis of periodic surfactant/inorganic composite materials," *Letters to Nature*, 368:317-321 (1994).

Kröger et al., "Polycationic Peptides from Diatom Biosilica That Direct Silica Nanosphere Formation," *Science*, 286:1129-1132 (1999).

Kröger et al., "Silica-precipitating Peptides from Diatoms," , The Chemical Structure of Silaffin-1A From *Cylindrotheca fusiformis*, *J. Biol. Chem.*, 276(28):26066-26070 (2001).

Lowe and Shaath (eds.), *Sunscreens : Development, Evaluation, and Regulatory Aspects*, Marcel Dekker, Inc., 1990.

Megeed, Z. et al., "Genetically engineered silk-elastinlike protein polymers for controlled drug delivery," *Advanced Drug Delivery Reviews*, 54:1075-1091, 2002.

Megeed, Z. et al., "Thermal Analysis of Water in Silk—Elastinlike Hydrogels by Differential Scanning Calorimetry," *Biomacromlecules*, 5:793-797, 2004.

Mizutani et al., "Silicic Acid Polymerization Catalyzed by Amines and Polyamines," *Bull. Chem. Soc.* Jpn., 71:2017-2022, 1998.

Mizutani et al., "Silicic Acid Polymerization Catalyzed by Amines and Polyamines," *Chemistry Letters*, pp. 133-134, 1998.

Naik et al., "Silica-Precipitating Peptides Isolated from a Combinatorial Phage Display Peptide Library," *Journal of Nanoscience and Nanotechnology*, 2:95-100, 2002.

Packman, E. W. et al., "Topical moisturizers: quantification of their effect on superficial facial lines," *J. Soc. Cosmet. Chem.*, 29:79-90, 1978.

Ranney, D. F., "Biomimetic Transport and Rational Drug Delivery," *Biochemical Pharmacology*, 59:105-114, 2000.

Sarikaya, "Biomimetics: Materials fabrication through biology," *PNAS*, 96(25):14183-14185, 1999.

Sayre et al., "Physical Sunscreens," *J. Soc. Cosmet Chem.*, 41(2):103-109, 1990.

von Döhren, H. et al., "Multifunctional Peptide Synthetases," *Chem. Rev.*, 97:2675-2705, 1997.

Wong, C.-H. et al., "New developments in enzymatic peptide synthesis," *Experientia*, 47:1123-1129, 1991.

Zhang, "Emerging biological materials through molecular self-assembly," *Biotechnology Advances*, 20:321-339, 2002.

Zhou et al., "Efficient Catalysis of Polysiloxane Synthesis by Silicatein α Requires Specific Hydroxy and Imidazole Functionalities," *Agnew. Chem. Int. Ed.*, 38(6):779-782, 1999.

\* cited by examiner

FIGURE 4A

```
<210> 1
<211> 6
<212> PRT
<213> Unknown

<220>
<223> Silk-like protein

<400> 1

Ser Gly Ala Gly Ala Gly
 1               5

<210> 2
<211> 53
<212> PRT
<213> Unknown

<220>
<223> Silk fibroin protein

<400> 2

Gly Ala Gly Ala Gly Ser Gly Ala Gly Ala Gly Ser Gly Ala Gly Ala
 1               5                  10                  15
Gly Ser Gly Ala Gly Ala Gly Ser Gly Ala Gly Ala Gly Ser Gly Ala
             20                  25                  30
Gly Ala Gly Ser Gly Ala Gly Ala Gly Ser Gly Ala Gly Ala Gly Ser
             35                  40                  45
Gly Ala Ala Gly Tyr
         50

<210> 3
<211> 5
<212> PRT
<213> Unknown

<220>
<223> Elastin-like protein

<400> 3

Gly Val Gly Val Pro
 1               5

<210> 4
<211> 10
<212> PRT
<213> Unknown

<220>
<223> Abductin-like protein

<220>
<221> MISC_FEATURE
<222> (10)..(10)
<223> X = any amino acid

<400> 4

Gly Gly Phe Gly Gly Met Gly Gly Gly Xaa
 1               5                  10

```
<212> PRT
<213> Unknown

<220>
<223> Byssus-like protein

<400> 5

Gly Pro Gly Gly Gly
 1               5

<210> 6
<211> 6
<212> PRT
<213> Unknown

<220>
<223> Gluten-like protein

<400> 6

Pro Gly Gln Gly Gln Gln
 1               5

<210> 7
<211> 9
<212> PRT
<213> Unknown

<220>
<223> Gluten-like protein

<400> 7

Gly Tyr Tyr Pro Thr Ser Pro Gln Gln
 1               5

<210> 8
<211> 3
<212> PRT
<213> Unknown

<220>
<223> Gluten-like protein

<400> 8

Gly Gln Gln
 1

<210> 9
<211> 28
<212> PRT
<213> Unknown

<220>
<223> Titin-like protein

<400> 9

Pro Pro Ala Lys Val Pro Glu Val Pro Lys Lys Pro Val Pro Glu Glu
 1               5                  10                  15
Lys Val Pro Val Pro Val Pro Lys Lys Pro Glu Ala
                20                  25
```

FIGURE 4C

```
<210> 10
<211> 12
<212> PRT
<213> Unknown

<220>
<223> Extensin-like protein

<400> 10

Ser Pro Pro Pro Pro Ser Pro Lys Tyr Val Tyr Lys
1               5                   10

<210> 11
<211> 4
<212> PRT
<213> Unknown

<220>
<223> Fibronectin-like protein

<400> 11

Arg Gly Asp Ser
1

<210> 12
<211> 5
<212> PRT
<213> Unknown

<220>
<223> Gliadin

<400> 12

Pro Gln Gln Pro Tyr
1               5

<210> 13
<211> 5
<212> PRT
<213> Unknown

<220>
<223> Glue polypeptide

<400> 13

Pro Thr Thr Thr Lys
1               5

<210> 14
<211> 8
<212> PRT
<213> Unknown

<220>
<223> Ice nucleating protein

<400> 14

Ala Gly Tyr Gly Ser Thr Gly Thr
1               5
```

FIGURE 4D

```
<210> 15
<211> 8
<212> PRT
<213> Unknown

<220>
<223> Keratin

<400> 15

Tyr Gly Gly Ser Ser Gly Gly Gly
 1               5

<210> 16
<211> 5
<212> PRT
<213> Unknown

<220>
<223> Keratin

<400> 16

Phe Gly Gly Gly Ser
 1               5

<210> 17
<211> 6
<212> PRT
<213> Unknown

<220>
<223> Mucin

<400> 17

Thr Thr Thr Pro Asp Val
 1               5

<210> 18
<211> 7
<212> PRT
<213> Unknown

<220>
<223> RNA polymerase II

<400> 18

Tyr Ser Pro Thr Ser Pro Ser
 1               5

<210> 19
<211> 780
<212> PRT
<213> Unknown

<220>
<223> SELP 47K

<400> 19

Gly Ala Gly Ala Gly Ser Gly Ala Gly Ala Gly Ser Gly Val Gly Val
 1               5                   10                  15
Pro Gly Val Gly Val Pro Gly Val Gly Val Pro Gly Lys Gly Val Pro
```

FIGURE 4E

```
               20                  25                  30
Gly Val Gly Pro Gly Val Gly Pro Gly Val Gly Pro Gly Val Gly Pro
         35                  40                  45
Gly Ala Gly Ala Gly Ser Gly Ala Gly Ala Gly Ser Gly Ala Gly Ala
 50                  55                  60
Gly Ser Gly Ala Gly Ala Gly Ser Gly Val Gly Val Pro Gly Val Gly
 65                  70                  75                  80
Val Pro Gly Val Gly Val Pro Gly Lys Gly Val Pro Gly Val Gly Pro
                 85                  90                  95
Gly Val Gly Pro Gly Val Gly Pro Gly Val Gly Pro Gly Ala Gly Ala
            100                 105                 110
Gly Ser Gly Ala Gly Ala Gly Ser Gly Ala Gly Ala Gly Ser Gly Ala
         115                 120                 125
Gly Ala Gly Ser Gly Val Gly Val Pro Gly Val Gly Val Pro Gly Val
    130                 135                 140
Gly Val Pro Gly Lys Gly Val Pro Gly Val Gly Pro Gly Val Gly Pro
145                 150                 155                 160
Gly Val Gly Pro Gly Val Gly Pro Gly Ala Gly Ala Gly Ser Gly Ala
                165                 170                 175
Gly Ala Gly Ser Gly Ala Gly Ala Gly Ser Gly Ala Gly Ala Gly Ser
            180                 185                 190
Gly Val Gly Val Pro Gly Val Gly Val Pro Gly Val Gly Val Pro Gly
         195                 200                 205
Lys Gly Val Pro Gly Val Gly Pro Gly Val Gly Pro Gly Val Gly Pro
    210                 215                 220
Gly Val Gly Pro Gly Ala Gly Ala Gly Ser Gly Ala Gly Ala Gly Ser
225                 230                 235                 240
Gly Ala Gly Ala Gly Ser Gly Ala Gly Ala Gly Ser Gly Val Gly Val
                245                 250                 255
Pro Gly Val Gly Val Pro Gly Val Gly Val Pro Gly Lys Gly Val Pro
            260                 265                 270
Gly Val Gly Pro Gly Val Gly Pro Gly Val Gly Pro Gly Val Gly Pro
         275                 280                 285
Gly Ala Gly Ala Gly Ser Gly Ala Gly Ala Gly Ser Gly Ala Gly Ala
    290                 295                 300
Gly Ser Gly Ala Gly Ala Gly Ser Gly Val Gly Val Pro Gly Val Gly
305                 310                 315                 320
Val Pro Gly Val Gly Val Pro Gly Lys Gly Val Pro Gly Val Gly Pro
                325                 330                 335
Gly Val Gly Pro Gly Val Gly Pro Gly Val Gly Pro Gly Ala Gly Ala
            340                 345                 350
Gly Ser Gly Ala Gly Ala Gly Ser Gly Ala Gly Ala Gly Ser Gly Ala
         355                 360                 365
Gly Ala Gly Ser Gly Val Gly Val Pro Gly Val Gly Val Pro Gly Val
    370                 375                 380
Gly Val Pro Gly Lys Gly Val Pro Gly Val Gly Pro Gly Val Gly Pro
385                 390                 395                 400
Gly Val Gly Pro Gly Val Gly Pro Gly Ala Gly Ala Gly Ser Gly Ala
                405                 410                 415
Gly Ala Gly Ser Gly Ala Gly Ala Gly Ser Gly Ala Gly Ala Gly Ser
            420                 425                 430
Gly Val Gly Val Pro Gly Val Gly Val Pro Gly Val Gly Val Pro Gly
         435                 440                 445
Lys Gly Val Pro Gly Val Gly Pro Gly Val Gly Pro Gly Val Gly Pro
    450                 455                 460
Gly Val Gly Pro Gly Ala Gly Ala Gly Ser Gly Ala Gly Ala Gly Ser
465                 470                 475                 480
Gly Ala Gly Ala Gly Ser Gly Ala Gly Ala Gly Ser Gly Val Gly Val
                485                 490                 495
Pro Gly Val Gly Val Pro Gly Val Gly Val Pro Gly Lys Gly Val Pro
            500                 505                 510
Gly Val Gly Pro Gly Val Gly Pro Gly Val Gly Pro Gly Val Gly Pro
         515                 520                 525
Gly Ala Gly Ala Gly Ser Gly Ala Gly Ala Gly Ser Gly Ala Gly Ala
    530                 535                 540
```

FIGURE 4F

```
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
                565                 570                 575
Gly Val Gly Pro Gly Val Gly Pro Gly Val Gly Pro Gly Ala Gly Ala
                580                 585                 590
Gly Ser Gly Ala Gly Ala Gly Ser Gly Ala Gly Ala Gly Ser Gly Ala
            595                 600                 605
Gly Ala Gly Ser Gly Val Gly Val Pro Gly Val Gly Val Pro Gly Val
        610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
                645                 650                 655
Gly Ala Gly Ser Gly Ala Gly Ala Gly Ser Gly Ala Gly Ala Gly Ser
            660                 665                 670
Gly Val Gly Val Pro Gly Val Gly Val Pro Gly Val Gly Val Pro Gly
        675                 680                 685
Lys Gly Val Pro Gly Val Gly Pro Gly Val Gly Pro Gly Val Gly Pro
    690                 695                 700
Gly Val Gly Pro Gly Ala Gly Ala Gly Ser Gly Ala Gly Ala Gly Ser
705                 710                 715                 720
Gly Ala Gly Ala Gly Ser Gly Ala Gly Ala Gly Ser Gly Val Gly Val
                725                 730                 735
Pro Gly Val Gly Val Pro Gly Val Gly Val Pro Gly Lys Gly Val Pro
                740                 745                 750
Gly Val Gly Pro Gly Val Gly Pro Gly Val Gly Pro Gly Val Gly Pro
            755                 760                 765
Gly Ala Gly Ala Gly Ser Gly Ala Gly Ala Gly Ser
770                 775                 780
```

<210> 20
<211> 3
<212> PRT
<213> Unknown

<220>
<223> Abductin-like protein

<220>
<221> MISC_FEATURE
<222> (2)..(2)
<223> X = any amino acid

<220>
<221> MISC_FEATURE
<222> (3)..(3)
<223> X = any amino acid

<400> 20

Gly Xaa Xaa
 1

<210> 21
<211> 39
<212> DNA
<213> Unknown

<220>
<223> Primer 5' to 3' Glutamic Acid conversion

<400> 21
gggagttggt gtacctggag aaggtgttcc gggggtagg      39

FIGURE 4G

```
<210> 22
<211> 39
<212> DNA
<213> Unknown

<220>
<223> Primer 3' to 5' Glutamic Acid conversion

<400> 22
ccctcaacca catggacctc ttccacaagg cccccatcc                    39

<210> 23
<211> 39
<212> DNA
<213> Unknown

<220>
<223> Primer 5' to 3' Arginine conversion

<400> 23
gggagttggg gtacctggac gaggtgttcc gggggtagg                    39

<210> 24
<211> 39
<212> DNA
<213> Unknown

<220>
<223> Primer 3' to 5' Arginine conversion

<400> 24
gggagttggg gtacctggac gaggtgttcc gggggtagg                    40

<210> 25
<211> 884
<212> PRT
<213> Unknown

<220>
<223> SELP 47E-13

<400> 25
```

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Gly Ser Gly Ala Gly Ala Gly Ser Gly Val Gly Val Pro
        35                  40                  45
Gly Val Gly Val Pro Gly Val Gly Val Pro Gly Val Gly Val Pro Gly
    50                  55                  60
Glu Gly Val Pro Gly Val Gly Val Pro Gly Val Gly Glu Pro Gly Val
65                  70                  75                  80
Gly Val Pro Gly Ala Gly Ala Gly Ser Gly Ala Gly Ala Gly Ser Gly
                85                  90                  95
Ala Gly Ala Gly Ser Gly Ala Gly Ala Gly Ser Gly Val Gly Val Pro
            100                 105                 110
Gly Val Gly Val Pro Gly Val Gly Val Pro Gly Val Gly Val Pro Gly
        115                 120                 125
Glu Gly Val Pro Gly Val Gly Val Pro Gly Val Gly Glu Pro Gly Val
    130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
                165                 170                 175

FIGURE 4H

Gly Val Gly Val Pro Gly Val Gly Val Pro Gly Val Gly Val Pro Gly
                180               185               190
Glu Gly Val Pro Gly Val Gly Val Pro Gly Val Gly Glu Pro Gly Val
            195               200               205
Gly Val Pro Gly Ala Gly Ala Gly Ser Gly Ala Gly Ala Gly Ser Gly
        210               215               220
Ala Gly Ala Gly Ser Gly Ala Gly Ala Gly Ser Gly Val Gly Val Pro
225               230               235               240
Gly Val Gly Val Pro Gly Val Gly Val Pro Gly Val Gly Val Pro Gly
            245               250               255
Glu Gly Val Pro Gly Val Gly Val Pro Gly Val Gly Glu Pro Gly Val
            260               265               270
Gly Val Pro Gly Ala Gly Ala Gly Ser Gly Ala Gly Ala Gly Ser Gly
        275               280               285
Ala Gly Ala Gly Ser Gly Ala Gly Ala Gly Ser Gly Val Gly Val Pro
        290               295               300
Gly Val Gly Val Pro Gly Val Gly Val Pro Gly Val Gly Val Pro Gly
305               310               315               320
Glu Gly Val Pro Gly Val Gly Val Pro Gly Val Gly Glu Pro Gly Val
            325               330               335
Gly Val Pro Gly Ala Gly Ala Gly Ser Gly Ala Gly Ala Gly Ser Gly
            340               345               350
Ala Gly Ala Gly Ser Gly Ala Gly Ala Gly Ser Gly Val Gly Val Pro
        355               360               365
Gly Val Gly Val Pro Gly Val Gly Val Pro Gly Val Gly Val Pro Gly
        370               375               380
Glu Gly Val Pro Gly Val Gly Val Pro Gly Val Gly Glu Pro Gly Val
385               390               395               400
Gly Val Pro Gly Ala Gly Ala Gly Ser Gly Ala Gly Ala Gly Ser Gly
            405               410               415
Ala Gly Ala Gly Ser Gly Ala Gly Ala Gly Ser Gly Val Gly Val Pro
            420               425               430
Gly Val Gly Val Pro Gly Val Gly Val Pro Gly Val Gly Val Pro Gly
            435               440               445
Glu Gly Val Pro Gly Val Gly Val Pro Gly Val Gly Glu Pro Gly Val
        450               455               460
Gly Val Pro Gly Ala Gly Ala Gly Ser Gly Ala Gly Ala Gly Ser Gly
465               470               475               480
Ala Gly Ala Gly Ser Gly Ala Gly Ala Gly Ser Gly Val Gly Val Pro
            485               490               495
Gly Val Gly Val Pro Gly Val Gly Val Pro Gly Val Gly Val Pro Gly
            500               505               510
Glu Gly Val Pro Gly Val Gly Val Pro Gly Val Gly Glu Pro Gly Val
        515               520               525
Gly Val Pro Gly Ala Gly Ala Gly Ser Gly Ala Gly Ala Gly Ser Gly
        530               535               540
Ala Gly Ala Gly Ser Gly Ala Gly Ala Gly Ser Gly Val Gly Val Pro
545               550               555               560
Gly Val Gly Val Pro Gly Val Gly Val Pro Gly Val Gly Val Pro Gly
            565               570               575
Glu Gly Val Pro Gly Val Gly Val Pro Gly Val Gly Glu Pro Gly Val
            580               585               590
Gly Val Pro Gly Ala Gly Ala Gly Ser Gly Ala Gly Ala Gly Ser Gly
        595               600               605
Ala Gly Ala Gly Ser Gly Ala Gly Ala Gly Ser Gly Val Gly Val Pro
        610               615               620
Gly Val Gly Val Pro Gly Val Gly Val Pro Gly Val Gly Val Pro Gly
625               630               635               640
Glu Gly Val Pro Gly Val Gly Val Pro Gly Val Gly Glu Pro Gly Val
            645               650               655
Gly Val Pro Gly Ala Gly Ala Gly Ser Gly Ala Gly Ala Gly Ser Gly
            660               665               670
Ala Gly Ala Gly Ser Gly Ala Gly Ala Gly Ser Gly Val Gly Val Pro
        675               680               685
Gly Val Gly Val Pro Gly Val Gly Val Pro Gly Val Gly Val Pro Gly

FIGURE 4I

```
            690                695                700
Glu Gly Val Pro Gly Val Gly Val Pro Gly Val Gly Glu Pro Gly Val
705                710                715                720
Gly Val Pro Gly Ala Gly Ala Gly Ser Gly Ala Gly Ala Gly Ser Gly
                725                730                735
Ala Gly Ala Gly Ser Gly Ala Gly Ala Gly Ser Gly Val Gly Val Pro
            740                745                750
Gly Val Gly Val Pro Gly Val Gly Val Pro Gly Val Gly Val Pro Gly
                755                760                765
Glu Gly Val Pro Gly Val Gly Val Pro Gly Val Gly Glu Pro Gly Val
            770                775                780
Gly Val Pro Gly Ala Gly Ala Gly Ser Gly Ala Gly Ala Gly Ser Gly
785                790                795                800
Ala Gly Ala Gly Ser Gly Ala Gly Ala Gly Ser Gly Val Gly Val Pro
                805                810                815
Gly Val Gly Val Pro Gly Val Gly Val Pro Gly Val Gly Val Pro Gly
            820                825                830
Glu Gly Val Pro Gly Val Gly Val Pro Gly Val Gly Glu Pro Gly Val
                835                840                845
Gly Val Pro Gly Ala Gly Ala Gly Ser Gly Ala Gly Ala Gly Ser Gly
            850                855                860
Ala Gly Ala Met Asp Pro Gly Arg Tyr Gln Asp Leu Arg Ser His His
865                870                875                880
His His His His
```

<210> 26
<211> 246
<212> PRT
<213> Unknown

<220>
<223> SELP 47R-3

<400> 26

```
Met Pro Pro Val Val Leu Gln Arg Arg Asp Trp Glu Asn Pro Gly Val
 1               5                 10                15
Thr Gln Leu Asn Arg Leu Ala Ala His Pro Pro Phe Ala Ser Asp Pro
            20                25                30
Met Gly Ala Gly Ala Gly Ser Gly Ala Gly Ala Gly Ser Gly Val Gly
        35                40                45
Val Pro Gly Val Gly Val Pro Gly Val Gly Val Pro Gly Val Gly Val
    50                55                60
Pro Gly Arg Gly Val Pro Gly Val Gly Val Pro Gly Val Gly Val Pro
65              70                75                 80
Gly Val Gly Val Pro Gly Ala Gly Ala Gly Ser Gly Ala Gly Ala Gly
                85                90                95
Ser Gly Ala Gly Ala Gly Ser Gly Ala Gly Ala Gly Ser Gly Val Gly
            100                105                110
Val Pro Gly Val Gly Val Pro Gly Val Gly Val Pro Gly Val Gly Val
        115                120                125
Pro Gly Arg Gly Val Pro Gly Val Gly Val Pro Gly Val Gly Val Pro
    130                135                140
Gly Val Gly Val Pro Gly Ala Gly Ala Gly Ser Gly Ala Gly Ala Gly
145                150                155                160
Ser Gly Ala Gly Ala Gly Ser Gly Ala Gly Ala Gly Ser Gly Val Gly
                165                170                175
Val Pro Gly Val Gly Val Pro Gly Val Gly Val Pro Gly Val Gly Val
            180                185                190
Pro Gly Arg Gly Val Pro Gly Val Gly Val Pro Gly Val Gly Val Pro
        195                200                205
Gly Val Gly Val Pro Gly Ala Gly Ala Gly Ser Gly Ala Gly Ala Gly
    210                215                220
Ser Gly Ala Gly Ala Met Asp Pro Gly Arg Tyr Gln Asp Leu Arg Ser
```

FIGURE 4J 225 230 235 240
His His His His His His
245

<210> 27
<211> 244
<212> PRT
<213> Unknown

<220>
<223> SELP 47K-3

<400> 27

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Gly Ser Gly Ala Gly Ala Gly Ser Gly Val Gly Val Pro
        35                  40                  45
Gly Val Gly Val Pro Gly Val Gly Val Pro Gly Val Gly Val Pro Gly
    50                  55                  60
Lys Gly Val Pro Gly Val Gly Val Pro Gly Val Gly Val Pro Gly Val
65                  70                  75                  80
Gly Val Pro Gly Ala Gly Ala Gly Ser Gly Ala Gly Ala Gly Ser Gly
                85                  90                  95
Ala Gly Ala Gly Ser Gly Ala Gly Ala Gly Ser Gly Val Gly Val Pro
            100                 105                 110
Gly Val Gly Val Pro Gly Val Gly Val Pro Gly Val Gly Val Pro Gly
        115                 120                 125
Lys Gly Val Pro Gly Val Gly Val Pro Gly Val Gly Val Pro Gly Val
    130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
                165                 170                 175
Gly Val Gly Val Pro Gly Val Gly Val Pro Gly Val Gly Val Pro Gly
            180                 185                 190
Lys Gly Val Pro Gly Val Gly Val Pro Gly Val Gly Val Pro Gly Val
        195                 200                 205
Gly Val Pro Gly Ala Gly Ala Gly Ser Gly Ala Gly Ala Gly Ser Gly
    210                 215                 220
Ala Gly Ala Met Asp Pro Gly Arg Tyr Gln Asp Leu Arg Ser His His
225                 230                 235                 240
His His His His

<210> 28
<211> 246
<212> PRT
<213> Unknown

<220>
<223> SELP 47E-3

<400> 28

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Gly Ala Gly Ser Gly Ala Gly Ala Gly Ser Gly Val Gly
        35                  40                  45
Val Pro Gly Val Gly Val Pro Gly Val Gly Val Pro Gly Val Gly Val
    50                  55                  60

FIGURE 4K

```
Pro Gly Glu Gly Val Pro Gly Val Gly Val Pro Gly Val Gly Val Pro
65                  70                  75                  80
Gly Val Gly Val Pro Gly Ala Gly Ala Gly Ser Gly Ala Gly Ala Gly
                85                  90                  95
Ser Gly Ala Gly Ala Gly Ser Gly Ala Gly Ala Gly Ser Gly Val Gly
            100                 105                 110
Val Pro Gly Val Gly Val Pro Gly Val Gly Val Pro Gly Val Gly Val
        115                 120                 125
Pro Gly Glu Gly Val Pro Gly Val Gly Val Pro Gly Val Gly Val Pro
    130                 135                 140
Gly Val Gly Val Pro Gly Ala Gly Ala Gly Ser Gly Ala Gly Ala Gly
145                 150                 155                 160
Ser Gly Ala Gly Ala Gly Ser Gly Ala Gly Ala Gly Ser Gly Val Gly
                165                 170                 175
Val Pro Gly Val Gly Val Pro Gly Val Gly Val Pro Gly Val Gly Val
            180                 185                 190
Pro Gly Glu Gly Val Pro Gly Val Gly Val Pro Gly Val Gly Val Pro
        195                 200                 205
Gly Val Gly Val Pro Gly Ala Gly Ala Gly Ser Gly Ala Gly Ala Gly
    210                 215                 220
Ser Gly Ala Gly Ala Met Asp Pro Gly Arg Tyr Gln Asp Leu Arg Ser
225                 230                 235                 240
His His His His His His
                245

<210> 29
<211> 1063
<212> PRT
<213> Unknown

<220>
<223> Collagen-like protein

<400> 29

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala His Gly Pro Ala Gly Pro Lys Gly Ala His Gly Pro Ala
        35                  40                  45
Gly Pro Lys Gly Ala Gln Gly Pro Ala Gly Pro Gly Gly Ala Gln Gly
    50                  55                  60
Pro Ala Gly Pro Gly Gly Ala Gln Gly Pro Ala Gly Pro Gly Gly Ala
65                  70                  75                  80
Gln Gly Pro Ala Gly Pro Gly Gly Ala Gln Gly Pro Ala Gly Pro Gly
                85                  90                  95
Gly Ala Gln Gly Pro Ala Gly Pro Gly Gly Ala Gln Gly Pro Ala Gly
            100                 105                 110
Pro Gly Gly Ala Gln Gly Pro Ala Gly Pro Gly Gly Ala Gln Gly Pro
        115                 120                 125
Ala Gly Pro Gly Gly Ala Gln Gly Pro Ala Gly Pro Gly Gly Ala Gln
    130                 135                 140
Gly Pro Ala Gly Pro Gly Gly Ala Gln Gly Pro Ala Gly Pro Gly Gly
145                 150                 155                 160
Ala Gln Gly Pro Ala Gly Pro Gly Gly Ala Gln Gly Pro Ala Gly Pro
                165                 170                 175
Gly Gly Ala Gln Gly Pro Ala Gly Pro Gly Gly Ala Gln Gly Pro Ala
            180                 185                 190
Gly Pro Gly Gly Ala Gln Gly Pro Ala Gly Pro Gly Gly Ala Gln Gly
        195                 200                 205
Pro Ala Gly Pro Gly Gly Ala Gln Gly Pro Ala Gly Pro Gly Gly Ala
    210                 215                 220
Gln Gly Pro Ala Gly Pro Gly Gly Ala Gln Gly Pro Ala Gly Pro Gly
225                 230                 235                 240
```

FIGURE 4L

```
Gly Ala Gln Gly Pro Ala Gly Pro Gly Gly Ala Gln Gly Pro Ala Gly
                    245             250             255
Pro Gly Gly Ala Gln Gly Pro Ala Gly Pro Gly Gly Ala His Gly Pro
            260             265             270
Ala Gly Pro Lys Gly Ala His Gly Pro Ala Gly Pro Lys Gly Ala His
        275             280             285
Gly Pro Ala Gly Pro Lys Gly Ala His Gly Pro Ala Gly Pro Lys Gly
    290             295             300
Ala Gln Gly Pro Ala Gly Pro Gly Gly Ala Gln Gly Pro Ala Gly Pro
305             310             315             320
Gly Gly Ala Gln Gly Pro Ala Gly Pro Gly Gly Ala Gln Gly Pro Ala
                325             330             335
Gly Pro Gly Gly Ala Gln Gly Pro Ala Gly Pro Gly Gly Ala Gln Gly
            340             345             350
Pro Ala Gly Pro Gly Gly Ala Gln Gly Pro Ala Gly Pro Gly Gly Ala
        355             360             365
Gln Gly Pro Ala Gly Pro Gly Gly Ala Gln Gly Pro Ala Gly Pro Gly
    370             375             380
Gly Ala Gln Gly Pro Ala Gly Pro Gly Gly Ala Gln Gly Pro Ala Gly
385             390             395             400
Pro Gly Gly Ala Gln Gly Pro Ala Gly Pro Gly Gly Ala Gln Gly Pro
                405             410             415
Ala Gly Pro Gly Gly Ala Gln Gly Pro Ala Gly Pro Gly Gly Ala Gln
            420             425             430
Gly Pro Ala Gly Pro Gly Gly Ala Gln Gly Pro Ala Gly Pro Gly Gly
        435             440             445
Ala Gln Gly Pro Ala Gly Pro Gly Gly Ala Gln Gly Pro Ala Gly Pro
    450             455             460
Gly Gly Ala Gln Gly Pro Ala Gly Pro Gly Gly Ala Gln Gly Pro Ala
465             470             475             480
Gly Pro Gly Gly Ala Gln Gly Pro Ala Gly Pro Gly Gly Ala Gln Gly
                485             490             495
Pro Ala Gly Pro Gly Gly Ala Gln Gly Pro Ala Gly Pro Gly Gly Ala
            500             505             510
Gln Gly Pro Ala Gly Pro Gly Gly Ala His Gly Pro Ala Gly Pro Lys
        515             520             525
Gly Ala His Gly Pro Ala Gly Pro Lys Gly Ala His Gly Pro Ala Gly
    530             535             540
Pro Lys Gly Ala His Gly Pro Ala Gly Pro Lys Gly Ala Gln Gly Pro
545             550             555             560
Ala Gly Pro Gly Gly Ala Gln Gly Pro Ala Gly Pro Gly Gly Ala Gln
                565             570             575
Gly Pro Ala Gly Pro Gly Gly Ala Gln Gly Pro Ala Gly Pro Gly Gly
            580             585             590
Ala Gln Gly Pro Ala Gly Pro Gly Gly Ala Gln Gly Pro Ala Gly Pro
        595             600             605
Gly Gly Ala Gln Gly Pro Ala Gly Pro Gly Gly Ala Gln Gly Pro Ala
    610             615             620
Gly Pro Gly Gly Ala Gln Gly Pro Ala Gly Pro Gly Gly Ala Gln Gly
625             630             635             640
Pro Ala Gly Pro Gly Gly Ala Gln Gly Pro Ala Gly Pro Gly Gly Ala
                645             650             655
Gln Gly Pro Ala Gly Pro Gly Gly Ala Gln Gly Pro Ala Gly Pro Gly
            660             665             670
Gly Ala Gln Gly Pro Ala Gly Pro Gly Gly Ala Gln Gly Pro Ala Gly
        675             680             685
Pro Gly Gly Ala Gln Gly Pro Ala Gly Pro Gly Gly Ala Gln Gly Pro
    690             695             700
Ala Gly Pro Gly Gly Ala Gln Gly Pro Ala Gly Pro Gly Gly Ala Gln
705             710             715             720
Gly Pro Ala Gly Pro Gly Gly Ala Gln Gly Pro Ala Gly Pro Gly Gly
                725             730             735
Ala Gln Gly Pro Ala Gly Pro Gly Gly Ala Gln Gly Pro Ala Gly Pro
            740             745             750
Gly Gly Ala Gln Gly Pro Ala Gly Pro Gly Gly Ala Gln Gly Pro Ala
```

FIGURE 4M

```
              755                    760                    765
Gly Pro Gly Gly Ala His Gly Pro Ala Gly Pro Lys Gly Ala His Gly
         770                    775                    780
Pro Ala Gly Pro Lys Gly Ala His Gly Pro Ala Gly Pro Lys Gly Ala
785                    790                    795                    800
His Gly Pro Ala Gly Pro Lys Gly Ala Gln Gly Pro Ala Gly Pro Gly
                 805                    810                    815
Gly Ala Gln Gly Pro Ala Gly Pro Gly Gly Ala Gln Gly Pro Ala Gly
             820                    825                    830
Pro Gly Gly Ala Gln Gly Pro Ala Gly Pro Gly Gly Ala Gln Gly Pro
         835                    840                    845
Ala Gly Pro Gly Gly Ala Gln Gly Pro Ala Gly Pro Gly Gly Ala Gln
    850                    855                    860
Gly Pro Ala Gly Pro Gly Gly Ala Gln Gly Pro Ala Gly Pro Gly Gly
865                    870                    875                    880
Ala Gln Gly Pro Ala Gly Pro Gly Gly Ala Gln Gly Pro Ala Gly Pro
                 885                    890                    895
Gly Gly Ala Gln Gly Pro Ala Gly Pro Gly Gly Ala Gln Gly Pro Ala
             900                    905                    910
Gly Pro Gly Gly Ala Gln Gly Pro Ala Gly Pro Gly Gly Ala Gln Gly
         915                    920                    925
Pro Ala Gly Pro Gly Gly Ala Gln Gly Pro Ala Gly Pro Gly Gly Ala
     930                    935                    940
Gln Gly Pro Ala Gly Pro Gly Gly Ala Gln Gly Pro Ala Gly Pro Gly
945                    950                    955                    960
Gly Ala Gln Gly Pro Ala Gly Pro Gly Gly Ala Gln Gly Pro Ala Gly
                 965                    970                    975
Pro Gly Gly Ala Gln Gly Pro Ala Gly Pro Gly Gly Ala Gln Gly Pro
             980                    985                    990
Ala Gly Pro Gly Gly Ala Gln Gly Pro Ala Gly Pro Gly Gly Ala Gln
         995                   1000                   1005
Gly Pro Ala Gly Pro Gly Gly Ala Gln Gly Pro Ala Gly Pro Gly Gly
        1010                   1015                   1020
Ala His Gly Pro Ala Gly Pro Lys Gly Ala His Gly Pro Ala Gly Pro
1025                   1030                   1035                   1040
Lys Met Asp Pro Gly Arg Tyr Gln Leu Ser Ala Gly Arg Tyr His Tyr
                1045                   1050                   1055
Gln Leu Val Trp Cys Gln Lys
                1060
```

<210> 30
<211> 1038
<212> PRT
<213> Unknown

<220>
<223> SELP 67K

<400> 30

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
             20                  25                  30
Met Gly Val Gly Val Pro Gly Val Gly Val Pro Gly Val Gly Val Pro
         35                  40                  45
Gly Val Gly Val Pro Gly Lys Gly Val Pro Gly Val Gly Val Pro Gly
     50                  55                  60
Val Gly Val Pro Gly Val Gly Val Pro Gly Ala Gly Ala Gly Ser Gly
 65                  70                  75                  80
Ala Gly Ala Gly Ser Gly Ala Gly Ala Gly Ser Gly Ala Gly Ala Gly
                 85                  90                  95
Ser Gly Ala Gly Ala Gly Ser Gly Ala Gly Ala Gly Ser Gly Val Gly
             100                 105                 110
Val Pro Gly Val Gly Val Pro Gly Val Gly Val Pro Gly Val Gly Val
```

FIGURE 4N

```
             115                    120                    125
Pro Gly Lys Gly Val Pro Gly Val Gly Val Pro Gly Val Gly Val Pro
         130                    135                    140
Gly Val Gly Val Pro Gly Ala Gly Ala Gly Ser Gly Ala Gly Ala Gly
145                    150                    155                    160
Ser Gly Ala Gly Ala Gly Ser Gly Ala Gly Ala Gly Ser Gly Ala Gly
                 165                    170                    175
Ala Gly Ser Gly Ala Gly Ala Gly Ser Gly Val Gly Val Pro Gly Val
             180                    185                    190
Gly Val Pro Gly Val Gly Val Pro Gly Val Gly Val Pro Gly Lys Gly
         195                    200                    205
Val Pro Gly Val Gly Val Pro Gly Val Gly Val Pro Gly Val Gly Val
     210                    215                    220
Pro Gly Ala Gly Ala Gly Ser Gly Ala Gly Ala Gly Ser Gly Ala Gly
225                    230                    235                    240
Ala Gly Ser Gly Ala Gly Ala Gly Ser Gly Ala Gly Ala Gly Ser Gly
                 245                    250                    255
Ala Gly Ala Gly Ser Gly Val Gly Val Pro Gly Val Gly Val Pro Gly
             260                    265                    270
Val Gly Val Pro Gly Val Gly Val Pro Gly Lys Gly Val Pro Gly Val
         275                    280                    285
Gly Val Pro Gly Val Gly Val Pro Gly Val Gly Val Pro Gly Ala Gly
     290                    295                    300
Ala Gly Ser Gly Ala Gly Ala Gly Ser Gly Ala Gly Ala Gly Ser Gly
305                    310                    315                    320
Ala Gly Ala Gly Ser Gly Ala Gly Ala Gly Ser Gly Ala Gly Ala Gly
                 325                    330                    335
Ser Gly Val Gly Val Pro Gly Val Gly Val Pro Gly Val Gly Val Pro
             340                    345                    350
Gly Val Gly Val Pro Gly Lys Gly Val Pro Gly Val Gly Val Pro Gly
         355                    360                    365
Val Gly Val Pro Gly Val Gly Val Pro Gly Ala Gly Ala Gly Ser Gly
     370                    375                    380
Ala Gly Ala Gly Ser Gly Ala Gly Ala Gly Ser Gly Ala Gly Ala Gly
385                    390                    395                    400
Ser Gly Ala Gly Ala Gly Ser Gly Ala Gly Ala Gly Ser Gly Val Gly
                 405                    410                    415
Val Pro Gly Val Gly Val Pro Gly Val Gly Val Pro Gly Val Gly Val
             420                    425                    430
Pro Gly Lys Gly Val Pro Gly Val Gly Val Pro Gly Val Gly Val Pro
         435                    440                    445
Gly Val Gly Val Pro Gly Ala Gly Ala Gly Ser Gly Ala Gly Ala Gly
     450                    455                    460
Ser Gly Ala Gly Ala Gly Ser Gly Ala Gly Ala Gly Ser Gly Ala Gly
465                    470                    475                    480
Ala Gly Ser Gly Ala Gly Ala Gly Ser Gly Val Gly Val Pro Gly Val
                 485                    490                    495
Gly Val Pro Gly Val Gly Val Pro Gly Val Gly Val Pro Gly Lys Gly
             500                    505                    510
Val Pro Gly Val Gly Val Pro Gly Val Gly Val Pro Gly Val Gly Val
         515                    520                    525
Pro Gly Ala Gly Ala Gly Ser Gly Ala Gly Ala Gly Ser Gly Ala Gly
     530                    535                    540
Ala Gly Ser Gly Ala Gly Ala Gly Ser Gly Ala Gly Ala Gly Ser Gly
545                    550                    555                    560
Ala Gly Ala Gly Ser Gly Val Gly Val Pro Gly Val Gly Val Pro Gly
                 565                    570                    575
Val Gly Val Pro Gly Val Gly Val Pro Gly Lys Gly Val Pro Gly Val
             580                    585                    590
Gly Val Pro Gly Val Gly Val Pro Gly Val Gly Val Pro Gly Ala Gly
         595                    600                    605
Ala Gly Ser Gly Ala Gly Ala Gly Ser Gly Ala Gly Ala Gly Ser Gly
     610                    615                    620
Ala Gly Ala Gly Ser Gly Ala Gly Ala Gly Ser Gly Ala Gly Ala Gly
625                    630                    635                    640
```

FIGURE 40

Ser Gly Val Gly Val Pro Gly Val Gly Val Pro Gly Val Gly Val Pro
                645                 650                 655
Gly Val Gly Val Pro Gly Lys Gly Val Pro Gly Val Gly Val Pro Gly
                660                 665                 670
Val Gly Val Pro Gly Val Gly Val Pro Gly Ala Gly Ala Gly Ser Gly
                675                 680                 685
Ala Gly Ala Gly Ser Gly Ala Gly Ala Gly Ser Gly Ala Gly Ala Gly
                690                 695                 700
Ser Gly Ala Gly Ala Gly Ser Gly Ala Gly Ala Gly Ser Gly Val Gly
705                 710                 715                 720
Val Pro Gly Val Gly Val Pro Gly Val Gly Val Pro Gly Val Gly Val
                725                 730                 735
Pro Gly Lys Gly Val Pro Gly Val Gly Val Pro Gly Val Gly Val Pro
                740                 745                 750
Gly Val Gly Val Pro Gly Ala Gly Ala Gly Ser Gly Ala Gly Ala Gly
                755                 760                 765
Ser Gly Ala Gly Ala Gly Ser Gly Ala Gly Ala Gly Ser Gly Ala Gly
                770                 775                 780
Ala Gly Ser Gly Ala Gly Ala Gly Ser Gly Val Gly Val Pro Gly Val
785                 790                 795                 800
Gly Val Pro Gly Val Gly Val Pro Gly Val Gly Val Pro Gly Lys Gly
                805                 810                 815
Val Pro Gly Val Gly Val Pro Gly Val Gly Val Pro Gly Val Gly Val
                820                 825                 830
Pro Gly Ala Gly Ala Gly Ser Gly Ala Gly Ala Gly Ser Gly Ala Gly
                835                 840                 845
Ala Gly Ser Gly Ala Gly Ala Gly Ser Gly Ala Gly Ala Gly Ser Gly
                850                 855                 860
Ala Gly Ala Gly Ser Gly Val Gly Val Pro Gly Val Gly Val Pro Gly
865                 870                 875                 880
Val Gly Val Pro Gly Val Gly Val Pro Gly Lys Gly Val Pro Gly Val
                885                 890                 895
Gly Val Pro Gly Val Gly Val Pro Gly Val Gly Val Pro Gly Ala Gly
                900                 905                 910
Ala Gly Ser Gly Ala Gly Ala Gly Ser Gly Ala Gly Ala Gly Ser Gly
                915                 920                 925
Ala Gly Ala Gly Ser Gly Ala Gly Ala Gly Ser Gly Ala Gly Ala Gly
                930                 935                 940
Ser Gly Val Gly Val Pro Gly Val Gly Val Pro Gly Val Gly Val Pro
945                 950                 955                 960
Gly Val Gly Val Pro Gly Lys Gly Val Pro Gly Val Gly Val Pro Gly
                965                 970                 975
Val Gly Val Pro Gly Val Gly Val Pro Gly Ala Gly Ala Gly Ser Gly
                980                 985                 990
Ala Gly Ala Gly Ser Gly Ala Gly Ala Gly Ser Gly Ala Gly Ala Gly
                995                1000                1005
Ser Gly Ala Gly Ala Gly Ser Gly Ala Gly Ala Gly Ser Met Asp Pro
                1010                1015                1020
Gly Arg Tyr Gln Asp Leu Arg Ser His His His His His His
1025                1030                1035

<210> 31
<211> 965
<212> PRT
<213> Unknown

<220>
<223> SELP 58

<400> 31

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
                20                  25                  30

FIGURE 4P

```
Met Gly Val Gly Val Pro Gly Val Gly Val Pro Gly Val Gly Val Pro
         35              40              45
Gly Val Gly Val Pro Gly Val Gly Val Pro Gly Val Gly Val Pro Gly
 50              55              60
Val Gly Val Pro Gly Val Gly Val Pro Gly Ala Gly Ala Gly Ser Gly
 65              70              75                          80
Ala Gly Ala Gly Ser Gly Ala Gly Ala Gly Ser Gly Ala Gly Ala Gly
             85              90                          95
Ser Gly Ala Gly Ala Gly Ser Gly Val Gly Val Pro Gly Val Gly Val
             100             105             110
Pro Gly Val Gly Val Pro Gly Val Gly Val Pro Gly Val Gly Val Pro
         115             120             125
Gly Val Gly Val Pro Gly Val Gly Val Pro Gly Val Gly Val Pro Gly
 130             135             140
Ala Gly Ala Gly Ser Gly Ala Gly Ala Gly Ser Gly Ala Gly Ala Gly
 145             150             155                         160
Ser Gly Ala Gly Ala Gly Ser Gly Ala Gly Ala Gly Ser Gly Val Gly
             165             170             175
Val Pro Gly Val Gly Val Pro Gly Val Gly Val Pro Gly Val Gly Val
             180             185             190
Pro Gly Val Gly Val Pro Gly Val Gly Val Pro Gly Val Gly Val Pro
         195             200             205
Gly Val Gly Val Pro Gly Ala Gly Ala Gly Ser Gly Ala Gly Ala Gly
         210             215             220
Ser Gly Ala Gly Ala Gly Ser Gly Ala Gly Ala Gly Ser Gly Ala Gly
 225             230             235                         240
Ala Gly Ser Gly Val Gly Val Pro Gly Val Gly Val Pro Gly Val Gly
             245             250             255
Val Pro Gly Val Gly Val Pro Gly Val Gly Val Pro Gly Val Gly Val
             260             265             270
Pro Gly Val Gly Val Pro Gly Val Gly Val Pro Gly Ala Gly Ala Gly
         275             280             285
Ser Gly Ala Gly Ala Gly Ser Gly Ala Gly Ala Gly Ser Gly Ala Gly
 290             295             300
Ala Gly Ser Gly Ala Gly Ala Gly Ser Gly Val Gly Val Pro Gly Val
 305             310             315                         320
Gly Val Pro Gly Val Gly Val Pro Gly Val Gly Val Pro Gly Val Gly
             325             330             335
Val Pro Gly Val Gly Val Pro Gly Val Gly Val Pro Gly Val Gly Val
             340             345             350
Pro Gly Ala Gly Ala Gly Ser Gly Ala Gly Ala Gly Ser Gly Ala Gly
         355             360             365
Ala Gly Ser Gly Ala Gly Ala Gly Ser Gly Ala Gly Ala Gly Ser Gly
 370             375             380
Val Gly Val Pro Gly Val Gly Val Pro Gly Val Gly Val Pro Gly Val
 385             390             395                         400
Gly Val Pro Gly Val Gly Val Pro Gly Val Gly Val Pro Gly Val Gly
             405             410             415
Val Pro Gly Val Gly Val Pro Gly Ala Gly Ala Gly Ser Gly Ala Gly
             420             425             430
Ala Gly Ser Gly Ala Gly Ala Gly Ser Gly Ala Gly Ala Gly Ser Gly
 435             440             445
Ala Gly Ala Gly Ser Gly Val Gly Val Pro Gly Val Gly Val Pro Gly
 450             455             460
Val Gly Val Pro Gly Val Gly Val Pro Gly Val Gly Val Pro Gly Val
 465             470             475                         480
Gly Val Pro Gly Val Gly Val Pro Gly Val Gly Val Pro Gly Ala Gly
             485             490             495
Ala Gly Ser Gly Ala Gly Ala Gly Ser Gly Ala Gly Ala Gly Ser Gly
             500             505             510
Ala Gly Ala Gly Ser Gly Ala Gly Ala Gly Ser Gly Val Gly Val Pro
         515             520             525
Gly Val Gly Val Pro Gly Val Gly Val Pro Gly Val Gly Val Pro Gly
         530             535             540
Val Gly Val Pro Gly Val Gly Val Pro Gly Val Gly Val Pro Gly Val
```

FIGURE 4Q

```
545                      550                      555                      560
Gly Val Pro Gly Ala Gly Ala Gly Ser Gly Ala Gly Ala Gly Ser Gly
                    565                      570                      575
Ala Gly Ala Gly Ser Gly Ala Gly Ala Gly Ser Gly Ala Gly Ala Gly
                    580                      585                      590
Ser Gly Val Gly Val Pro Gly Val Gly Val Pro Gly Val Gly Val Pro
                    595                      600                      605
Gly Val Gly Val Pro Gly Val Gly Val Pro Gly Val Gly Val Pro Gly
    610                      615                      620
Val Gly Val Pro Gly Val Gly Val Pro Gly Ala Gly Ala Gly Ser Gly
625                      630                      635                      640
Ala Gly Ala Gly Ser Gly Ala Gly Ala Gly Ser Gly Ala Gly Ala Gly
                    645                      650                      655
Ser Gly Ala Gly Ala Gly Ser Gly Val Gly Val Pro Gly Val Gly Val
                    660                      665                      670
Pro Gly Val Gly Val Pro Gly Val Gly Val Pro Gly Val Gly Val Pro
                    675                      680                      685
Gly Val Gly Val Pro Gly Val Gly Val Pro Gly Val Gly Val Pro Gly
    690                      695                      700
Ala Gly Ala Gly Ser Gly Ala Gly Ala Gly Ser Gly Ala Gly Ala Gly
705                      710                      715                      720
Ser Gly Ala Gly Ala Gly Ser Gly Ala Gly Ala Gly Ser Gly Val Gly
                    725                      730                      735
Val Pro Gly Val Gly Val Pro Gly Val Gly Val Pro Gly Val Gly Val
                    740                      745                      750
Pro Gly Val Gly Val Pro Gly Val Gly Val Pro Gly Val Gly Val Pro
                    755                      760                      765
Gly Val Gly Val Pro Gly Ala Gly Ala Gly Ser Gly Ala Gly Ala Gly
    770                      775                      780
Ser Gly Ala Gly Ala Gly Ser Gly Ala Gly Ala Gly Ser Gly Ala Gly
785                      790                      795                      800
Ala Gly Ser Gly Val Gly Val Pro Gly Val Gly Val Pro Gly Val Gly
                    805                      810                      815
Val Pro Gly Val Gly Val Pro Gly Val Gly Val Pro Gly Val Gly Val
                    820                      825                      830
Pro Gly Val Gly Val Pro Gly Val Gly Val Pro Gly Ala Gly Ala Gly
                    835                      840                      845
Ser Gly Ala Gly Ala Gly Ser Gly Ala Gly Ala Gly Ser Gly Ala Gly
    850                      855                      860
Ala Gly Ser Gly Ala Gly Ala Gly Ser Gly Val Gly Val Pro Gly Val
865                      870                      875                      880
Gly Val Pro Gly Val Gly Val Pro Gly Val Gly Val Pro Gly Val Gly
                    885                      890                      895
Val Pro Gly Val Gly Val Pro Gly Val Gly Val Pro Gly Val Gly Val
                    900                      905                      910
Pro Gly Ala Gly Ala Gly Ser Gly Ala Gly Ala Gly Ser Gly Ala Gly
                    915                      920                      925
Ala Gly Ser Gly Ala Gly Ala Gly Ser Gly Ala Gly Ala Gly Ser Met
    930                      935                      940
Asp Pro Gly Arg Tyr Gln Leu Ser Ala Gly Arg Tyr His Tyr Gln Leu
945                      950                      955                      960
Val Trp Cys Gln Lys
                    965
```

USE OF REPEAT SEQUENCE PROTEIN POLYMERS IN PERSONAL CARE COMPOSITIONS

CROSS-REFERENCE TO RELATED APPLICATIONS

This application is a Continuation of U.S. patent application Ser. No. 10/939,036, filed Sep. 10, 2004 now abandoned, which claims priority to Continuation-in-Part of U.S. patent application Ser. No. 10/800,179, filed Mar. 12, 2004 now U.S. Pat. No. 7,297,678, which claims priority under 35 U.S.C. §119 of U.S. Provisional Application Ser. No. 60/454,077 filed Mar. 12, 2003.

FIELD OF THE INVENTION

The present invention provides personal care compositions, and more particularly, personal care compositions comprising a bioactively effective amount of a repeat sequence protein polymer. In some particularly preferred embodiments, the present invention provides personal care compositions comprising an effective amount of at least one fragment of a repeat sequence protein polymer having bioactivity.

BACKGROUND OF THE INVENTION

Proteins have been widely used as ingredients in personal care products, pigment coating, and in bandages to promote wound healing. Use of silk proteins to perform a variety of functions and to impart desired characteristics to product formulations has been described (See e.g., U.S. Pat. No. 5,747,015; Japanese Patent No. 27186; and Japanese Patent No. 309816). In these disclosures, silk protein hydrolysates were used because of the low solubility of intact silk proteins. For example, for these reasons, proteins have been used to impart some beneficial coating effects such as manageability and strength to hair, to moisturize skin and hair, and to provide film formation to improve the appearance of skin and hair. Proteins have also been used to provide durability properties to many personal care products.

However, such proteins may not exhibit all desired characteristics when used in personal care products. For example, natural silk proteins may impart durability but may also form tight, hard fibers that are not suitable for film formation. Also, many natural proteins have a low isoelectric point, which reduces the affinity of the protein for the negatively charged skin and hair. Additionally, when more than one protein is needed to impart all desired characteristics to a given formulation, the necessity of using more than one protein may increase the cost and production time for a given personal care product.

Furthermore, proteins generally have poor solubility due to high molecular weight and hydrophobicity. Commercially available proteins, including structural proteins such as silk and collagen, are typically chemically degraded giving a diverse mixture of molecular weight fragments with variable properties (See e.g., German Patent No. 3139438; and U.S. Pat. No. 6,280,747). However, in most embodiments, hydrolyzed proteins have not been found to be as effective as the intact proteins, as the beneficial effects of the self-assembly, nanofibrilation and coating properties have not realized. As such, these proteins are often modified chemically (See e.g. U.S. Pat. No. 6,296,860) to enhance solubility for inclusion in personal care products and coating pigments for personal care use (See e.g. U.S. Pat. No. 4,325,741). However, even chemically modified proteins may not have all desired characteristics.

In addition, in the wound care area, enzymatically digested silk protein has been described as being useful as a healing promoter in wound dressings (See e.g. U.S. Pat. No. 5,382,431). However, digested silk protein is not as effective as water-soluble silk protein (See e.g., WO 04/044172). U.S. Pat. No. 6,175,053 describes the use of dissolved silk proteins as a wound dressing material. However, these preparations required harsh solvents to dissolve the silk protein prior to use.

Thus, there remains a need in the art for personal care compositions that have desired characteristics without undesirable chemical modification of the proteins. There also remains a need in the art for a method of delivering a protein into a personal care composition so as to effectively deliver the protein in a useable form.

SUMMARY OF THE INVENTION

The present invention provides to personal care compositions, and more particularly, personal care compositions comprising a bioactively effective amount of a repeat sequence protein polymer. In some particularly preferred embodiments, the present invention provides personal care compositions comprising an effective amount of at least one fragment of a repeat sequence protein polymer having bioactivity.

In some embodiments, the present invention is directed to personal care compositions comprising an effective amount of at least one repeat sequence protein polymer. In one embodiment, the repeat sequence polymer comprises a repeating amino acid sequence unit derived from elastin, collagen, abductin, byssus, flagelliform silk, dragline silk, gluten high molecular weight subunit, titin, fibronectin, leminin, gliadin, glue polypolypeptide, ice nucleating protein, keratin mucin, RNA polymerase II, resalin or a mixture thereof.

In another embodiment of the of the invention, the repeat sequence protein polymer (RSPP) formula comprises:

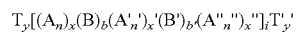

$$T_y[(A_n)_x(B)_b(A'_{n'})_{x'}(B')_{b'}(A''_{n''})_{x''}]_i T'_{y'}$$

wherein: T and T' each comprise an amino acid sequence of from about 1 to about 100 amino acids, wherein the amino acid sequence of T' is the same as or different from the amino acid sequence of T; y and y' are each an integer from 0 to 1, wherein the integer of y' is the same as or different from the integer of y; A, A' and A'' are each individual repeating amino acid sequence units comprising from about 3 to about 30 amino acids, wherein the amino acid sequence of A' and the amino acid sequence of A'' are the same as or different from the amino acid sequence of A; n, n', and n'' are each integers of at least 2 and not more than 250; x, x' and x'' are each 0 or an integer of at least 1, wherein each integer varies to provide for at least 30 amino acids in the A', A' and A'' individual amino acid sequence repeating units, and wherein the integer of x' and the integer of x'' are the same as or different from the integer of x; B and B'each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 100.

In alternative embodiments, the present invention provides bioactive protein polymers, which show efficacy in cell viability improvement, elastin biosynthesis, collagen biosynthesis, and inhibition of skin metelloprotease MMP1 activity.

The present invention further provides personal care compositions comprising an effective amount of a repeat sequence protein polymer (RSPP) or a fragment thereof, and a physiologically acceptable carrier or excipient, wherein the repeat sequence protein polymer provides at least one cosmetic benefit.

In some most preferred embodiments, the present invention provides personal care compositions comprising an effective amount of a repeat sequence protein polymer or a fragment thereof, and a physiologically acceptable carrier or excipient, wherein the repeat sequence protein polymer provides improved skin tone.

In some particularly preferred embodiments, the present invention provides personal care compositions comprising an effective amount of a repeat sequence protein polymer or a fragment thereof, and a physiologically acceptable carrier or excipient, wherein the repeat sequence protein polymer increases skin fibroblast viability.

In alternative preferred embodiments, the present invention provides personal care compositions comprising an effective amount of a repeat sequence protein polymer or a fragment thereof, and a physiologically acceptable carrier or excipient, wherein the repeat sequence protein polymer stimulates synthesis of collagen.

In further preferred embodiments, the present invention provides personal care compositions comprising an effective amount of a repeat sequence protein polymer or a fragment thereof, and a physiologically acceptable carrier or excipient, wherein the repeat sequence protein polymer stimulates synthesis of elastin.

In additional preferred embodiments, the present invention provides personal care compositions comprising an effective amount of a repeat sequence protein polymer or a fragment thereof, and a physiologically acceptable carrier or excipient, wherein the repeat sequence protein polymer inhibits MMP1 activity.

In still further preferred embodiments, the present invention provides personal care compositions comprising an effective amount of a repeat sequence protein polymer or a fragment thereof, and a physiologically acceptable carrier or excipient, wherein the repeat sequence protein polymer inhibits elastase activity.

In some embodiments, the repeat sequence protein polymer comprises from about 0.001 weight % to about 10 weight % of the composition, while in other embodiments, the repeat sequence protein polymer comprises from about 0.01 weight % to about 5 weight % of the composition, and in still further embodiments, the repeat sequence protein polymer comprises from about 0.01 weight % to about 1 weight % of the composition.

In some embodiments of the present invention, the RSPP fragment is less than 20 amino acids, while in further embodiments, the fragment comprises an amino acid sequence with fewer than 20% of the total number of amino acids in the repeat sequence protein polymer. In additional embodiments, the RSPP fragment comprises a repeating amino acid sequence with a further biological or chemical function or activity. In some particularly preferred embodiments, the fragment comprises at least a portion of the sequence set forth in SEQ ID NOS: 25, 26, 27, 28, 30, 31, 32, 34, and 36. In further more particularly preferred embodiments, the fragment comprises a portion of SEQ ID NO: 19.

In some embodiments, the RSPP fragment comprises from about 0.001 weight % to about 10 weight % of the composition, while in other embodiments, the RSPP fragment comprises from about 0.01 weight % to about 5 weight % of the composition, and in still other embodiments, the fragment comprises from about 0.01 weight % to about 1 weight % of the composition.

In additional embodiments, the personal care compositions of the present invention are skin care compositions selected from moisturizing body washes, body washes, antimicrobial cleansers, skin protective creams, body lotions, facial creams, moisturizing creams, facial cleansing emulsions, surfactant-based facial cleansers, facial exfoliating gels, anti-acne treatments, facial toners, exfoliating creams, facial masks, after shave balms and radioprotectives.

In some embodiments, the personal care composition are skin care compositions comprising topically applied over-the-counter compositions, anti-fungal treatments, anti-acne treatments, skin protectants, and antiperspirants.

In further embodiments, the personal care compositions are makeup compositions. In some preferred embodiments, the makeup compositions are selected from eye gels, high-melting point lipsticks, lipsticks, lip glosses, lip balms, mascaras, eyeliners, pressed powder formulations, and foundations. In some particularly preferred embodiments, the skin care compositions are radioprotective. In some more particularly preferred embodiments, the radioprotective is a sunscreen selected from non-water-resistant sunscreens, very water-resistant sunscreens, and water-in-silicone sunscreens.

In further embodiments, the makeup compositions of the present invention comprise at least one pigment. In some preferred embodiments, the makeup compositions comprising at least one pigment are mascaras selected from non-waterproof mascaras, waterproof mascaras, volumizing mascaras, lengthening mascaras, curling mascaras, anhydrous waterproof mascaras, water-based mascaras, and eyelash or eyebrow treatment.

In further embodiments, the makeup compositions are pressed powder formulations selected from loose powders, blushes, eye shadows, and bronzing powders. In still additional embodiments, the makeup compositions are foundations selected from water-in-oil foundations, water-in-silicone foundations, oil-in-water foundations, anhydrous makeup sticks, and cream-to-powder foundations.

In some particularly preferred embodiments, the present invention provides personal care compositions comprising an effective amount of a repeat sequence protein polymer or a fragment thereof, with the balance of the composition comprising one or more compounds from the group of carriers, excipients, liposomes, active ingredients, biological or botanical products, humectants, emollients, surfactants, thickening agents, silicone components, organic sunscreens, preservatives, neutralizing agents, perfumes or pigments, and wherein the repeat sequence protein polymer or fragment thereof improves or enhances skin tone.

The present invention also provides methods for making personal care compositions comprising combining an effective amount of a repeat sequence protein polymer fragment or a fragment thereof, with a physiologically acceptable carrier or excipient to provide a personal care composition.

In some embodiments, these methods further comprise combining a compound from the group of carriers, excipients, liposomes, active ingredients, humectants, emollients, surfactants, thickening agents, silicone components, organic sunscreens, preservatives, neutralizing agents, perfumes or pigments to the composition.

The present invention also provides methods for protecting skin from environmental damage comprising the steps of: providing skin to be exposed to environmental damage; providing a composition comprising a repeat sequence protein polymer or at least one fragment of a repeat sequence protein polymer; and applying the composition to the skin. In some embodiments, the environmental damage comprises damage due to exposure to radiation. In further embodiments, the radiation comprises ultraviolet light. In still other embodiments, the environmental damage comprises damage due to exposure to chemicals or free radicals. In some particularly preferred embodiments, the repeat sequence protein polymer comprises SELP47K. In additional particularly preferred embodiment, the repeat sequence protein polymer comprises SEQ ID NO: 19.

In accordance with another embodiment of the present invention, the personal care composition comprises a hair care composition, a skin care composition, a nail care composition, a cosmetic composition, an over-the-counter pharmaceutical composition, or a combination thereof.

The personal care compositions comprising an effective amount of a repeat sequence protein polymer are advantageous in providing personal care products that have desired characteristic(s) without chemical modifications of the protein. These characteristics include but are not limited to, transparent film formation, hydrogel formation, better efficacy and binding to skin, hair, nail and oral surfaces, desired level of hydrophobicity with water solubility, imparting luster, softness, moisture retainment, mechanical properties (such as tensile properties, viscoelastic behavior, glass transition temperature, cloud temperature, and decomposition temperature). Still other advantages of the present invention will become apparent to those skilled in the art from the following detailed description where alternative exemplary embodiments of this invention are shown and described. As will be realized, the invention is capable of other different, obvious aspects and embodiments, all without departing from the invention. Accordingly, the drawings and descriptions should be regarded as illustrative in nature and not as restrictive.

DESCRIPTION OF THE FIGURES

FIG. 4 provides the sequences for SEQ ID NOS: 1-31.

DESCRIPTION OF THE INVENTION

Figure 1:
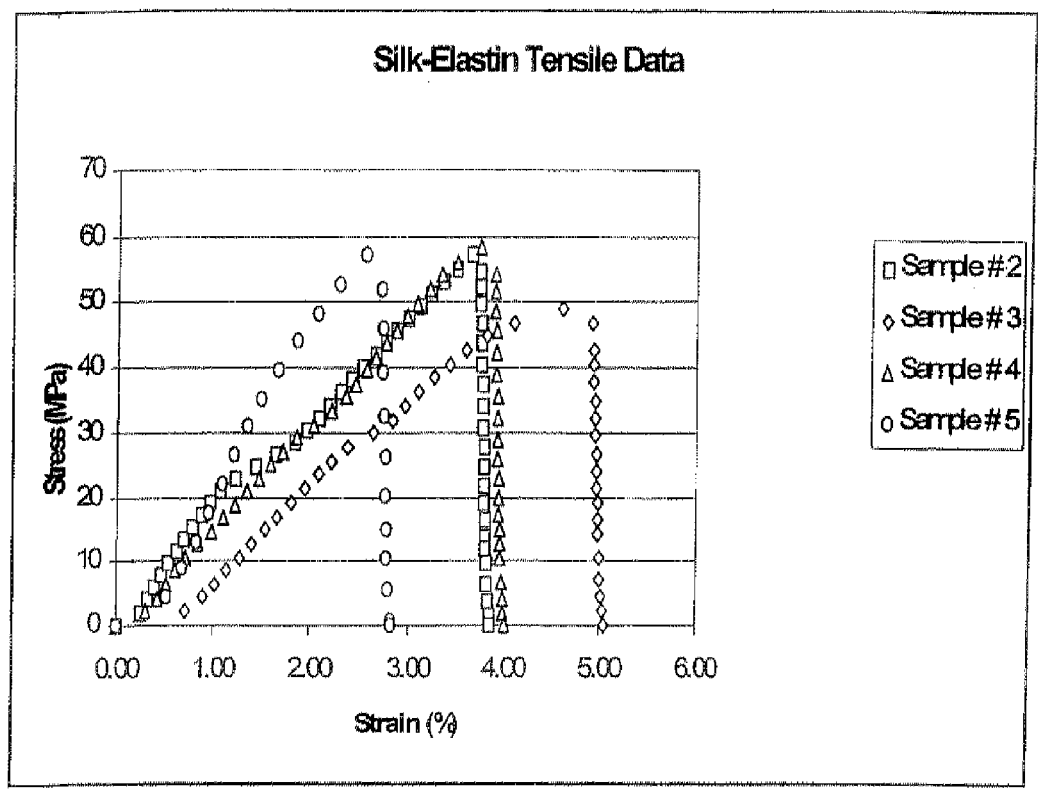
FIG. 1 is a chart illustrating stress strain curves of a repeat protein polymer in accordance with an embodiment of the present invention.

The present invention provides personal care compositions, and more particularly, personal care compositions comprising a bioactively effective amount of a repeat sequence protein polymer. In particularly preferred embodiments, the present invention provides personal care compositions comprising an effective amount of at least one fragment of a repeat sequence protein polymer having bioactivity.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biolog,* 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. To facilitate understanding of the invention, a number of terms are defined below.

As used herein, the term "repeat sequence protein polymer" (RSPP) refers to a polymer comprising repeating amino acid sequence units, wherein the repeating units are derived from a natural or synthetic protein. For example, in some embodiments, the repeating sequence units are derived from natural structure supporting materials such as silk, elastin, and collagen. In alternative embodiments, the repeating sequence units are derived from synthetic structures. In some particularly preferred embodiments, the RSPP is SELP47K, while in other preferred embodiments, the RSPP is a variant of SELP47K, while in still further preferred embodiments, the RSPP is a portion of SELP47K (e.g., monomeric SELP47K).

As used herein, the term "multimer" refers to a portion of the repeat sequence protein polymer. In preferred embodiments, "multimer" refers to a portion of the repeat sequence protein polymer represented by $[(A_n)_x(B)_b(A'_n)_x(B')_b'(A''_n'')_x'']_i$ in the formula $T_y[(A_n)_x(B)_b(A'_n)_x(B')_b'(A''_n'')_x'']_iT'_{y'}$, described in greater detail in the

DETAILED DESCRIPTION OF THE INVENTION

As used herein, "the spacing between repeating sequence units" refers to the other amino acid sequences represented by B or B' in the above formula. In some embodiments, the copolymers are combinations of silk units and elastin units, which provides silk-elastin copolymers having properties distinctive from polymers having only the same monomeric unit.

A "variant" of an RSPP (e.g., SELP) as used herein, refers to an amino acid sequence that is altered by one or more amino acids. The variant may have "conservative" changes, wherein a substituted amino acid has similar structural or chemical properties, (e.g. replacement of leucine with isoleucine). More rarely, a variant may have "nonconservative" changes (e.g., replacement of a glycine with a tryptophan). Similar minor variations may also include amino acid deletions or insertions, or both. In addition to the teaching herein, guidance in determining which amino acid residues may be substituted, inserted, or deleted without abolishing bioactivity may be found using computer programs well known in the art, for example, DNASTAR software.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "amino acid sequence" refers to an amino acid sequence of a naturally occurring protein molecule. "Amino acid sequence" and like terms, such as "polypeptide" and "protein" are not meant to limit the amino acid sequence to the complete, native amino acid sequence associated with the recited protein molecule.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus encodes the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," refer to a nucleic acid sequence comprising the coding region of a gene (i.e., the nucleic acid sequence which encodes a gene product). The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample.

A compound is said to be "in a form suitable for administration" when the compound may be administered to a human or other animal by any desired route (e.g. topical, oral, etc.). A "composition comprising a given polynucleotide sequence" as used herein refers broadly to any composition containing the given polynucleotide sequence. The composition may comprise an aqueous solution. Compositions comprising polynucleotide sequences encoding SELP47K (e.g., SEQ ID NO: 19), variants (e.g., the variants listed in Table 2), or fragments (e.g., monomeric SELP47K) thereof find use in various embodiments of the present invention.

As used herein, "monodispersed" polymers refers to polymers that have a single defined molecular weight.

As used herein, "polydispersed" polymers refers to polymers that have been subjected to proteolysis or other means of subdivision, and have a distribution of molecular weights.

As used herein, the term "personal care composition" refers to a product for application to the skin, hair, nails, oral cavity and related membranes for the purposes of improving, cleaning, beautifying, treating, and/or caring for these surfaces and membranes.

As used herein, "cosmetic composition" refers to compositions that find use in the cosmetics. The Food Drug and Cosmetic Act (FD&C Act) definition is used herein. Thus, cosmetics are defined by their intended use, as articles intended to be rubbed, poured, sprinkled, or sprayed on, introduced into, or otherwise applied to the human body for cleansing, beautifying, promoting attractiveness, or altering appearance. These compositions provide non-therapeutic benefits and are not regulated as pharmaceuticals. However, in some situations, cosmetic compositions are incorporated into pharmaceutical compositions to provide cosmetic benefits (e.g., products that treat skin or hair diseases, but also contain cosmetic compositions for their coloring or other benefits). Also, it is intended that the present invention encompass the use of cosmetics on animals other than humans.

As used herein, the terms "pharmaceutical compositions" and "therapeutic compositions" refer to compositions such as drugs that provide medical benefits, rather than solely cosmetic benefits. In the United States, pharmaceutical and therapeutic compositions are approved by the Food and Drug Administration for treatment and/or prevention of particular conditions.

As used herein, the term "drug" is defined as it is in the FD&C Act definition. Thus, drugs are defined as articles intended for use in the diagnosis, cure, mitigation, treatment or prevention of disease, and articles (other than food) intended to affect the structure or any function of the body of man or other animals.

As used herein, the term "cosmetic benefit" refers to a desired cosmetic change that results from the administration of a personal care composition. Cosmetic benefits include but are not limited to improvements in the condition of skin, hair, nails, and the oral cavity. In preferred embodiments, at least one cosmetic benefit is provided by the skin care, hair care, nail care, and makeup compositions of the present invention.

As used herein, "skin care composition" refers to compositions that are applied to skin in order to provide beneficial properties, including but not limited to wrinkle minimizing, wrinkle removal, decoloring, coloring, skin softening, skin smoothing, dipilation, cleansing, etc. In some particularly preferred embodiments, the present invention provides skin care compositions that improve skin tone. In these embodiments, the improvement comprises lessening of wrinkles, smoothing skin texture, modifying skin coloration, and other desired cosmetic benefits.

As used herein, "hair care composition" refers to compositions that are applied to hair to provide beneficial properties such as thickening, thinning, coloring, decoloring, cleansing, conditioning, softening, shaping, etc.

As used herein "nail care composition" refers to compositions that are applied to the nails to provide beneficial properties such as harder and stronger nails, nail color, etc.

As used herein, "makeup compositions" refer to cosmetic preparations that are used to beautify, caring for, maintaining, or augment the appearance of a human or other animal. "Makeup compositions" include, but are not limited to color cosmetics, such as mascaras, lipsticks, lip liners, eye shadows, eye-liners, rouges, face powders, foundations, blushes, and nail polish.

As used herein, the term "an effective amount" refers to the amount of repeat sequence protein polymer, which is added to a personal care composition to provide the composition with a desired characteristic(s).

As used herein, the term "bioactivity" refers to a cause and effect relationship between a composition and a biological system. Thus, the term is used as by those skilled in the art of biotechnology and biological sciences as the phrase that describes a cause and effect relationship between a molecular composition and living biological matter (e.g., tissue, cells, etc.).

As used herein as a noun, the term "bioactive" refers a composition that exhibits bioactivity upon administration to living biological matter (e.g., tissue, cells, etc.). The term is used synonymously with "bioactive compound."

As used herein, the term "dispersed phase" is used as by those of skill in the art of emulsion technology as the phase that exists as small particles or droplets suspended in and surrounded by a continuous phase. The dispersed phase is also known as the "internal" or "discontinuous" phase.

As used herein, "penetration enhancers" refer to compositions that facilitate penetration through the upper stratum corneum barrier to the deeper skin layers. Examples of penetration enhancers include, but are not limited to, propylene glycol, azone, ethoxydiglycol, dimethyl isosorbide, urea, ethanol, dimethyl sulfoxide, microemulsions, liposomes, and nanoemulsions.

As used herein, the terms "emulsifier" and "surfactant" refer to compounds that disperse and suspend the dispersed phase within the continuous phase of a material. Surfactants find particular use in products intended for skin and/or hair cleansing. In particular embodiments, the term "surfactant(s)" is used in reference to surface-active agents, whether used as emulsifiers or for other surfactant purposes such as skin cleansing.

DETAILED DESCRIPTION OF THE INVENTION

The present invention provides personal care compositions, and more particularly, personal care compositions comprising a bioactively effective amount of a repeat sequence protein polymer. In some particularly preferred embodiments, the present invention provides personal care compositions comprising an effective amount of at least one fragment of a repeat sequence protein polymer having bioactivity.

Those skilled in the art appreciate the various naturally occurring proteins containing repeating sequence units which can be used for producing the repeat sequence protein polymers of the present invention, any of which may be employed herein. More specifically, there are more than six hundred repeating amino acid sequence units known to exist in biological systems. For example, well known proteins containing repeating amino acid sequence units include abductin, elastin, byssus, flagelliform silk, dragline silk, gluten high molecular weight (HMW) subunit, titin, fibronectin, leminin, and collagen.

Individual repeating amino acid sequence units of particular interest include units found in silk-, elastin-, collagen-, abductin-, byssus-, gluten-, titin-, extensin-, and fibronectin-like proteins. Silk-like proteins comprise a repeating sequence unit SGAGAG (SEQ ID NO:1). This repeating sequence unit is found in naturally occurring silk fibroin protein, which can be represented as GAGAG(SGAGAG)$_8$SGAAGY (SEQ ID NO:2). Elastin-like proteins comprise a base repeating sequence unit of GVGVP (SEQ ID NO:3). This repeating sequence unit may be found in naturally occurring elastin. Collagen-like proteins comprise a repeating sequence unit of G-X-X$^1$, wherein X comprises any amino acid, often alanine or proline; and X$^1$ comprises any amino acid, often proline or hydroxy-proline (SEQ ID NO:20). In one embodiment, collagen-like protein comprises SEQ ID NO:29. Abductin-like proteins comprise a base repeating sequence unit of GGFGGMGGGX, wherein X comprises any amino acid (SEQ ID NO:4). Byssus-like proteins comprise a repeating sequence unit of GPGGG (SEQ ID NO:5). Gluten-like proteins of the high molecular weight subunit comprise repeating sequence units of PGQGQQ (SEQ ID NO:6), GYYPTSPQQ (SEQ ID NO:7), and GQQ (SEQ ID NO:8). Titin-like proteins comprise repeating sequence units of PPAKVPEVPKKPVPEEKVPVPVPKKPEA (SEQ ID NO:9), which proteins may be found in the heart, psoas, and soleus muscle. Extensin-like proteins comprise repeating sequence units of SPPPPSPKYVYK (SEQ ID NO:10). Fibronectin-like proteins comprise repeating sequence units of RGDS (SEQ ID NO:11). Additional repeating sequence units are found, for example, in gliadin, glue polypolypeptide, ice nucleating protein, keratin, mucin, RNA polymerase II, and resilin. Gliadin comprises a repeating sequence unit of PQQPY (SEQ ID NO:12). The glue polypeptide comprises a repeating sequence unit of PTTTK (SEQ ID NO:13). The ice nucleating protein comprises a repeating sequence unit of AGYGSTGT (SEQ ID NO:14). Keratin comprises repeating sequence units of YGGSSGGG (SEQ ID NO:15) or FGGGS (SEQ ID NO:16). Mucin comprises a repeating sequence unit of TTTPDV (SEQ ID NO:17). RNA polymerase II comprises a repeating sequence unit of YSPTSPS (SEQ ID NO:18).

In addition to repeating units derived from naturally occurring proteins, synthetic repeating amino acid sequences units may be utilized. In a particular embodiment, the repeat sequence protein polymer has the formula:

$$T_y[(A_n)_x(B)_b(A'_{n'})_{x'}(B'')_{b'}(A''_{n''})_{x''}]_i T'_{y'}$$

wherein:

T and T' each comprise an amino acid sequence of from about 1 to about 100 amino acids, specifically an amino acid sequence of from about 1 to about 60 amino acids, and more specifically an amino acid sequence with fewer than 20% of the total number of amino acids in the repeat sequence protein polymer, wherein the amino acid sequence of T' is the same as or different from the amino acid sequence of T;

y and y' are each an integer from 0 to 1, wherein the integer of y' is the same as or different from the integer of y;

A, A' and A" are each individual repeating sequence units comprising from about 3 to about 30 amino acids, wherein the amino acid sequence of A' and the amino acid sequence of A" are the same as or different from the amino acid sequence of A;

n, n', and n" are each integers of at least 2 and not more than 250;

x, x' and x" are each 0 or an integer of at least 1, wherein each integer varies to provide for at least 30 amino acids in the A', A' and A" individual repeating sequence units, and wherein the integer of x' and the integer of x" are the same as or different from the integer of x;

B and B' each comprise an amino acid sequence of from about 4 to about 50 amino acids, wherein the amino sequence of B' is the same as or different from the amino acid sequence of B;

b and b' are each an integer from 0 to 3, wherein the integer of b' is the same as or different from the integer of b; and i is an integer from 1 to 100, specifically from 1 to 50, and more specifically from 1 to 30.

Additionally, in some embodiments, the repeat sequence protein polymer comprises amino acid sequences that link the repeating A, A', and A" units or amino acid sequences that link between the individual A, A' or A" repeating sequence units. In some preferred embodiments, the linking sequences are from about 1 to about 10 amino acids.

Those skilled in the art appreciate the various methods for producing the repeat sequence protein polymers of the present invention, any of which may be employed herein. For example, the repeat sequence protein polymer may be produced by generally recognized methods of chemical synthesis (See e.g., Andersson et. al., Biopolymers 55:227-50 [2000]); genetic manipulation (See e.g., Cappello, *Genetically Engineered Protein Polymers, In Handbook of Biodegradable Polymers*, Domb et al. (eds), Harvard Academic Publishers, Amsterdam; pages 387-414), and enzymatic synthesis (See e.g. Wong and Wang, Experientia 47:1123-9 [1991]). Furthermore, in other embodiments, the repeat sequence protein polymers of the present invention are produced using the methods described in U.S. Pat. Nos. 5,243,038 and 6,355,776, the disclosures of which are incorporated by reference herein. In yet additional embodiments, the repeat sequence protein polymers are produced utilizing non-ribosomal peptide synthase (See e.g., Dohren et al., Chem. Rev., 97:2675-2705 [1997]). In some particularly preferred embodiments, the repeat sequence protein polymers are produced on a commercial scale.

In some embodiments, the repeating amino acid sequence units comprise identical repeating sequence units, while in other embodiments, they comprise different repeating sequence unit combinations, which join together to form a block copolymer or an alternating block copolymer. Additionally, in some embodiments, the individual repeating amino acid sequence units of the repeat sequence protein polymer comprise from about 3 to about 30 amino acids. In other embodiments, the individual repeating units comprise from about 3 to about 8 amino acids. Moreover, the same amino acid may appear at least twice in the same repeating sequence unit. Thus, it is not intended that the amino acids be limited as to the number of repeats in each repeating sequence unit.

Repeat sequence protein polymers utilizing natural and/or synthetic repeating sequence units are produced to provide various desirable characteristics. One skilled in the art appreciates the various desirable characteristics for repeat sequence protein polymers, any of which may be employed herein. The characteristics may include, for example, moisturizing properties, adhesion, contraction, entrapment, high glass transition temperature for hardness or strength, a high cloud temperature for heat sensitive applications, and/or a high isoelectric point to increase the affinity of the protein to hair, skin, and nails, etc. Self-assembly and nanofilament formation properties find use in skin anti-wrinkle and fine line filling applications. Additionally, in some embodiments, a protein having a particular molecular weight is chosen in order to increase or decrease water solubility and/or other properties as desired.

Furthermore, repeat sequence protein polymers are advantageous in providing personal care products when modified with desired chemical agents. RSPPs provide amino, hydroxyl and/or carboxyl functional groups that can be covalently reacted, conjugated, composited or ionically bonded with various personal care chemical and formulating functional ingredients. In various embodiments, these include: UV absorbers (e.g., octyl methoxycinnamate, benzophenone-3, titanium dioxide, and octyl salicylate); film-forming agents (e.g., VP/Eicosene copolymer); cosmeceutical agents (e.g., peptides and proteins, alpha hydroxy acids, and retinol and retinoic acid derivatives); antioxidants (e.g., tocopherol and derivatives thereof and ascorbic acid and derivatives thereof); vitamins (e.g., B, D, K and their derivatives); antiperspirant actives (e.g., aluminum hydroxide and zirconium hydroxide); depilating agents (e.g., thioglycolate salts); anti-acne agents (e.g., salicylic acid and benzoyl peroxide); abrasives and exfoliants (e.g., silicates, pumice, and polyethylene); and extracts of plant, fruit, vegetable and/or marine sources.

It will also be understood by those having skill in the art that in some embodiments, the synthetic repeat sequence protein polymers are produced to have a combination of desirable characteristics. For example, in some embodiments, a copolymer comprising silk repeating sequence units and elastin repeating sequence units is synthesized to impart durability due to the silk repeating sequence units and to impart flexibility due to the elastin repeating sequence units. In additional embodiments, the silk-elastin polymer exhibits other desirable properties such as good clear film and hydrogel formation, which the individual monomeric units may not exhibit. In further embodiments, the silk elastin copolymer is hydrophilic and water-soluble. In yet additional embodiments, the silk elastin copolymer exhibits a high cloud temperature which is desirable in heat sensitive applications. In yet further embodiments, the silk elastin copolymer has a high isoelectric point, which in some embodiments, makes the copolymer more substantive to skin and hair. In additional embodiments, the silk elastin copolymer further exhibits self-assembly into fibers and films, which is desirable in some applications.

The desired properties of the repeating sequence units are designed to produce the desired characteristics by choosing the particular repeating amino acid sequence units, the number of repeating sequence units in each multimer, the spacing between the repeating sequence units, and the number of repeats of the multimer.

It will be further understood by those having skill in the art that the repeat sequence protein polymers of the present invention may be monodispersed or polydispersed, as desired.

In accordance with some embodiments of the present invention, a silk-elastin polymer SELP47K (SEQ ID NO: 19) finds use as a repeat sequence protein polymer of the present invention. The SELP47K is a homoblock protein polymer that consists exclusively of silk-like crystalline blocks and elastin-like flexible blocks. SELP47K is more linear than many proteins because it has a beta sheet two-dimensional structure rather than an alpha helix three-dimensional structure. SELP47K exhibits the ability to self-assemble by cross-linking of beta sheets into fibers. SELP47K is 70% proline, valine, and alanine, and has hydrophobic characteristics. Additionally, SELP47K has a high lysine ratio. In additional embodiments, the repeat sequence protein polymer comprises SELP 47-E13 (SEQ ID NO:25), SELP 47R-3 (SEQ ID NO:26), SELP 47K-3 (SEQ ID NO:27), SELP 47 E-3 (SEQ ID NO:28), SELP 67K (SEQ ID NO:30), and/or SELP 58 (SEQ ID NO:31), SELP47K-P4 (SEQ ID NO:32), DCP6 (SEQ ID NO:34).

In some preferred embodiments, once a suitable repeat sequence protein polymer is been synthesized and purified, an effective amount is added to personal care composition(s) that find use in personal care products. Personal care products can be classified/described as cosmetic, over-the-counter ("OTC") compounds that find use in personal care applications (e.g., cosmetics, skin care, oral care, hair care, nail care). In some embodiments, the repeat sequence protein polymer is added to a personal care composition such as a hair care composition, a skin care composition, a nail care composition, a cosmetic composition, or any combinations thereof.

In some embodiments, the hair care composition is in a form selected from the group consisting of shampoos, conditioners, anti-dandruff treatments, styling aids, styling conditioners, hair repair or treatment sera, lotions, creams, pomades, and chemical treatments. In other embodiments, the styling aids are selected from the group consisting of sprays, mousses, rinses, gels, foams, and combinations thereof. In further embodiments, the chemical treatments are selected from the group consisting of permanent waves, relaxers, and permanents, semi-permanents, temporary color treatments and combinations thereof. In further embodiments, the skin care composition is in a form selected from the group consisting of body washes, moisturizing body washes, deodorant body washes, antimicrobial cleansers, skin protecting treatments, body lotions, facial creams, moisturizing creams, facial cleansing emulsions, surfactant-based facial cleansers, facial exfoliating gels, facial toners, exfoliating creams, facial masks, after shave lotions, balms, and/or radioprotective compositions (e.g., sunscreens).

In other embodiments, the cosmetic composition is in a form selected from the group consisting of eye gels, eye shadows, high-melting point lipsticks, lipsticks, lip glosses, lip balms, mascara, brow liners, eyeliners, pressed powder formulations, foundations, protein coated pigments, and combinations thereof In further embodiments, the cosmetic compositions comprise makeup compositions. In yet another embodiment, the nail care composition is in a form selected from the group consisting of nail enamel, cuticle treatment, nail polish, nail treatment, and polish remover. In yet another embodiment, the oral care composition is in a form selected from the group consisting of toothpaste, mouth rinse, breath freshener, whitening treatment, and inert carrier substrates. In yet another embodiment, the over-the-counter composition comprises radioprotectives (e.g., sunscreens), anti-acne, antiperspirants, skin protectants, anti-dandruff products, anti-fungal, hemorrhoidal ointments, and toothpaste.

In further embodiments, the personal care composition is in the form of an emulsified vehicle, such as a nutrient cream or lotion, a stabilized gel or dispersioning system, such as skin softener, a nutrient emulsion, a nutrient cream, a massage cream, a treatment serum, a liposomal delivery system, a topical facial pack or mask, a surfactant-based cleansing system such as a shampoo or body wash, an aerosolized or sprayed dispersion or emulsion, a hair or skin conditioner, styling aid, or a pigmented product such as makeup in liquid, cream, solid, anhydrous or pencil form.

In some preferred embodiments, the repeat sequence protein polymer SELP47K finds use in personal care compositions. Specifically, SELP47K finds used in hair care products, as it is contemplated to provide such benefits as building body and/or volume, repair of damaged hair, and/or protection of hair from chemical damage. In additional embodiments, SELP47K has applications in skin care products, as it is contemplated to provide various benefits such as tightening or firming of the skin, moisturization, improved skin tone, oil absorption, and/or improvement in the appearance of fine lines and wrinkles. It is further contemplated that SELP47K will find use in various make-up products, in particular to provide eyelash flexibility, volume, length, and strength.

In some embodiments, the repeat sequence protein polymer comprises from about 0.001% to about 10% by weight of the personal care composition. In other embodiments, the repeat sequence protein polymer comprises from about 0.01% to about 5% by weight of the personal care composition. In yet other embodiments, the repeat sequence protein polymer comprises from about 0.01% to about 1% by weight of the personal care composition.

In some embodiments, the personal care composition comprising an effective amount of a repeat sequence protein polymer, as set forth herein, comprises additional components. For example, in some embodiments, the personal care compositions of the present invention comprise liposomes, wherein the liposomes comprise components such as water and one or more ingredients capable of forming lipid bilayer vesicles that can hold one or more functional or active ingredient(s). Non-limiting examples of ingredients capable of forming lipid bilayer vesicles include: phospholipids, hydrogenated phosphatidylcholine, lecithin, cholesterol and sphingolipids. Non-limiting examples of functional or active ingredients that can be delivered from liposomes include: vitamins and their derivatives, antioxidants, proteins and peptides, keratolytic agents, bioflavinoids, terpenoids, phytochemicals, and extracts of plant, marine or fermented origin. In some embodiments, liposomes include, without limitation: a) lipoid liposome 0003 (composed of water and lecithin and glycerin); b) lipoid liposome 0300 (composed of water and phosphatidylcholine), c) lipoid liposome 0111 (composed of water, ginkgo balboa leaf extract, denatured alcohol, hydrogenated lecithin and cholesterol) d) anti-irritant liposomes (composed of water, cola acuminata seed extract, bisabolol and phospholipids), e) vitamin C and E liposomes (composed of water, phospholipids, tocopheryl acetate and ascorbyl palmitate), f) firming liposomes (composed of water, butylene glycol, pyrus malus (apple) fruit extract, phospholipids, tocopheryl acetate and carbomer) and g) moisturizing liposomes (composed of water, sodium PCA, tocopheryl acetate, xanthan gum, arginine, lysine, glycine and proline).

In other embodiments, the personal care composition of the present invention further comprise at least one active ingredient. There are numerous active ingredients known to those of skill in the art that find use in the personal care compositions of the present invention. Indeed, it is contemplated that any suitable active ingredient or combination of suitable active ingredients will find use in the present invention (See e.g. McCutcheon's *Functional Materials*, North American and International Editions, published by MC Publishing Co. [2003]). For example, in some embodiments, the personal care compositions herein comprise a skin care active ingredient at a level from about 0.0001% to about 20%, by weight of the composition. In another embodiment, the personal care compositions comprise a skin care active ingredient from about 0.001% to about 5%, by weight of the composition. In yet another embodiment, the personal care compositions comprise a skin care active ingredient from about 0.01% to about 2%, by weight of the composition.

Suitable skin care active ingredients include, but are not limited to, antioxidants (e.g., tocopheryl and ascorbyl derivatives); bioflavinoids, terpenoids, synthetics of biolflavinoids and terpenoids and the like; vitamins and vitamin derivatives; hydroxyl- and polyhydroxy acids and their derivatives (e.g. AHAs and BHAs and their reaction products); peptides and polypeptides and their derivatives (e.g., glycopeptides and lipophilized peptides, heat shock proteins and cytokines); enzymes and enzymes inhibitors and their derivatives (e.g., proteases, MMP inhibitors, catalases, CoEnzyme Q10, glucose oxidase and superoxide dismutase (SOD)); amino acids and their derivatives; bacterial, fungal and yeast fermentation products and their derivatives (e.g. mushrooms, algae and seaweed and their derivatives); phytosterols and plant and plant part extracts; phospholipids and their derivatives; anti-dandruff agents (e.g., zinc pyrithione); and sunscreen agents (e.g., ethylhexyl methoxycinnamate, avobenzone, and phenyl benzimidazole sulfonic acid). Delivery systems comprising the active ingredients are also provided herein.

In some embodiments, the skin care active ingredient is selected from the group consisting of a Vitamin B3 component, panthenol, Vitamin E, Vitamin E acetate, retinoid, retinol, retinyl, propionate, retinyl palmitate, retinoic acid, Vitamin C, theobromine, alpha-hydroxyacid, farnesol, phytrantriol, salicylic acid, palmityl peptapeptide-3 and mixtures thereof. In other embodiments, the Vitamin B3 compound is niacinamide. In yet other embodiments, the vitamin $B_3$ compound is tocopherol nicotinate. Exemplary derivatives of the foregoing vitamin $B_3$ compounds include nicotinic acid esters (e.g., non-vasodilating esters of nicotinic acid, nicotinyl amino acids, nicotinyl alcohol esters of carboxylic acids, and nicotinic acid N-oxide and niacinamide N-oxide). Suitable esters of nicotinic acid include nicotinic acid esters of $C_1$-$C_{22}$, specifically $C_1$-$C_{16}$, more specifically $C_1$-$C_6$ alcohols. The alcohols are suitably straight-chain or branched chain, cyclic or acyclic, saturated or unsaturated (including aromatic), and substituted or unsubstituted. The esters are specifically non-vasodilating. Non-vasodilating esters of nicotinic acid include tocopherol nicotinate and inositol hexanicotinate. Although these compounds are well known to those in the art, a more complete description of vitamin $B_3$ compounds is provided by WO 98/22085.

In some embodiments, the retinoid skin care active ingredient is selected from the group consisting of retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid). These compounds are well known in the art and are commercially available from a number of sources (e.g., Sigma-Aldrich Chemical Company, and Boehringer Mannheim). Exemplary retinoids include retinol, retinyl palmitate, retinyl acetate, retinyl proprionate, retinal, retinoic propionate, retinoic acid and combinations thereof. In some embodiments, the retinoid is included as a substantially pure material, while in other embodiments, it is an extract obtained by suitable physical and/or chemical isolation from natural (e.g., plant) sources. In some embodiments, the retinoid comprises from about 0.005% to about 2% and more preferably from about 0.01% to about 12% by weight of the personal care composition. In other embodiments, the personal care composition comprises retinol. In some preferred embodiments, the retinol comprises from about 0.01% to about 0.15% by weight of the personal care composition. In yet other embodiments, the personal care composition comprise retinol esters. In some preferred embodiments, the retinol esters comprise from about 0.01% to about 2% by weight of the personal care composition.

In addition to the active ingredients noted above, in some embodiments, the personal care composition comprise a physiologically acceptable carrier and/or excipient. In some particularly preferred embodiments, the personal care compositions herein comprise a safe and effective amount of at least one dermatologically acceptable carrier suitable for topical application to the skin, nails, mucous membranes, and/or hair within which the essential materials and optional other materials are incorporated to enable the essential materials and optional components to be delivered to the site of application (i.e., the target site) at an appropriate concentration. Thus, the carrier acts as a diluent, dispersant, solvent or the like for the essential components which ensures that they can be applied to and distributed evenly over the selected target site at an appropriate concentration.

In some embodiments, as indicated above, an effective amount of one or more compounds described herein also includes personal care compositions suitable for application to keratinous materials such as nails and hair, including but not limited to those useful as hair spray compositions, hair styling compositions, hair shampooing and/or conditioning compositions, compositions applied for the purpose of hair growth regulation and compositions applied to the hair and scalp for the purpose of treating seborrhoea, dermatitis and/or dandruff.

In some embodiments, an effective amount of one or more compounds described herein included in personal care compositions suitable for topical application to the skin, teeth, nails or hair. In some embodiments, these compositions are in the form of creams, lotions, gels, suspensions dispersions, microemulsions, nanodispersions, microspheres, hydrogels, emulsions (e.g., oil-in-water and water-in-oil, as well as multiple emulsions) and multilaminar gels and the like (See e.g. Schlossman et al., *The Chemistry and Manufacture of Cosmetics*, [1998]). In some embodiments, these compositions are formulated as aqueous or silicone compositions, while in other embodiments they are formulated as emulsions of one or more oil phases in an aqueous continuous phase, and is still further embodiments, are an aqueous phase in an oil phase.

The type of carrier utilized in the present invention depends on the type of product form desired for the personal care composition. In some embodiments, the carrier is a solid, while in other embodiments, it is semi-solid or liquid. Suitable carriers include liquids, as well as semi-solids (e.g., creams, lotions, gels, sticks, ointments, pastes, sprays and mousses). In particular, carriers that are lotions, creams or gels have sufficient thickness or yield find use in the present invention, as they prevent the particles from sedimenting. In some embodiments, the carrier itself is inert, while in other embodiments, it possesses dermatological benefits of its own. In some embodiments, the carrier is applied directly to the teeth, skin, nails and/or hair, while in other embodiments, it is applied via a woven or non-woven wipe or cloth. In alternative embodiments, it is provided as a patch, mask, wrap, or another inert substrate. In yet further embodiments, the carrier is aerosolized or otherwise sprayed or pumped onto the skin and/or hair. In preferred embodiments, the carrier is physically and chemically compatible with the essential components described herein, and does not unduly impair stability, efficacy or other use benefits associated with the compositions of the present invention.

In some embodiments of the present invention, the carrier is selected from the group consisting of water, propylene glycol, ethanol, propanol, glycerol, butylene glycol, and polyethylene glycol, as well as any suitable combination thereof. In further embodiments, the carriers also contain at least one dermatologically acceptable, hydrophilic diluent. Suitable hydrophilic diluents include water, organic hydrophilic diluents (e.g., $C_2$-$C_{10}$, specifically $C_2$-$C_6$, more specifically, $C_3$-$C_6$ monohydric alcohols) and low molecular weight glycols and polyols (e.g. propylene glycol, polyethylene glycol polypropylene glycol, glycerol, butylene glycol, 1,2,4-butanetriol, sorbitol, 1,2,6-hexametriol, pentylene glycol, hexylene glycol, sorbitol esters, ethoxylated ethers, propoxylated ethers) and combinations thereof. In one embodiment, the diluent is a liquid. In one preferred embodiment, the diluent is water. In another embodiment, the personal care composition comprises at least about 20% of the hydrophilic diluent.

In some embodiments, suitable carriers also comprise an emulsion comprising a hydrophilic phase, especially an aqueous phase, and a hydrophobic phase (e.g., a lipid, oil or oily material). As well known to those skilled in the art, the hydrophilic phase is dispersed in the hydrophobic phase, or vice versa, to form respectively hydrophilic or hydrophobic dispersed and continuous phases, depending on the composition of ingredients. In some embodiments, the emulsion comprises an oil-in-water emulsion or a water-in-oil emulsion such as a water-in-silicone emulsion (e.g., in a triple or other multi-phase emulsion). In some preferred embodiments, oil-in-water emulsions comprise from about 1% to about 60% or from about 1% to about 30% of the dispersed hydrophobic phase, and from about 1% to about 99% or from about 10% to about 90% of the continuous hydrophilic phase, while in some alternative embodiments, water-in-oil emulsions comprise from about 1% to about 98%, or from about 40% to about 90% of the dispersed hydrophilic phase and from about 1% to about 50% or from about 1% to about 30% of the continuous hydrophobic phase.

In some embodiments, the carrier also includes one or more components that facilitate penetration through the upper stratum corneum barrier to the deeper skin layers. Examples of penetration enhancers include, but are not limited to, propylene glycol, azone, ethoxydiglycol, dimethyl isosorbide, urea, ethanol, dimethyl sulfoxide, microemulsions, liposomes and nanoemulsions. However, it is intended that any suitable penetration enhancer will find use in the present invention.

In some embodiments, the personal care compositions of the present invention further comprise humectants. In some of these embodiments, the personal care composition comprises from about 0.01% to about 20% by weight of humectant. In other embodiments, the personal care composition comprises from about 0.1% to about 15% by weight of a humectant. In yet other embodiments, the personal care composition comprises from about 0.5% to about 10% by weight of a humectant. Humectants that find use in the present invention include, but are not limited to, compounds selected from polyhydric alcohols, sorbitol, glycerol, urea, betaine, D or DL panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6,-triol, guanidine or its derivatives, and mixtures thereof. However, it is intended that any suitable humectant will find use in the present invention.

Examples of suitable polyhydric alcohol humectants for use herein include polyalkylene glycols and specifically alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. In some embodiments, polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Additional suitable humectants useful herein include sodium 2-pyrrolidone-5-carboxylate (NaPCA), guanidine, glycolic acid, glycolate salts (e.g., ammonium and quaternary alkyl ammonium), lactic acid, lactate salts (e.g., ammonium and quaternary alkyl ammonium), aloe vera in any of its variety of forms (e.g., aloe vera gel), hyaluronic acid and derivatives thereof (e.g., salt derivatives such as sodium hyaluronate), lactamide monoethanolamine, acetamide monoethanolamine, urea, betaine, panthenol and derivatives thereof, and mixtures thereof.

In some embodiments, at least part (up to about 5% by weight of composition) of a humectant is incorporated in the form of an admixture with a particulate cross-linked hydrophobic acrylate or methacrylate copolymer, itself specifically present in an amount of from about 0.1% to about 10%, which can be added either to the aqueous or disperse phase. As known in the art (See e.g., WO96/03964), this copolymer is particularly valuable for reducing shine and controlling oil, while helping to provide effective moisturization benefits.

In some preferred embodiments, the oil-in-water and oil-in-water-in-oil emulsion embodiments of the present invention comprise from about 0.05% to about 20%, specifically from about 1% to about 15%, more specifically from about 2% to about 10%, and even more specifically from about 2% to about 5% by weight of a dermatologically acceptable emollient. Emollients tend to lubricate the skin, increase the smoothness and suppleness of the skin, prevent or relieve dryness of the skin and/or protect the skin. Emollients are typically water-immiscible, oily or waxy materials and emollients with high molecular weights can confer aesthetic properties to a topical composition. A wide variety of suitable emollients are known and find use herein. As known in the art (See, Sagarin, *Cosmetics, Science and Technology,* 2nd Edition, Vol. 1, pp. 32-43 [1972]; and WO 00/24372), numerous materials find use as emollients. Thus, it is intended that any suitable emollient will find use in the present invention. However, some preferred examples are outlined in further detail below:

i) Straight and branched chain hydrocarbons having from about 7 to about 40 carbon atoms, such as mineral oils, dodecane, squalane, cholesterol, hydrogenated polyisobutylene, isohexadecane, isoeicosane, isooctahexacontane, isohexapentacontahectane, and the $C_7$-$C_{40}$ isoparaffins, which are $C_7$-$C_{40}$ branched hydrocarbons. Suitable branched chain hydrocarbons for use herein are selected from isopentacontaoctactane, petrolatum and mixtures thereof, ii) $C_1$-$C_{30}$ fatty acid esters of $C_1$-$C_{30}$ carboxylic acids, $C_{12-15}$ 12-15 alkyl benzoates and of $C_2$-$C_{30}$ dicarboxylic acids, such as isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof, iii) $C_1$-$C_{30}$ mono- and poly-esters of sugars and related materials derived from a sugar or polyol moiety and one or more carboxylic acid moieties. Depending on the constituent acid and sugar, these esters are either liquid or solid form at room temperature. Examples include glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester. Other materials include cottonseed oil or soybean oil fatty acid esters of sucrose. Other examples of such materials are described in WO 96/16636;

iv) Vegetable oils and hydrogenated vegetable oils. Examples of vegetable oils and hydrogenated vegetable oils include safflower oil, grapeseed oil, coconut oil, cottonseed oil, menhaden oil, palm kernel oil, palm oil, peanut oil, soybean oil, rapeseed oil, linseed oil, rice bran oil, pine oil, nut oil, sesame oil, sunflower seed oil, partially and fully hydrogenated oils from the foregoing sources and mixtures thereof, and v) Soluble or colloidally-soluble moisturizing agents. Examples include hyaluronic acid and, chondroitin sulfate, heparan sulfate, and starch-grafted sodium polyacrylates.

In further embodiments, personal care compositions of the present invention also contain one or more emulsifiers and/or surfactants, generally to help disperse and suspend the disperse phase within the continuous phase. Surfactants find particular use in products intended for skin and/or hair cleansing. Known and/or conventionally used surfactants (See e.g., WO 00/24372) find use in the personal care compositions of the present invention, provided that the selected agent is chemically and physically compatible with essential components of the composition and provides the desired characteristics. Suitable surfactants include non-silicone derived materials, silicone-derived materials, and mixtures thereof. In some embodiments, the personal care compositions of the present invention comprise from about 0.05% to about 30%, preferably from about 0.5% to 15%, and more preferably from about 1% to 10% by weight of a surfactant or mixture of surfactants. As known to those skilled in the art, the exact surfactant or surfactant mixture chosen will depend upon the pH of the composition, the other components present and the desired final product aesthetics.

Among the nonionic surfactants that are useful herein are those that can be broadly defined as condensation products of long chain alcohols (e.g., $C_{8-30}$ alcohols, with sugar or starch polymers, such as glycosides). Other useful nonionic surfactants include the condensation products of alkylene oxides with fatty acids (i.e., alkylene oxide esters of fatty acids). These materials have the general formula $RCO(X)_nOH$ wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from 6 to 200. Other nonionic surfactants are the condensation products of alkylene oxides with 2 moles of fatty acids (i.e., alkylene oxide diesters of fatty acids). These materials have the general formula $RCO(X)_nOOCR$ wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from 6 to 100. For example, an emulsifier for use herein is most specifically a fatty acid ester blend based on a mixture of sorbitan fatty acid ester and sucrose fatty acid ester, more specifically a blend of sorbitan stearate and sucrose cocoate. Even further suitable examples include a mixture of cetearyl alcohols and cetearyl glucosides.

Hydrophilic surfactants useful herein can alternatively or additionally include any of a wide variety of cationic, anionic, zwitterionic, and amphoteric surfactants such as those known in the art (See, e.g., McCutcheon's, *Detergents and Emulsifiers and Detergents*, North American [2003], and International Editions [1986], published by MC Publishing Co. and Allured Publishing Corporation; and U.S. Pat. Nos. 5,011, 681, 4,421,769, and 3,755,560, herein incorporated by reference).

A variety of anionic surfactants are known in the art (See e.g., U.S. Pat. No. 3,929,678, herein incorporated by reference) also find use in the personal care compositions of the present invention. Examples of anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., substituted alkylamine and alkali metal salts, such as sodium or potassium salts) of fatty acids.

Amphoteric and zwitterionic surfactants are find use in some embodiments of the personal care compositions of the present invention. Examples of amphoteric and zwitterionic surfactants which find use in the compositions of the present invention include those that are broadly described as derivatives of aliphatic secondary and tertiary amines in which the aliphatic radical can be straight or branched chain and wherein one of the aliphatic substituents contains from about 8 to about 22 carbon atoms (specifically $C_8$-$C_{18}$) and one contains an anionic water solubilizing group (e.g., carboxy, sulfonate, sulfate, phosphate, or phosphonate). Examples include alkyl imino acetates and iminodialkanoates and aminoalkanoates, imidazolinium and ammonium derivatives. Other suitable amphoteric and zwitterionic surfactants include those selected from the group consisting of betaines, sultaines, hydroxysultaines, and branched and unbranched alkanoyl sarcosinates, and mixtures thereof.

In some embodiments of the present invention, personal care composition emulsions include a silicone containing emulsifier or surfactant. A wide variety of silicone emulsifiers find use herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains and polyether chains containing moieties derived from both ethylene oxide and propylene oxide. Other examples include alkyl-modified dimethicone copolyols (i.e., compounds which contain $C_2$-$C_{30}$ pendant side chains). Still other useful dimethicone copolyols include materials having various cationic, anionic, amphoteric, and zwitterionic pendant moieties.

In further embodiments, the personal care compositions of the present invention contain at least one polymeric thickening agent. The polymeric thickening agents useful herein may have a number average molecular weight of greater than about 20,000, preferably greater than about 50,000, and more preferably greater than about 100,000. In some embodiments, the personal care compositions of the present invention comprise from about 0.01% to about 10%, preferably from about 0.1% to about 8%, and more preferably from about 0.25% to about 5% by weight of a polymeric thickening agent, or mixtures thereof.

Examples of polymer thickening agents for use herein include non-ionic thickening agents and anionic thickening agents or mixtures thereof. Suitable non-ionic thickening agents include polyacrylamide polymers, crosslinked poly (N-vinylpyrrolidones), polysaccharides, natural or synthetic gums, polyvinylpyrrolidone and polyvinylalcohol. Suitable anionic thickening agents include acrylic acid/ethyl acrylate copolymers, carboxyvinyl polymers and crosslinked copolymers of alkyl vinyl ethers and maleic anhydride. As an example, Noveon sells a thickener under the trademark of CARBOPOL™ resins or mixtures thereof In some embodiments, suitable CARBOPOL™ resins are hydrophobically modified, while in other embodiments, suitable resins include those described in WO98/22085, or mixtures thereof.

In some embodiments, the personal care compositions of the present invention comprise at least one silicone oil phase. Silicone oil phase(s) generally comprise(s) from about 0.1% to about 20%, preferably from about 0.5% to about 10%, and more preferably from about 0.5% to about 5% by weight of the composition. In some embodiments, the silicone oil phase comprises one silicone component, while in alternative embodiments, the silicone oil phase comprises more than one silicone component.

In some embodiments, silicone components are fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. In some embodiments, the silicone fluids are volatile, while in other embodiments, the silicone fluids are non-volatile. Silicone fluids generally have an average molecular weight of less than about 200,000. Suitable silicone fluids have a molecular weight of about 100,000 or less, preferably about 50,000 or less, and more preferably about 10,000 or less. In particularly preferred embodiments, the silicone fluid used in the present invention is selected from silicone fluids having a weight average molecular weight in the range from about 100 to about 50,000 and most preferably from about 200 to about 40,000.

Typically, silicone fluids that find use in the present invention have a viscosity ranging from about 0.65 to about 600,000 $mm^2s^{-1}$, and preferably from about 0.65 to about 10,000 $mm^2s^{-1}$ at 25° C. The viscosity can be measured by means of a glass capillary viscometer as set forth in Dow Corning Corporate Test Method CTM0004, Jul. 29, 1970. Suitable polydimethyl siloxanes that find use in the present invention include commercially available compounds (e.g., from General Electric Company and Dow Corning). In additional embodiments, essentially non-volatile polyalkylarylsiloxanes (e.g., polymethylphenylsiloxanes, having viscosities of about 0.65 to 30,000 $mm^2s^{-1}$ at 25° C.; available from General Electric Company and Dow Corning) find use in the present invention. Cyclic polydimethylsiloxanes suitable for use herein preferably have a ring structure incorporating from about 3 to about 7 $(CH_3)_2SiO$ moieties, and preferably about 5 or more.

In some embodiments, silicone gums find use in the personal care compositions of the present invention. In some specific embodiments, a silicone oil phase comprises a silicone gum or a mixture of silicones including the silicone gum. Typically, silicone gums have a viscosity at 25° C. in excess of about 1,000,000 $mm^2s^{-1}$. Silicone gums that find use in the present invention include dimethicones (e.g., those described in U.S. Pat. No. 4,152,416, herein incorporated by reference; Noll, *Chemistry and Technology of Silicones* Academic Press, New York [1968]; and General Electric Silicone Rubber Product Data Sheets SE 30, SE 33, SE 54 and SE 76). Specific examples of silicone gums include polydimethylsiloxane, (polydimethylsiloxane)(methylvinylsiloxane) copolymer, poly(dimethylsiloxane)-(diphenyl)(methylvinylsiloxane) copolymer and mixtures thereof. Preferred silicone gums for use herein include silicone gums having a molecular weight of from about 200,000 to about 4,000,000 selected from dimethiconol, dimethicone copolyol, dimethicone and mixtures thereof.

In some embodiments, the silicone phase herein comprises a silicone gum incorporated into the composition as part of a silicone gum-fluid blend. In some embodiments in which the silicone gum is incorporated as part of a silicone gum-fluid blend, the silicone gum constitutes from about 5% to about 40%, and preferably from about 10% to 20% by weight of the silicone gum-fluid blend. Suitable silicone gum-fluid blends herein are mixtures consisting essentially of:

(i) a silicone having a molecular weight of from about 200,000 to about 4,000,000 selected from dimethiconol, fluorosilicone and dimethicone and mixtures thereof, and (ii) a carrier which is a silicone fluid, the carrier having a viscosity from about 0.65 $mm^2s^{-1}$ to about 100 $mm^2s^{-1}$, wherein the ratio of i) to ii) is from about 10:90 to about 20:80, and wherein said silicone gum-based component has a final viscosity of from about 100 $mm^2s^{-1}$ to about 100,000 $mm^2s^{-1}$, and more preferably from 500 $mm^2s^{-1}$ to about 10,000 $mm^2s^{-1}$.

Additional silicone components suitable for use in the silicone oil phase of some embodiments of the present invention include crosslinked polyorganosiloxane polymers, including those that are dispersed in a fluid carrier. In general, the crosslinked polyorganosiloxane polymers, together with their carrier (if present) comprise from about 0.1% to about 20%, preferably from about 0.5% to about 10%, and more preferably from about 0.5% to about 5% by weight of the personal care composition. Suitable polymers include those comprising polyorganosiloxane polymers crosslinked by a crosslinking agent (See, WO98/22085). Examples of suitable polyorganosiloxane polymers for use herein include methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment (See e.g., WO98/22085). Suitable polydiorganosiloxane-polyalkylene copolymers are available commercially under the tradename BELSIL™ from Wacker-Chemie GmbH. An example of a copolymer fluid blend for use herein includes Dow Corning DC3225C which has the CTFA designation Dimethicone/Dimethicone copolyol.

In some embodiments, personal care compositions of the present invention also comprise at least one organic sunscreen. In some embodiments, suitable radioprotectives (e.g., sunscreens) exhibit UVA-absorbing properties and/or UVB-absorbing properties. The exact amount of the sunscreen active will vary, depending upon the desired Sun Protection Factor ("SPF") of the composition, as well as the desired level of UV protection. SPF is a commonly used indicator of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen may comprise from about 2% to about 20%, and preferably from about 4% to about 14% by weight of the personal care composition. Suitable sunscreens include, but are not limited to, those approved for use in the United States, Japan, Europe and Australia. In preferred embodiments, the compositions of the present invention comprise an SPF of about 2 to about 30, preferably about 4 about 30, and more preferably about 4 to about 15.

In some embodiments, the personal care compositions of the present invention include one or more UVA absorbing sunscreen actives that absorb UV radiation having a wavelength of from about 320 nm to about 400 nm. Suitable UVA absorbing sunscreen actives include those selected from dibenzoylmethane derivatives (See e.g., Lowe and Shaath (eds.), Sunscreens: Development Evaluation and Regulatory Aspects, Marcel Dekker, Inc [1990]), anthranilate derivatives (e.g., methylanthranilate and homomethyl, 1-N-acetylanthranilate), and mixtures thereof. In some embodiments, the UVA absorbing sunscreen active is present in an amount suitable to provide broad spectrum UVA protection either independently, or in combination with, any other UV protective actives present in the composition.

Suitable UVA sunscreen actives include dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'methoxydibenzoylmethane, and mixtures thereof. In one embodiment, the dibenzoyl sunscreen actives include those selected from 4-(1,1-dimethylethyl)-4'-methoxydibenzoylmethane, 4-isopropyldibenzoylmethane, and mixtures thereof. In further embodiments, the sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or avobenzone, is commercially available under the names of PARSOL® 1789 (Givaudan Roure (International) S.A.), and EUSOLEXQ® 9020 (Merck & Co., Inc). The sunscreen 4-isoproplydibenzoylmethane, which is also known as isopropyldibenzoylmethane, is commercially available from Merck under the name of EUSOLEX® 8020.

In some embodiments, the personal care compositions of the present invention further include one or more UVB sunscreen actives that absorb UV radiation having a wavelength of from about 290 nm to about 320 nm. The compositions comprise an amount of the UVB sunscreen active that is safe and effective in providing UVB protection either independently, or in combination with, any other UV protective actives present in the compositions. In some embodiments, the compositions comprise from about 0.1% to about 20%, preferably from about 0.1% to about 12%, and more preferably from about 0.5% to about 8% by weight of each UVB absorbing organic sunscreen, or as mandated by any relevant regulatory authority.

A variety of UVB sunscreen actives find use in the present invention, including, but not limited to organic sunscreen actives described in U.S. Pat. Nos. 5,087,372, 5,073,371, and 5,073,372, all of which are incorporated herein by reference. Additional sunscreens that find use in the present invention include those described in U.S. Pat. Nos. 4,937,370 and 4,999,186, both of which are incorporated herein by reference. Preferred UVB sunscreen actives are selected from 2-ethylhexyl-2-cyano-3,2-ethylhexyl N,N-dimethyl-p-aminobenzoate, p-amino-benzoic acid, oxybenzone, homomenthyl salicylate, octyl salicylate, 4,4'-methoxy-1-butyldibenzoylmethane, 4-isopropyl dibenzoylmethane, 3-benzylidene camphor, 3-(4-methylbenzylidene)camphor, 3-diphenylacrylate, 2-phenyl-benzimidazole-5-sulphonic acid (PBSA), cinnamate esters and their derivatives such as 2-ethylhexyl-p-methoxycinnamate and octyl-p-methoxycinnamate, salicylate esters and their derivatives such as TEA triethanolamine salicylate, ethylhexyl saliycyilate, octyldimethyl para-aminobenzoic acid PABA, camphor derivatives and their derivatives, and mixtures thereof Examples of organic sunscreen actives include 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also find use herein.

In additional embodiments, at least one agent is added to the personal care compositions of the present invention to stabilize the UVA sunscreen(s) to prevent photo-degradation upon exposure to UV radiation, thereby maintaining UVA protection efficacy. A wide range of compounds are known to provide these stabilizing properties and should be chosen to complement both the UVA sunscreen and the composition as a whole. Suitable stabilizing agents include, but are not limited to, those described in WO 00/06110, and U.S. Pat. Nos. 5,972,316, 5,968,485, 5,935,556, 5,827,508, all of which are incorporated by reference. Examples of stabilizing agents for use in the present invention include 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl)acrylate, diethylhexyl 2,6 napthalate and mixtures thereof (Symrise Chemical Company).

In further embodiments, at least one agent is added to any of the personal care compositions of the present invention to improve the skin substantivity of those compositions, particularly to enhance their resistance to being washed off by water or rubbed off. Examples include, but are not limited to, acrylates/$C_{12-22}$ alkylmethacrylate copolymer, acrylate/acrylate copolymer, dimethicone, dimethiconol, graft-copoly (dimethylsiloxane/iI-butyl methacrylate), lauryl dimethicone, PVP/Hexadecane copolymer, PVP/Eicosene copolymer, tricontanyl PVP and trimethoxysiloxysiliacate.

In addition to organic sunscreens, some embodiments of personal care compositions of the present invention additionally comprise inorganic physical sunblocks, as known in the art (See e.g., CTFA International Cosmetic Ingredient Dictionary, $6^{th}$ Edition, [1995], pp. 1026-28 and 1103; Sayre et al., J. Soc. Cosmet. Chem., 41:103-109 [1990]; and Lowe et al., supra). In some particularly preferred embodiments, inorganic physical sunblocks such as zinc oxide and/or titanium dioxide, and mixtures thereof find use in the present invention.

In some particularly preferred embodiments of the present invention, physical sunblocks are present in an amount such that the present compositions are transparent on the skin (i.e., non-whitening), from about 0.5% to about 20%, preferably from about 0.51% to about 10%, and more preferably from about 0.5% to 5% by weight of the composition. Anatase, rutile, and/or amorphous titanium dioxide find use in the present invention. Manufacturers of micronized grade titanium dioxide and zinc oxide for sunscreen use include, but are not limited to Tayca Corporation, Uniqema, Shinetsu Chemical Corporation, Kerr-McGee, Nanophase, Nanosource, Sachtleben, Elementis, and BASF Corporation, as well as their distribution agents and those companies that further process the material for sunscreen use. In some embodiments, physical sunblock particles (e.g., titanium dioxide and zinc oxide), are uncoated, while in alternative embodiments, the particles are coated with a variety of materials including but not limited to amino acids, aluminium compounds such as alumina, aluminium stearate, aluminium laurate, and the like; carboxylic acids and their salts (e.g., stearic acid and its salts); phospholipids (e.g., lecithin); organic silicon compounds; inorganic silicon compounds (e.g., silica and silicates), and mixtures thereof. In some embodiments, the personal care compositions of the present invention contain from about 0.1% to about 15%, preferably from about 0.1% to about 7% and more preferably from about 0.5% to about 5% by weight of an inorganic sunscreen.

In some preferred embodiments, the personal care compositions of the present invention contain preservatives. Such preservatives include, but are not limited to pentylene glycol, ethylene diamine tetra acetate ("EDTA") and its salts, chlorhexidine (and its diacetate, dihydrochloride, digluconate derivatives), 1,1,1-trichloro-2-methyl-2-propanol, parachloro metaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, 4-hydroxybenzoic acid and its (methyl-, ethyl-, propyl-, isopropyl-, butyl-, isobutyl-) esters (also known as parabens), salts, trichlosan, 2-phenoxyethanol, phenyl mercuric acetate, borate, nitrate, quaternium-15, salicilate, salicylic acid and its salts, calcium, sorbic acid and its salts, iodopropanyl butylcarbamate, calcium sorbate, zinc pyrithione, benzyl alcohol, 5-bromo-5nitro-1,3-dioxane, 2-bromo-2-nitropropane-1,3-diol, benzoic acid and its salts, sulfites, bisulfites, and benzalkonium chloride, phenoxyethanol and chloroxylenol, diazolidinyl urea, methylparaben, propylparaben, PG, isopropylparabens, isobutylparabens, butylparabens, ethylparaben, phenoxyethanol.

In further embodiments, a variety of optional ingredients such as neutralizing agents, perfumes and perfume solubilizing agents, and coloring agents, are included in the personal care compositions herein. Any additional ingredients should enhance the product, for example, the skin softness/smoothness benefits of the product. In addition, any such ingredients should not negatively impact the aesthetic properties of the product. Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

In yet further embodiments, other optional materials are included in the present invention, including any of the various functional and/or active ingredients known to those skilled in the art. (See e.g., McCutcheon's *Functional Materials*, North American and International Editions, [2003)], published by MC Publishing Co.). Non-limiting examples include: keratolytic agents; water-soluble or solubilizable preservatives specifically at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name GLYDANT PLUS™ (Lonza), EDTA, EUXYL® K400, BROMOPOL™ (2-bromo-2-nitropropane-1,3-diol) and phenoxypropanol; anti-bacterials such as IRGASANQ® and phenoxyethanol (specifically at levels of from about 0.1% to about 5%); soluble or colloidally-soluble moisturizing agents such as hyaluaronic acid and chondroitin sulfatestarch-grafted sodium polyacrylates such as SANWET® IM-1000, IM-1500 and IM-2500 available from Celanese Superabsorbent Materials, Portsmith, Va., USA and described in U.S. Pat. No. 4,076,663; vitamins such as vitamin A, vitamin C, vitamin E, vitamin K and derivatives thereof and building blocks thereof, such as phytantriol; and vitamin K and components thereof such as the fatty alcohols such as dodecatrienol; alpha and beta hydroxyacids; aloe vera; sphingosines and phytosphingosines, cholesterol; skin whitening agents; N-acetyl cysteine; colouring agents; antibacterial agents such as TCC/TCS, also known as triclosan and trichlorocarbon; perfumes and perfume solubilizers. Examples of alpha hydroxy acids include glycolic acid, lactic acid, malic acid, and citric acid (whether derived synthetically or from natural sources and whether used alone or in combination), and their esters or relevant buffered combinations, such as glycolic acid in conjunction with ammonium glycolate. Other examples of alpha-hydroxy acids include: alpha-hydroxy ethanoic acid, alpha-hydroxyoctanoic acid, alpha-hydroxy-caprylic acid, and hydroxycaprylic acid, mixed fruit acid, tri-alpha hydroxy fruit acids, triple fruit acid, sugar cane extract, alpha hydroxy and botanical comprise, 1-alpha hydroxy acid and glycomer in crosslinked fatty acids alpha nutrium. Specific examples of alpha hydroxy acids include glycolic acid and lactic acid. In a particular embodiment, alpha hydroxy acids are used in levels of up to about 10%.

In additional embodiments, optional materials such as pigments are included in the personal care compositions of the present invention, including water-insoluble pigments that contribute to and are included in the total level of oil phase ingredients. In some embodiments, the pigments used in the compositions of the present invention are organic, while in other embodiments they are inorganic. Also included within the term "pigment" are materials having a low color or luster, such as matte finishing agents, light scattering agents, and formulation aids (e.g., micas, seracites, and carbonate salts).

Further examples of suitable pigments include titanium dioxide, predispersed titanium dioxide, iron oxides, zinc oxide, bismuth oxychloride (whether pre-dispersed and/or pre-coated or not) coated iron oxides, ultramarine blue, D&C dyes and lakes, FD&C colors, natural color additives such as carmine, and mixtures thereof. Depending upon the type of composition, a mixture of pigments is usually used. Exemplary pigments for use herein from the viewpoint of moisturization, skin feel, skin appearance and emulsion compatibility are treated pigments (e.g., pigments treated with compounds, including but not limited to amino acids, silicones, lecithin and ester oils).

In most embodiments, the pH of the personal care compositions herein is in the range from about 3.5 to about 10, preferably from about 4 to about 8, and more preferably from about 5 to about 7, wherein the pH of the final composition is adjusted by addition of acidic, basic or buffer salts as necessary, depending upon the composition of the forms and the pH-requirements of the compounds.

Those skilled in the art will appreciate the various techniques for preparing the personal care compositions of the present invention, any of which may be employed herein. In general the aqueous phase and/or the oil phases are prepared separately, with materials of similar phase partitioning being added in any suitable order. For emulsion final products, the two phases are combined with vigorous stirring and/or homogenization as necessary to reduce the size of the internal phase droplets. Any ingredients in the formulation with high volatility, or which are susceptible to hydrolysis or decomposition at high temperatures, are preferably added with gentle stirring towards the end of the process, and/or at the post emulsification stage, if applicable. As known to those skilled in the art, dosage frequency and amount depends upon the desired performance criteria.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); Tg (glass transition temperature); DI (distilled water); MQ (milli-Q water; deionized water with further volatiles removed, to provide pure water with an electrical resistance of 18.2 ohms); PSI (pounds per square inch); CER (carbon dioxide evolution rate); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); g (gravity); xg (times gravity); OD (optical density); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); DMSO (dimethyl sulfoxide); PEI (polyethyleneimine); EGTA (ethylene glycol-bis(B-aminoethyl ether) N,N,N',N'-tetraacetic acid); EDTA (ethylenediaminetetraacetic acid); FBS (fetal bovine serum); FGM (fibroblast growth media); DMEM (Dulbecco's Modified Essential Media); DPBS (Dulbecco's phosphate buffered solution; PPTI (Protein Polymer Technologies, Inc., San Diego, Calif.); Dow Corning (Dow Corning Corporation, Midland, Mich.); Clariant (Clariant Corporation, Charlotte, N.C.); R&D (R&D Systems, Inc., Minneapolis, Minn.); Takara (Takara USA Corporation., New York, N.Y.); Biocolor (Biocolor, Ltd., Newtownabbey, Ireland); Hercules (Hercules, Inc., Wilmington, Del.); Cognis (Cognis Corp., Hoboken, N.J.); Uniqema (Uniqema, Inc., Wilmington, Del.); Croda (Croda, Inc., Parsippany, N.J.); Lonza (Lonza, Inc., Fairlawn, N.J.); Sun (Sun Chemical, Inc., Fort Lee, N.J.); Aqualon (Aqualon, Wilmington, Del.); S&P (Strahl & Ptisch, W. Babylon, N.Y.); Color Techniques (Color Techniques, South Plainfield, N.J.); Cascade Biologics (Cascade Biologics, Portland, Oreg.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); Invitrogen (Invitrogen, Inc., Grand Island, N.Y.); Abbott (Abbott Laboratories, Abbott Park, Ill.); Perkin Elmer (PerkinElmer Life Sciences, Boston Mass.); and Stratagene (Stratagene, La Jolla, Calif.).

In the experiments described below, the "RSPP test materials" are indicated in the following Table:

TABLE 1

| Test Materials | |
|---|---|
| RSPP Designation | RSPP |
| GC2596-26-A | SELP47K (monodispersed) |
| GC2596-26-B | SELP47K (polydispersed) |
| GC2596-26-C | SELP47K (monomeric form generated by lysC treatment) |
| GC2596-26-D | SELP47K (SELP47K-P4 RSPP) |
| CG2596-26-E | DCP6 RSPP (collagen-like protein) |

Material GC2596-26-A was monodispersed 13-mer SELP47K RSPP (See, Example 1), while Material GC2596-26-B was polydispersed SELP47K (See, Example 2). Material GC2596-26-C was SELP47K that was enzymatically treated with lysC to cleave full-length SELP47K into its monomeric unit having lysine residues at each end (See, Example 3). Material GC2596-26-D was SELP47K modified with two units of ALSYP (SEQ ID NO:36) peptides placed in each SELP47K unit prior to silk peptide repeats. (See, Example 4) Material GC2596-26-E was a modified collagen repeat sequence that was obtained from Protein Polymer Technologies (See, Example 5).

Example 1

Isolation of SELP

In this Example, experiments conducted to isolate and purify a genetically engineered silk-elastin repeat sequence protein block copolymer (SELP) from *E. coli* are described. *E. coli* containing a specific silk-elastin repeat sequence protein copolymer SELP47K (GC2596-26-A) recombinant DNA was obtained from PPTI. The *E. coli* may be prepared in accordance with the methods described in U.S. Pat. Nos. 5,243,038 and 6,355,776, incorporated herein by reference. The recovery of kilogram quantities of SELP was also demonstrated. The silk-elastin copolymer SELP47K had a general structure of head-[(GAGAGS)$_2$(GVGVP)$_3$GKGVP (GVGP)$_4$(GAGAGS)$_2$]$_{13}$-tail (SEQ ID NO:19). The copolymer contained 886 amino acids, with 780 amino acids in the repeating sequence unit. The SELP47K had a molecular weight of about 70,000 Daltons, and the pI of the protein is 10.5.

Monodispersed silk-elastin protein polymer SELP47K was produced for application testing in the following manner. *E. coli* fermentation was performed to produce a cell-paste containing monodispersed SELP47K. The cell-paste was placed in ice cold water and homogenized to make the cell extract. The cell-extract was mixed with polyethyleneimine and a filter-aid and was allowed to stir at 7° C. for one hour. The polyethyeleneimine caused precipitation of cell debris and a significant amount of *E. coli* proteins. The SELP47K containing reaction mixture was then filtered using Rotary Drum Vacuum Filter (RVDF). The filtered SELP47K solution was then mixed with ammonium sulfate to 25% saturation, which led to precipitation of SELP47K. Precipitated SELP47K and mother liquor was mixed with a filter-aid and again filtered using RVDF. The RVDF cake containing SELP47K and filter-aid was mixed with cold water to dissolve the SELP47K. This precipitation and solubilization step was repeated one more time to improve the purity profile of the SELP47K. Purified monodispersed SELP47K was then water-exchanged until the conductivity of SELP solution reached 50 µS/cm$^2$. The monodispersed SELP solution was then concentrated to 10% wt/vol and then lyophilized to make powdered monodispersed SELP47K protein polymer. The material was stored at −70° C. until needed for application testing.

SELP variants were either obtained from PPTI or genetically engineered. Table 2 provides a list of the variants and their properties.

TABLE 2

SELP Variants and Their Properties.

| Variant Name | Number of Subunits | Lysine Substitution | Molecular Weight (Da) | Isoelectric Point |
|---|---|---|---|---|
| SELP47E | 13 | Glutamic Acid | 70,212 | 4.16 |
| SELP47K-3 | 3 | none | 20,748 | 9.52 |
| SELP47R-3 | 3 | Arginine | 20,960 | 10.5 |
| SELP47E-3 | 3 | Glutamic Acid | 20,879 | 5.9 |
| SELP27K | 13 | none | 59,401 | 10.53 |
| SELP37K | 13 | none | 64,605 | 10.53 |
| SELP58 | 13 | none | 74,765 | 6.7 |
| SELP67K | 13 | none | 80,347 | 10.53 |

The *E. coli* strains containing a specific silk-elastin repeat sequence protein copolymer SELP47K, SELP37K, and SELP27K recombinant DNA were also obtained from PPTI. SELP67K, SELP58, SELP37K and SELP27K variant proteins were produced in 14 L fed batch culture using standard SELP47K production protocols, as described above. Proteins were purified and characterized as follows: 40 grams of cell pastes collected from 14 L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). SELP47K-3 species was excised from SDS-PAGE gels and further characterized, its identity confirmed, by LC-MS/MS (Liquid Chromatographic Mass Spectroscopy). The molecular weight of the intact SELP47K-3 protein was also confirmed using MALDI-TOF/MS (Matrix Assisted Laser Desorption Ionization Time of Flight Mass Spectrometry).

The protocol used for the genetic engineering of variants SELP47E, SELP47K-3, SELP47R-3, and SELP47E-3 is a modification of a commercially available kit designed to create single base pair changes in multiple sites along a particular DNA sequence (QUIKCHANGE® Multi-Site-Directed Mutagenesis Kit, Stratagene #200513). The standard protocol involves the construction of single direction 5' phosphorylated primers that will hybridize to plasmid template regions of interest and incorporate point mutations. Thermocycling is employed that includes a ligation reaction designed to link the multiple primers during each round of synthesis.

SELP DNA sequences are unique in that the multiple repeating subunits are identical. In order to change a single amino acid residue in all subunits a single change is effectively performed multiple times. The above protocol was further modified in that primers were designed pair-wise, complementary, thereby creating PCR amplification conditions in the thermocycling process. Amplified plasmid DNA was then used to transform *E. coli* cells and can be further screened and characterized for desired mutations.

Conversion of SELP Lysine Residues.

Primers were designed that direct a single base change mutation resulting in conversion of lysine residues to glutamic acids or arginines while simultaneously creating a unique restriction enzyme site at this location used for subsequent plasmid screening. 5' phosphorylated primers were made complementary, in both directions (both strands) as follows:

```
Glutamic Acid conversion:
                                      (SEQ ID NO: 21)
5'-GGGAGTTGGTGTACCTGGAGAAGGTGTTCCGGGGGTAGG-3'

(SEQ ID NO: 22)
3'-CCCTCAACCACATGGACCTCTTCCACAAGGCCCCCATCC-5'

(A20 was converted to G20)

Arginine Conversion:
                                      (SEQ ID NO: 23)
5'-GGGAGTTGGGGTACCTGGACGAGGTGTTCCGGGGGTAGG-3'

(SEQ ID NO: 24)
3'-CCCTCAACCCCATGGACCTGCAGGTGGAACCCCCCATCC-5'

(G19 and T20 were converted to C and G)
```

The QUIKCHANGE® Multi-Site kit was used per the manufacturer's protocol except that both complementary primers were included. Five µl of each reaction was used to transform TOP10 cells as per protocol (Invitrogen). 100 µl of salt optimized carbon (SOC) outgrowth were plated per reaction. Transformants were picked and grown in 5 ml LB containing 50 ppm kanamycin. Plasmid DNA was obtained from cultures using the Qiagen plasmid miniprep kit and analyzed by digestion with appropriate restriction enzymes followed by gel electrophoresis. Constructs that appeared correct were confirmed by DNA sequencing. Several rounds of the above protocol were required to obtain the SELP47E variant. In all cases this method resulted in the creation of a library consisting of variants spanning a range of subunits. This distribution ranged from 1 to 17 subunits. SELP47E-3 and SELP47R-3 were a result of this distribution. SELP47K-3 resulted from using the above methods to convert SELP47E-3 glutamic acids back to lysines.

Successful construct plasmids were used to transform *E. coli* MM294 using Lauryl Bertani (LB) plates containing 50 ppm kanamycin. Single colonies were picked and grown in 60 ml TM2 (recipe)+2% glucose, 50 ppm kanamycin in 500 ml fluted Erlenmeyer flasks, 30° C., 250 rpm, 16 hrs. Cell culture was supplemented with glycerol (10% v/v), and 1.5 ml aliquots were placed in cryovials and stored at −80° C. Random vials were tested for contamination by incubating 10 µl inoculating loopfuls on LA+1.6% skim milk plates, 37° C., for 16 hrs. Integrity of the plasmids was also confirmed using plasmid purification and analysis using restriction enzyme digestion/gel electrophoresis as well as DNA sequencing. Frozen cryovials were prepared using methods known in the art and used as seed stocks for subsequent culturing, protein production.

SELP47K-3, SELP47E-3 and SELP47R-3 variant proteins were produced in 14 L fed batch culture using standard SELP47K production protocols used above. Proteins were purified and characterized as follows: 40 grams of cell pastes collected from 14 L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). The SELP47K-3 species was excised from SDS-PAGE gels and further characterized, its identity confirmed, by LC-MS/MS. The molecular weight of the intact SELP47K-3 protein was also confirmed using MALDI-TOF/MS.–M3H+1641, M4H+1231 of silk-elastin unit at ~5 kDa.

Example 2

Preparation of Polydispersed SELP47K for Application Testing

Experiments involving the purification and preparation of the polydispersed SELP47K silk-elastin protein polymer (GC2596-26-B) for application testing are described in this Example. Cell separation from the fermentation broth was done using microfiltration. A cell disruption to make a cell-extract was done using a French-press. The cell extract was separated from the cell-debris using polyethyleneimine and a filter-aid. The cell extract was mixed with ammonium sulfate to 25% saturation to precipitate the silk-elastin protein polymer. The precipitated silk-elastin protein polymer was further purified by dissolving it in water and reprecipitating it with ammonium sulfate.

In order to prepare a polydispersed silk-elastin protein polymer, the precipitated silk-elastin protein polymer was again dissolved in water and mixed with a trace amount of protease (BPN'Y217L) (Genencor International). The protease was then inactivated and destroyed by acid treatment. The polydispersed silk-elastin protein polymer was then ultrafiltered until the silk-elastin protein polymer solution reached an electrical conductivity of 50 µS/m².

The polydispersed silk-elastin protein polymer solution was concentrated to 10 wt % and was lyophilized. The lyophilized polydisperesed silk-elastin protein polymer (GC2596-26-B) powder was stored at −70° C. until use. The lyophilized polydispersed silk-elastion protein was then dissolved in deionized water to a desired concentration for skin and hair application testing.

Example 3

Cleavage of Monodispersed SELP47K

This Example describes the methods used to cleave monodispersed SELP47K to its monomeric unit. The purification and formation of monomeric unit of SELP47K (4920 kDA molecular weight) (GC2596-26-C) was carried out using monodispersed material of SELP47K produced as in Example 1. The monodispersed SELP47K was dissolved in water and was treated with endopeptidase lysC protease (Sigma) specific for cleaving protein at lysine residue for 30 minutes at room temperature. The lysC protease was then inactivated and destroyed by acid treatment. The monomeric unit of SELP47K was then ultra-filtered until protein polymer solution conductivity reached 50 µS/m². The monomeric unit of SELP47K solution was then lyophilized to get the solid material and stored at −70 C prior to application testing.

Example 4

SELP47K-P4 Biosynthesis and Production

In this Example, the construction, analysis and verification of the SELP47K-P4 RSPP is described. The amino acid sequence for this RSPP is:

```
                                        (SEQ ID NO: 32)
MDPVVLQRRD WENPGVTQLN RLAAHPPFAS DPMGAGAGSG

AGAGSALSYP

GVGVPGVGVP GVGVPGVGVP GKGVPGVGVP GVGVPGVGVP

ALSYPGAGAG

SGAGAGSGAG AGSGAGAGSA LSYPGVGVPG VGVPGVGVPG

VGVPGKGVPG

VGVPGVGVPG VGVPALSYPG AGAGSGAGAG SGAGAGSGAG

AGSALSYPGV

GVPGVGVPGV GVPGVGVPGK GVPGVGVPGV GVPGVGVPAL

SYPGAGAGSG

AGAGSGAGAG SGAGAGSALS YPGVGVPGVG VPGVGVPGVG

VPGKGVPGVG

VPGVGVPGVG VPALSYPGAG AGSGAGAGSG AGAGSGAGAG

SALSYPGVGV

PGVGVPGVGV PGVGVPGKGV PGVGVPGVGV PGVGVPALSY

PGAGAGSGAG

AGSGAGAGSG AGAGSALSYP GVGVPGVGVP GVGVPGVGVP

GKGVPGVGVP

GVGVPGVGVP ALSYPGAGAG SGAGAGSGAG AGSGAGAGSA

LSYPGVGVPG

VGVPGVGVPG VGVPGKGVPG VGVPGVGVPG VGVPALSYPG

AGAGSGAGAG

SGAGAGSGAG AGSALSYPGV GVPGVGVPGV GVPGVGVPGK
```

-continued

```
GVPGVGVPGV
GVPGVGVPAL SYPGAGAGSG AGAGSGAGAG SGAGAGSALS
YPGVGVPGVG
VPGVGVPGVG VPGKGVPGVG VPGVGVPGVG VPALSYPGAG
AGSGAGAGSG
AGAGSGAGAG SALSYPGVGV PGVGVPGVGV PGVGVPGKGV
PGVGVPGVGV
PGVGVPALSY PGAGAGSGAG AGSGAGAGSG AGAGSALSYP
GVGVPGVGVP
GVGVPGVGVP GKGVPGVGVP GVGVPGVGVP ALSYPGAGAG
SGAGAGSGAG
AGSGAGAGSA LSYPGVGVPG VGVPGVGVPG VGVPGKGVPG
VGVPGVGVPG
VGVPALSYPG AGAGSGAGAG SGAGAGSGAG AGSALSYPGV
GVPGVGVPGV
GVPGVGVPGK GVPGVGVPGV GVPGVGVPAL SYPGAGAGSG
AGAGSGAGAM
DPGRYQDLRS HHHHHH*
```

The DNA sequence for this RSPP is:

```
                                          (SEQ ID NO: 33)
ATGGATCCCG TCGTTTTACA ACGTCGTGAC TGGGAAAACC
CTGGCGTTAC
CCAACTTAAT CGCCTTGCAG CACATCCCCC TTTCGCCAGC
GATCCGATGG
GAGCGGGTGC CGGTTCTGGT GCAGGCGCGG GCTCTGCGCT
GAGCTATCCG
GGTGTTGGAG TGCCAGGTGT CGGTGTTCCG GGTGTAGGCG
TTCCGGGAGT
TGGTGTACCT GGAAAAGGTG TTCCGGGGGT AGGTGTGCCG
GGCGTTGGAG
TACCAGGTGT AGGCGTCCCG GCGCTGAGCT ATCCGGGAGC
GGGTGCTGGT
AGCGGCGCAG GCGCGGGCTC TGGAGCGGGT GCCGGTTCTG
GTGCAGGCGC
GGGCTCTGCG CTGAGCTATC CGGGTGTTGG AGTGCCAGGT
GTCGGTGTTC
CGGGTGTAGG CGTTCCGGGA GTTGGTGTAC CTGGAAAAGG
TGTTCCGGGG
GTAGGTGTGC CGGGCGTTGG AGTACCAGGT GTAGGCGTCC
CGGCGCTGAG
CTATCCGGGA GCGGGTGCTG GTAGCGGCGC AGGCGCGGGC
TCTGGAGCGG
GTGCCGGTTC TGGTGCAGGC GCGGGCTCTG CGCTGAGCTA
TCCGGGTGTT
GGAGTGCCAG GTGTCGGTGT TCCGGGTGTA GGCGTTCCGG
GAGTTGGTGT
ACCTGGAAAA GGTGTTCCGG GGGTAGGTGT GCCGGGCGTT
GGAGTACCAG
GTGTAGGCGT CCCGGCGCTG AGCTATCCGG GAGCGGGTGC
TGGTAGCGGC
GCAGGCGCGG GCTCTGGAGC GGGTGCCGGT TCTGGTGCAG
GCGCGGGCTC
TGCGCTGAGC TATCCGGGTG TTGGAGTGCC AGGTGTCGGT
GTTCCGGGTG
TAGGCGTTCC GGGAGTTGGT GTACCTGGAA AAGGTGTTCC
GGGGGTAGGT
GTGCCGGGCG TTGGAGTACC AGGTGTAGGC GTCCCGGCGC
TGAGCTATCC
GGGAGCGGGT GCTGGTAGCG GCGCAGGCGC GGGCTCTGGA
GCGGGTGCCG
GTTCTGGTGC AGGCGCGGGC TCTGCGCTGA GCTATCCGGG
TGTTGGAGTG
CCAGGTGTCG GTGTTCCGGG TGTAGGCGTT CCGGGAGTTG
GTGTACCTGG
AAAAGGTGTT CCGGGGGTAG GTGTGCCGGG CGTTGGAGTA
CCAGGTGTAG
GCGTCCCGGC GCTGAGCTAT CCGGGAGCGG GTGCTGGTAG
CGGCGCAGGC
GCGGGCTCTG GAGCGGGTGC CGGTTCTGGT GCAGGCGCGG
GCTCTGCGCT
GAGCTATCCG GTGTTGGAG TGCCAGGTGT CGGTGTTCCG
GGTGTAGGCG
TTCCGGGAGT TGGTGTACCT GGAAAAGGTG TTCCGGGGGT
AGGTGTGCCG
GGCGTTGGAG TACCAGGTGT AGGCGTCCCG GCGCTGAGCT
ATCCGGGAGC
GGGTGCTGGT AGCGGCGCAG GCGCGGGCTC TGGAGCGGGT
GCCGGTTCTG
GTGCAGGCGC GGGCTCTGCG CTGAGCTATC CGGGTGTTGG
AGTGCCAGGT
GTCGGTGTTC CGGGTGTAGG CGTTCCGGGA GTTGGTGTAC
```

```
CTGGAAAAGG

TGTTCCGGGG GTAGGTGTGC CGGGCGTTGG AGTACCAGGT

GTAGGCGTCC

CGGCGCTGAG CTATCCGGGA GCGGGTGCTG GTAGCGGCGC

AGGCGCGGGC

TCTGGAGCGG GTGCCGGTTC TGGTGCAGGC GCGGGCTCTG

CGCTGAGCTA

TCCGGGTGTT GGAGTGCCAG GTGTCGGTGT TCCGGGTGTA

GGCGTTCCGG

GAGTTGGTGT ACCTGGAAAA GGTGTTCCGG GGGTAGGTGT

GCCGGGCGTT

GGAGTACCAG GTGTAGGCGT CCCGGCGCTG AGCTATCCGG

GAGCGGGTGC

TGGTAGCGGC GCAGGCGCGG GCTCTGGAGC GGGTGCCGGT

TCTGGTGCAG

GCGCGGGCTC TGCGCTGAGC TATCCGGGTG TTGGAGTGCC

AGGTGTCGGT

GTTCCGGGTG TAGGCGTTCC GGGAGTTGGT GTACCTGGAA

AAGGTGTTCC

GGGGGTAGGT GTGCCGGGCG TTGGAGTACC AGGTGTAGGC

GTCCCGGCGC

TGAGCTATCC GGGAGCGGGT GCTGGTAGCG GCGCAGGCGC

GGGCTCTGGA

GCGGGTGCCG GTTCTGGTGC AGGCGCGGGC TCTGCGCTGA

GCTATCCGGG

TGTTGGAGTG CCAGGTGTCG GTGTTCCGGG TGTAGGCGTT

CCGGGAGTTG

GTGTACCTGG AAAAGGTGTT CCGGGGGTAG GTGTGCCGGG

CGTTGGAGTA

CCAGGTGTAG GCGTCCCGGC GCTGAGCTAT CCGGGAGCGG

GTGCTGGTAG

CGGCGCAGGC GCGGGCTCTG GAGCGGGTGC CGGTTCTGGT

GCAGGCGCGG

GCTCTGCGCT GAGCTATCCG GGTGTTGGAG TGCCAGGTGT

CGGTGTTCCG

GGTGTAGGCG TTCCGGGAGT TGGTGTACCT GGAAAAGGTG

TTCCGGGGT

AGGTGTGCCG GGCGTTGGAG TACCAGGTGT AGGCGTCCCG

GCGCTGAGCT

ATCCGGGAGC GGGTGCTGGT AGCGGCGCAG GCGCGGGCTC

TGGAGCGGGT

GCCGGTTCTG GTGCAGGCGC GGGCTCTGCG CTGAGCTATC

CGGGTGTTGG

AGTGCCAGGT GTCGGTGTTC CGGGTGTAGG CGTTCCGGGA

GTTGGTGTAC

CTGGAAAAGG TGTTCCGGGG GTAGGTGTGC CGGGCGTTGG

AGTACCAGGT

GTAGGCGTCC CGGCGCTGAG CTATCCGGGA GCGGGTGCTG

GTAGCGGCGC

AGGCGCGGGC TCTGGAGCGG GTGCCGGTTC TGGTGCAGGC

GCGGGCTCTG

CGCTGAGCTA TCCGGGTGTT GGAGTGCCAG GTGTCGGTGT

TCCGGGTGTA

GGCGTTCCGG GAGTTGGTGT ACCTGGAAAA GGTGTTCCGG

GGGTAGGTGT

GCCGGGCGTT GGAGTACCAG GTGTAGGCGT CCCGGCGCTG

AGCTATCCGG

GAGCGGGTGC TGGTAGCGGC GCAGGCGCGG GCTCTGGAGC

GGGTGCCATG

GACCCGGGTC GATATCAGGA TCTTAGATCT CATCACCATC

ACCATCACTA

A
```

SELP constructs in which all polymer subunits contain additional P4 (ALSYP; SEQ ID NO:36) peptide sequences were made as follows: Artificial gene synthesis was used to create a 2 subunit version of the desired construct in which each identical subunit contained a unique non-palindromic restriction site. Specifically, SELP subunits contained either BBI (Bowman-Birk Inhibitor)-derived P4 sequence (i.e., ALSYP; SEQ ID NO:36) incorporated in two places per subunit, flanking the silk region, incorporated between the C-terminal end of the silk region and the N-terminal end of the elastin region. A BsgI restriction enzyme cleavage site was designed within each subunit.

The construct DNA was digested with BsgI, which resulted in the release of a single subunit per molecule. Resulting modified SELP monomers as well as plasmid vector were purified from agarose gels and concentrated using a Spin Vac. Monomers were self-ligated using T4 DNA ligase (New England Biolabs) overnight at 16° C., as per the manufacturer's instructions. Original purified vector was added to the ligation mix with additional fresh ligase and incubated at 16° C. for an additional 24 hours. This ligation mix was used to transform E. coli TOP10 cells (Invitrogen) as per the manufacturer's instructions. The resulting transformants were used to inoculate culture tubes containing 5 ml Luria broth and appropriate antibiotic. Tubes were incubated for 16 hrs, at 37° C., and with shaking at 250 rpm. Plasmids were purified from resulting cultures using a Plasmid Miniprep kit (Qiagen). Complete SELP inserts were excised from vector by digestion with EcoRV and BamHI restriction enzymes and sized using agarose gel elecrophoresis in order to identify constructs containing the desired 13 total subunits.

Appropriate SELP-P4 gene constructs were subcloned into a vector containing the lambda Pr promoter and transformed into production the host *E. coli* MM294. Prepared seed vials were stored at −80° C. These seed vials were used for fermentation of SELP47K-P4 repeat sequence protein polymers. The strain tested for fermentation run was MM294/pSELP01472 (SELP47K-P4; GC2596-26-D). The *E. coli* strain was incubated in defined TM2 medium and batched glucose. The fermentation was continued with a feed of 2 g/min of glucose upon consumption of batched glucose until the cells in the fermenters grew up to an OD of 60. The expression of SELP47K protein polymer was started with temperature induction by raising the fermentation temperature to 40° C. The fermentation and growth rates were very similar to that of SELP47K (Example 1). The cells grew well prior to, as well as after induction. Cell pastes were harvested by centrifuging fermentation broth after 20% drop in CER and with no further rise in OD. Purification of SELP47K-P4 RSPP test material was performed by first taking the cell paste in 1:2 ratio in DI water, followed by homogenizing the cells using French-Press at 8000 PSI. Homogenized cells were mixed with 0.1%-10% PEI (polyethyleneimine) to flock-out cell debris. The cell debris was removed by centrifugation. The cell extract generated from centrifugation was mixed with ammonium sulfate (10-25% saturation) to precipitate SELP47K-P4 RSPP test material. Precipitated SELP47K-P4 RSPP was separated from the solution and dissolved in either MQ water or a chaotropic agent (e.g., urea or guanidinium hydrochloride). SELP47K-P4 RSPP was purified by dialysis and then lyophilized as solid powder for storage, using methods known in the art. Analysis of purified P4-SELP47K was carried out using SDS gel electrophoresis as well as mass spectrometry to confirm the formation of fusion polymer.

Example 5

Production of DCP6 (GC 2596-26-E)

In this Example, experiments conducted to isolate and purify a genetically engineered collagen-like repeat sequence protein block copolymer (DCP6) from *E. coli* are described. *E. coli* host MM294/pPPTI0301 strain containing a specific silk-elastin repeat sequence protein copolymer DCP6 (GC2596-26-E) recombinant DNA was obtained from PPTI. The *E. coli* was prepared in accordance with the methods described in U.S. Pat. Nos. 5,243,038 and 6,355,776, incorporated by reference herein.

The collagen-like repeat sequence protein polymer had a general structure of head-[(GAHGPAGPK)$_2$(GAQGPAGPG)$_{24}$(GAHGPAGPK)$_2$]$_4$-tail (SEQ ID NO:37). The copolymer contained 1008 amino acids, with 947 amino acids in the repeating sequence units. The DCP6 had a molecular weight of about 78,881 Daltons (calculated using mass spectrometry), and the pI of the protein was 11.18. The amino acid sequence is shown below:

```
                                            (SEQ ID NO: 34)
MDPVVLQRRDWENPGVTQLNRLAAHPPFASDPMGAHGPAGPKGAHGP

AGPKGAQGPAGPG GAQGPAGPG GAQGPAGPG GAQGPAGPG GAQGP

AGPG GAQGPAGPG GAQGPAGPG GAQGPAGPG GAQGPAGPG GAQGP

AGPG GAQGPAGPG GAQGPAGPG GAQGPAGPG GAQGPAGPG GAQGP

AGPG GAQGPAGPG GAQGPAGPG GAQGPAGPG GAQGPAGPG GAQGP

AGPG GAQGPAGPG GAQGPAGPG GAQGPAGPG GAQGPAGP GGAHGP

AGPKGAHGPAGPK GAHGPAGPKGAHGPAGPKGAQGPAGPG GAQGPA

GPG GAQGPAGPG GAQGPAGPG GAQGPAGPG GAQGPAGPG GAQGPA

GPG GAQGPAGPG GAQGPAGPG GAQGPAGPG GAQGPAGPG GAQGPA

GPG GAQGPAGPG GAQGPAGPG GAQGPAGPG GAQGPAGPG GAQGPA

GPG GAQGPAGPG GAQGPAGPG GAQGPAGPG GAQGPAGPG GAQGPA

GPG GAQGPAGPG GAQGPAGPGGAHGPAGPKGAHGPAGPKGAHGPA

GPKGAHGPAGPKGAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPA GPG GAHGPAGPKGAHGPAGPKGAHGPAGPKGAHGPAGPKGA

QGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPG GAQGPAGPG

GAQGPAGPG GAQGPAGPG GAQGPAGPG GAQGPAGPGGAHGPAGPKG

AHGPAG PKMDPGRYQLSAGRYHYQLVWCQK
```

The DNA sequence of this RSPP is

```
                                            (SEQ ID NO: 35)
GGCGCGCATGGCCCGGCGGGCCCGAAAGGCGCGCATGGCCCGGCGGGCC

CGAAAGGCGCGCAGGGCCCGGCGGGCCCGGCGGCGCGCAGGGCCCGGC

GGGCCCGGCGGCGCGCAGGGCCCGGCGGGCCCGGCGGCGCGCAGGGC

CCGGCGGGCCCGGCGGCGCGCAGGGCCCGGCGGGCCCGGCGGCGCGC

AGGGCCCGGCGGGCCCGGCGGCGCGCAGGGCCCGGCGGGCCCGGGCGG

CGCGCAGGGCCCGGCGGGCCCGGCGGCGCGCAGGGCCCGGCGGGCCCG

GCGGCGCGCAGGGCCCGGCGGGCCCGGCGGCGCGCAGGGCCCGGCGG

GCCCGGCGGCGCGCAGGGCCCGGCGGGCCCGGCGGCGCGCAGGGCCC

GGCGGGCCCGGCGGCGCGCAGGGCCCGGCGGGCCCGGCGGCGCGCAG

GGCCCGGCGGGCCCGGCGGCGCGCAGGGCCCGGCGGGCCCGGCGGCG

CGCAGGGCCCGGCGGGCCCGGCGGCGCGCAGGGCCCGGCGGGCCCGGG

CGGCGCGCAGGGCCCGGCGGGCCCGGCGGCGCGCAGGGCCCGGCGGGC

CCGGCGGCGCGCAGGGCCCGGCGGGCCCGGCGGCGCGCAGGGCCCGG

CGGGCCCGGCGGCGCGCAGGGCCCGGCGGGCCCGGCGGCGCGCAGGG

CCCGGCGGGCCCGGCGGCGCGCATGGCCCGGCGGGCCCGAAAGGCGCG

CATGGCC

CGGCGGGCCCGAAAGGCGCGCATGGCCCGGCGGGCCCGAAAGGCGCGCA

TGGCCCGGCGGGCCCGAAAGGCGCGCAGGGCCCGGCGGGCCCGGCGGC

GCGCAGGGCCCGGCGGGCCCGGCGGCGCGCAGGGCCCGGCGGGCCCGG
```

```
-continued
GCGGCGCGCAGGGCCCGGCGGGCCCGGCGGCGCGCAGGGCCCGGCGGG

CCCGGCGGCGCGCAGGGCCCGGCGGGCCCGGCGGCGCGCAGGGCCCG

GCGGGCCCGGCGGCGCGCAGGGCCCGGCGGGCCCGGCGGCGCGCAGG

GCCCGGCGGGCCCGGCGGCGCGCAGGGCCCGGCGGGCCCGGCGGCGC

GCAGGGCCCGGCGGGCCCGGCGGCGCGCAGGGCCCGGCGGGCCCGGC

GGCGCGCAGGGCCCGGCGGGCCCGGCGGCGCGCAGGGCCCGGCGGGCC

CGGGCGGCGCGCAGGGCCCGGCGGGCCCGGCGGCGCGCAGGGCCCGGC

GGGCCCGGCGGCGCGCAGGGCCCGGCGGGCCCGGCGGCGCGCAGGGC

CCGGCGGGCCCGGCGGCGCGCAGGGCCCGGCGGGCCCGGCGGCGCGC

AGGGCCCGGCGGGCCCGGCGGCGCGCAGGGCCCGGCGGGCCCGGCGG

CGCGCAGGGCCCGGCGGGCCCGGCGGCGCGCAGGGCCCGGCGGGCCG

GGCGGCGCGCAGGGCCCGGCGGGCCCGGCGGCGCGCATGGCCCGGCGG

GCCCGAAAGGCGCGCATGGCCCGGCGGGCCCGAAAGGCGCGCATGGCCC

GGCGGGCCCGAAAGGCGCGCATGGCCCGGCGGGCCCGAAAGGCGCGCAG

GGCCCGGCGGGCCCGGCGGCGCGCAGGGCCCGGCGGGCCCGGCGGCG

CGCAGGGCCCGGCGGGCCCGGCGGCGCGCAGGGCCCGGCGGGCCCGGG

CGGCGCGCAGGGCCCGGCGGGCCCGGCGGCGCGCAGGGCCCGGCGGGC

CCGGCGGCGCGCAGGGCCCGGCGGGCCCGGCGGCGCGCAGGGCCCGG

CGGGCCCGGCGGCGCGCAGGGCCCGGCGGGCCCGGCGGCGCGCAGGG

CCCGGCGGGCCCGGCGGCGCGCAGGGCCCGGCGGGCCCGGCGGCGCGC

CAGGGCCCGGCGGGCCCGGCGGCGCGCAGGGCCCGGCGGGCCCGGCG

GCGCGCAGGGCCCGGCGGGCCCGGCGGCGCGCAGGGCCCGGCGGGCCC

GGGCGGCGCGCAGGGCCCGGCGGGCCCGGCGGCGCGCAGGGCCCGCG

GGCCCGGCGGCGCGCAGGGCCCGGCGGGCCCGGCGGCGCGCAGGGCC

CGGCGGGCCCGGCGGCGCGCAGGGCCCGGCGGGCCCGGCGGCGCGCA

GGGCCCGGCGGGCCCGGCGGCGCGCAGGGCCCGGCGGGCCCGGCGGC

GCGCAGGGCCCGGCGGGCCCGGCGGCGCGCAGGGCCCGGCGGGCCCGG

GCGGCGCGCATGGCCCGGCGGGCCCGAAAGGCGCGCATGGCCCGGCGGG

CCCGAAAGGCGCGCATGGCCCGGCGGGCCCGAAAGGCGCGCATGGCCCG

GCGGGCCCGAAAGGCGCGCAGGGCCCGGCGGGCCCGGCGGCGCGCAGG

GCCCGGCGGGCCCGGCGGCGCGCAGGGCCCGGCGGGCCCGGCGGCGC

GCAGGGCCCGGCGGGCCCGGCGGCGCGCAGGGCCCGGCGGGCCCGGC

GGCGCGCAGGGCCCGGCGGGCCCGGCGGCGCGCAGGGCCCGGCGGGCC

CGGGCGGCGCGCAGGGCCCGGCGGGCCCGGCGGCGCGCAGGGCCCGGC

GGGCCCGGCGGCGCGCAGGGCCCGGCGGGCCCGGCGGCGCGCAGGGC

CCGGCGGGCCCGGCGGCGCGCAGGGCCCGGCGGGCCCGGCGGCGCGC

AGGGCCCGGCGGGCCCGGCGGCGCGCAGGGCCCGGCGGGCCCGGCGG

CGCGCAGGGCCCGGCGGGCCCGGCGGCGCGCAGGGCCCGGCGGGCCCG

GGCGCGCAGGGCCCGGCGGGCCCGGCGGCGCGCAGGGCCCGGCGGCGG

GCCCGGGCGGCGCGCAGGGCCCGGCGGGCCCGGCGGCGCGCAGGGCCC

GGCGGGCCCGGCGGCGCGCAGGGCCCGGCGGGCCCGGCGGCGCGCAG

GGCCCGGCGGGCCCGGCGGCGCGCAGGGCCCGGCGGGCCCGGCGGCG

CGCAGGGCCCGGCGGGCCCGGCGGCGCGCATGGCCCGGCGGGCCCGAA

AGGCGCGCATGGCCCGGCGGGCCCGAAA
```

DCP6 RSPP test material was produced for application testing in the following manner. The strain tested for fermentation run was MM294/pPPTI301 (DCP6; GC2596-26-E). The *E. coli* strain was incubated in defined TM2 medium and batched glucose. The fermentation was continued with a feed of 2 g/min of glucose upon consumption of batched glucose until the cells in the fermenters grew up to an OD (550 nm) of 60. The expression of SELP47K protein polymer was started with temperature induction by raising the fermentation temperature to 40° C. The fermentation and growth rates were very similar to that of SELP47K (Example 1). The cells grew well prior to, as well as after induction. Cell pastes were harvested by centrifuging fermentation broth after 20% drop in CER and with no further rise in OD (550 nm). The cell-paste was placed in DI water and homogenized to make the cell extract. The cell-extract was centrifuged and lysate was dialysed against pH 4 formate buffer followed by neutralization of dialysate. The dialysate was further purified using bulk anion exchange chromatography, as known in the art. Purified elute was then concentrated and redialyzed against water followed by lyophilization to obtain DCP6 test RSPP material (GC2596-26-E). The material was stored at −70° C. until needed for application testing, as described in the following Examples.

Example 6

Isoelectric Point and Cloud Point Determinations

In this Example, experiments performed to determine the isoelectric point and cloud point of SELP47K (Example 1) are described. The isoelectric point of SELP47K was determined by electrophoresing 5 mg/ml SELP47K solution using Isoelectric Focusing Electrophoresis (IEF) gel and Novex electrophoresis apparatus along with protein standards markers. Analysis of the gel revealed that SELP47K is a cationic protein with an isoelectric point of 10.4. Analysis of the IEF gels for isoelectric point determination of other RSPP examples reported in Table 2 were found to be within (±0.2) range.

The cloud point of SELP47K was determined by first preparing 0.1% and 1% solutions of polydispersed SELP 47K (Example 2) in three different buffers: 50 mM acetate pH 5; 50 mM Tris pH 7; 50 mM Tris pH 9. A 0.5 M NaCl salt solution was prepared in water and salt containing solutions were prepared using this stock solution. Samples were placed in quartz cuvettes and the cloud point determination was carried out using a Cary 300 spectrophotometer equipped with a thermal program and multiple cuvettes configuration. Turbidity measurements were made at 300 nm and the temperature was varied from 20-80° C.

It was determined that increasing the concentration of SELP47K in water lowered the cloud point of the protein polymer. A 0.05% solution of protein remains soluble in water even at 80° C. However, a 1% solution has a cloud point of 70° C. It was also determined that increasing pH from 5 to 9 also has a lowering effect on the cloud point of the protein polymer in very dilute solutions. At pH 5, the 0.1% solution remained soluble even at 80° C. At pH 9, the cloud point of 0.1% protein solution dropped down to 60° C. The 1% protein polymer solution showed similar cloud point of 65° C. in the 5-9 pH range.

It was also determined that increasing the salt concentration also lowered the cloud point of the SELP47K protein polymer. In pH 5 buffer, 1% protein polymer solution has a cloud point of 75° C. However, the cloud point was 65° C. with 0.2 M salt and below 60° C. when the salt concentration was raised to 0.5 M. The presence of a high salt concentration in dilute protein solutions had more affect on the cloud point than that of a relatively less dilute solution of protein polymer. A 0.1% solution had a cloud point of 50° C. when 0.5 M NaCl was present in the solution irrespective of pH. A 1% solution with 0.5 M salt has cloud point of 55° C. irrespective of pH.

Example 7

Determination of the Glass Transition Temperature and Decomposition Temperature of SELP47K In this Example, experiments performed to determine the glass transition temperature (Tg) and decomposition temperature of SELP47K. (Example 1) are described. Approximately 10 mg of SELP47K material was crimped in an aluminum (Al) pan, cooled to <−150° C., then heated to >200° C. at 10° C./min under a He (helium) atmosphere. The sample displayed an endothermic peak ranging from approximately 6 to 180° C. This initially appeared to be followed by another endothermic region and the analysis was stopped near 225° C. The sample was examined and had darkened significantly from the light golden starting color. Another sample of material was examined by TGA and found to have mass loss (~8%) from room temperature to approximately 200° C., confirming the broad endotherm observed with the first sample.

A strip of SELP47K was examined by using a dynamic mechanical analyzer (DMA) over the range of −150 to 200° C. Three tan delta peaks were observed at −109, 70, and 189° C. The peak at 189° C. coincided with a significant drop in modulus and a step change half-height in a differential scanning calorimeter (DSC) run in the same region initially was thought to be another endotherm suggesting the Tg of the material is approximately 189° C. Another DSC sample was run, pre-heating at 100° C. for 1 hour initially to remove volatiles. The mass loss endotherm was mostly removed, and a transition at 188° C. (half-height) remained. This run was stopped and the sample cooled and examined.

Based upon the results obtained, the material has a glass transition at approximately 189° C. Since there is mass loss on heating (water loss), this transition would be for the "film" material. Material degradation also appears to start near Tg. The decomposition temperature of this SELP47K was found to be 332° C.

Example 8

Tensile Mechanical Properties of SELP47K

In this Example, experiments performed to determine tensile mechanical properties of SELP47K (Example 1 and 2) are described. Samples of SELP47K were prepared by freeze-drying purified SELP47K solution. The subsequent powder was re-dissolved in water to a solids concentration of approximately 5, 10 or 20%. These solutions were then mixed with plasticizers to an effective concentration of 1-3%. Plasticizers included in this study were polyethylene glycol 200, glycerin, and triethanolamine. Eleven milliliters of these solutions were poured into a large (6 inch square) polyethylene weigh boats and the solutions were allowed to dry either in an oven at 37° C. or room temperature for 1 to 3 days. Subsequent films were successfully peeled from the weigh boat with a spatula without any damage to the polymer film.

The films were then cut into tensile specimens using a very sharp fabric cutting wheel. The specimens were approximately 6 cm long and 2.5 cm wide. The gauge length for these samples (length of sample between tensile testing clamps) was set to 3 cm and the thickness of the sample was measured at 5 points along the gauge length using a digital thickness coating instrument. The thickness of the samples was recorded as the average of the 5 points and varied from 46.4 to 188.2 microns. Both the sample width and sample thickness were entered into an Instron software program (Merlin) to enable it to calculate the tensile strength and tensile modulus.

The samples were loaded into the jaws of an INSTRON® Model 5564 apparatus making sure the gauge length was always set to 3 cm and that the sample was not under any static load or stress. The 2,500 Newton (2.5 KN) load cell was used since these samples exhibited loads between 55 and 150 Newtons at break. The results of the stress-strain measurements can be seen for four of the samples in FIG. 1. The elongation % of SELP47K was determined to be 8.4 for 20% SELP47K solution film made at room temperature (RM). The tensile strength was determined to be 65.9 megapascals (MPa), and the tensile modulus was determined to be 1716.50 MPa. The results of plastisizer-SELP47K films reveal strong correlation between concentration and mechanical properties measured. For 3% PEG200 containing SELP47K, the films elongation % reached 541. The tensile strength (MPA) and tensile strain (%) for each protein polymer tested are provided in Table 3.

TABLE 3

| Protein Polymer | Tensile Strength (MPA) | Tensile Strain (%) |
|---|---|---|
| (Example 1 Material [GC2596-26-A]) | | |
| SELP47K (10% sol., RM) | 62.98 | 3.5 |
| SELP47K (20% sol., 37 C) | 74.14 | 8.6 |
| SELP47K (20% sol., RM) | 65.90 | 8.4 |
| SELP47K (05% sol., 37 C) | 19.83 | 2.6 |
| SELP47K (05% sol., RM) | 21.43 | 2.4 |
| SELP47K (20% sol., RM) + 2% Glycerol | 27.65 | 180.5 |
| SELP47K (20% sol., RM) + 2% PEG 200 | 42.25 | 541.7 |
| SELP47K (20% sol., RM) + 1% PEG 200 | 67.84 | 7.9 |
| SELP47K (20% sol., RM) + 3% TEA | 49.65 | 87 |
| SELP47K (20% sol., RM) + 1% TEA | 54.96 | 31 |
| Nylon 6 | 50.56 | 50.6 |
| Polystyrene | 42.66 | 1.8 |
| Low Density Polyethylene | 49.98 | 375.4 |
| (Example 2 Material [GC2596-26-B]) | | |
| SELP47K (10% sol., 37 C) | 39.34 | 6.98 |
| SELP47K (10% sol, 37 C) + 1% glycerol | 25.12 | 15.75 |

Example 9

SELP47K Film

This Example describes the casting of a SELP47K (Example 1) films. First, a thin film was cast, starting with a 10% solution of SELP47K in water was prepared. The spin coater used for making thin film was from Special Coating Systems Inc., model number P6708-D (Indianapolis, USA). The DV-1000 program was used for spinning the film. SELP47K protein solution was poured over a 316 stainless steel plate that was placed on the spinner. The spinner was rotated at 2000 rpm for 30 seconds followed by rotation at 1000 rpm for 90 seconds. The thin film was allowed to dry for an hour and the thickness of the film was measured using a magnetometer. The average thickness of the SELP47K thin film was between 2-5 µm.

A SELP47K (Example 1) thick film was cast in the following manner. A 10% solution of SELP47K was prepared in deionized water (DI). This solution was poured to 1 mm in height into a plastic container and was allowed to set at 37° C. or room temperature for several hours leading to the formation of films. These films averaged between about 50-200 µm in thickness.

A SELP47K (Example 1) clear thick film was cast in the following manner. A 5% solution of SELP47K was prepared in DI water. This solution was poured to 1 mm thickness on a sheet of Saran Wrap™ kept in a shallow plastic container. This container was maintained at room temperature overnight leading to the formation of a clear thick film of SELP47K. SELP47K film made though this method yielded excellent optical transparency. No X-ray diffraction pattern was obtained from this material, and, thus, the material of this film was amorphous in nature. A 1% water solution of SELP47K when analyzed by circular dichroism spectroscopy, predicted 50% random coil and 50% beta sheet structure.

Example 10

Microscopy of SELP47K

This Example describes microscopic studies of SELP47K (Example 1 and 2 material). In these experiments, the morphology of Silk Elastin Protein (SELP47K) was characterized using various microscopy techniques including: 1) optical microscopy; 2) Field Emission Scanning Electron Microscopy (FE-SEM); and 3) Atomic Force Microscopy (AFM).

Figure 2:
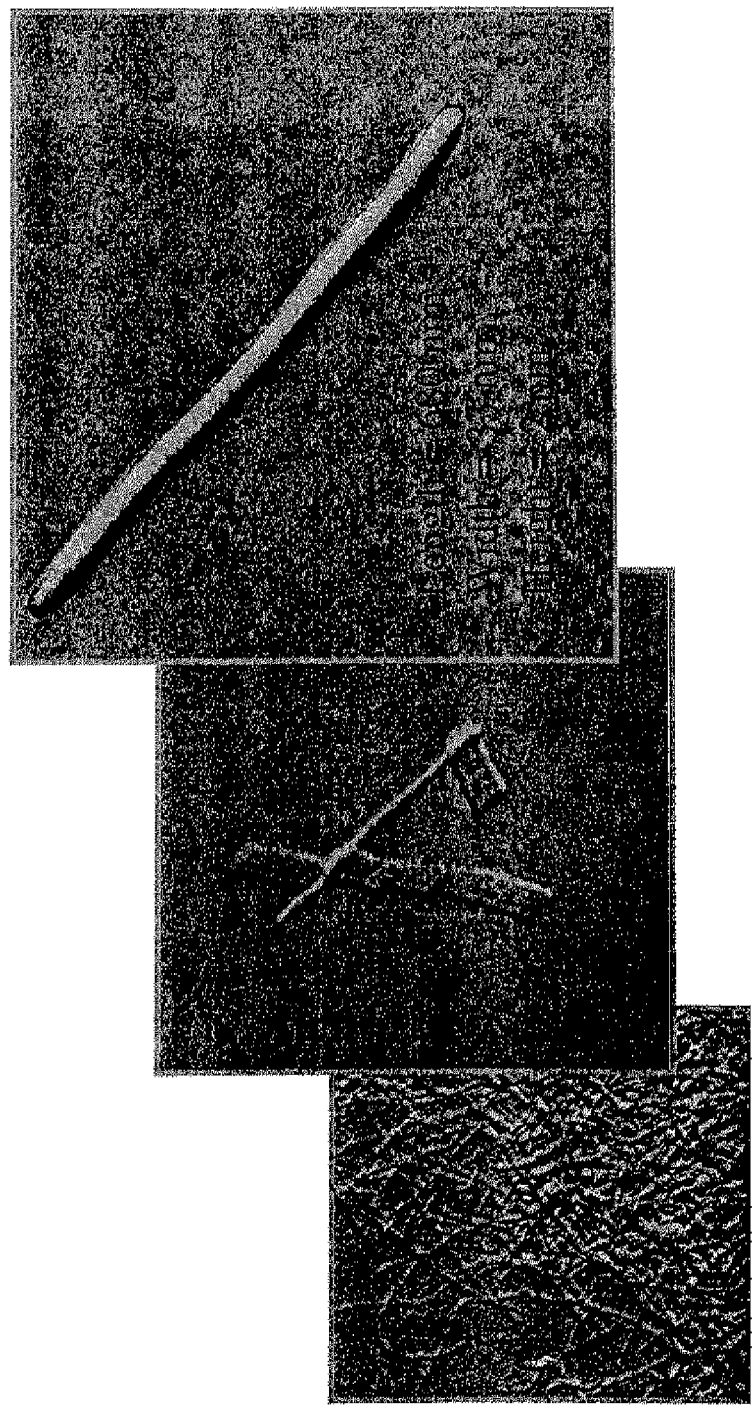
FIG. 2 illustrate AFM image of SELP 47-K film showing self-assembly into nanofilaments.
Figure 3:
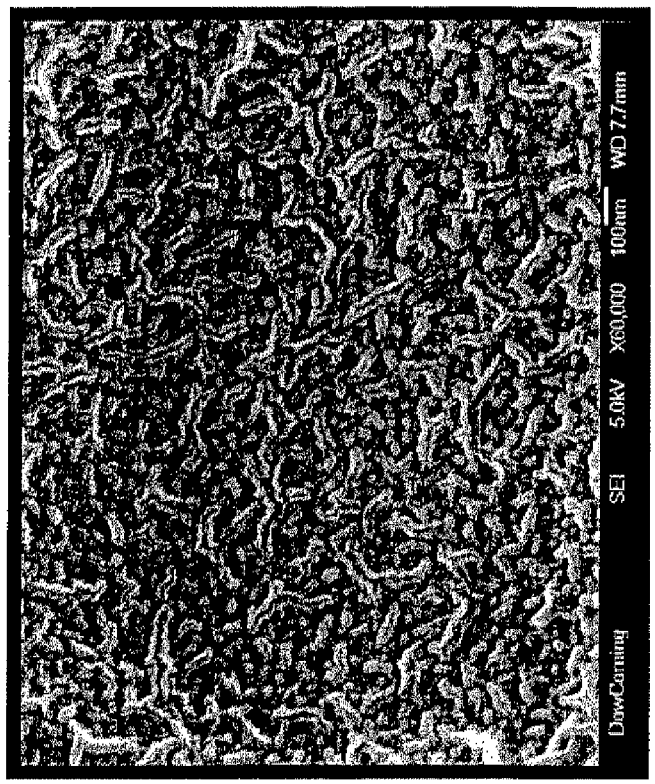
FIG. 3 illustrates SEM image of SELP 47-K film showing self-assembly into nanofilaments.

Four concentrations of the SELP material (13.5%, 1.35%, 0.135% and 0.0135%) were prepared in distilled water and spin-coated on to the surface of a plasma-treated wafer (hydrophilic surface) for examination. FIGS. 2 and 3 provide photomicrographs of SELP 47-K film showing self assembly into nanofilaments.

AFM and SEM examination indicated that there was a coating over the entire surface of the wafer. The coating appeared to be comprised of densely packed intertwining strands. Microscopy results indicated that the SELP47K coating, when concentrated, is comprised of densely packed, long, intertwined strands. Short, single/double strands of material were found in areas where the coating appeared to be less concentrated. Individual strands of material could be seen in the less concentrated, gray areas on the wafer. SEM analysis of the films provide the basis of water-solubility of SELP47K films. A SELP47K film made out of 10% SELP47K solution gave a water-soluble film whereas a 20% solution film was water insoluble. In 10% SELP47K solution film, micellar droplet structures appeared to be responsible for its water solubility whereas 20% SELP47K solution film did not have the micellar droplet structures in the film.

These strands ranged from 100 nm to 1 µm in length and 20-45 nm in diameter. These experiments confirm that SELP47K can be spun into a film and this film when studied using microscopic techniques reveal that film is composed in a non-woven web of filaments. The film is composed of nano filaments. Nano fibers of this protein can be thus utilized in various applications, such as personal care products, due to their strength, advantage of very large surface to mass ratio and protein based targeting characteristics.

Example 11

Preparation of Rinse-Off Conditioners

In this Example, preparation of rinse-off conditioners is described. The compositions for the conditioners are set forth in Table 4.

TABLE 4

Rinse-Off Conditioner Components

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose[1] | 1.5 | 1.5 | 1.5 |
| Cetearyl Alcohol[2] | 1.0 | 1.0 | 1.0 |
| PEG-100 Stearate & Glyceryl Stearate[3] | 1.0 | 1.0 | 1.0 |
| Hydrolyzed Silk Protein[4] | 5.0 | — | — |
| Hydrolyzed Elastin Protein[5] | — | 4.0 | — |
| Pure Polydispersed Silk-Elastin Protein[6] | — | — | 1.0 |
| DMDM Hydantoin[7] | 0.2 | 0.2 | 0.2 |

[1]NATROSOL ® 250 MR (Hercules)
[2]LANETTE O ® (Cognis Corp.)
[3]ARLACEL ® 165 (Uniqema)
[4]Crosilk 10,000 (Croda) Equivalent weight % of protein in conditioner A is 1.0%.
[5]Crolastin (Croda). Equivalent weight % of protein in conditioner B is 1.0%.
[6]Silk Elastin protein prepared in accordance with Example 2. Equivalent weight % of protein in conditioner C is 1.0%.
[7]GLYDANT ® (Lonza)

In order to prepare the compositions, deionized water was added to a mixing vessel and heated to 75° C. With moderate agitation, the hydroxyethyl cellulose was dispersed until fully dissolved. The heat was decreased to 60° C. and cetearyl alcohol and PEG-100 stearate and glyceryl stearate were added. The heat was then decreased to 40° C. and then the protein for either the A, B, or C conditioner was added. The conditioner was mixed for 5-10 minutes and then DMDM hydantoin was added. The water loss was compensated for and the formulation was mixed for an additional 5 minutes. The final pH of the conditioner formulations was approximately 6-7.

Slightly bleached European human hair from International Hair Importer and Products Inc. was used for testing these conditioners. A master hand of hair about eight inches in length was subdivided into a series of individual hair tresses. Each tress weighed about 2.5 grams. A ½ inch portion of the root end of the hair was trimmed and glued to a 2"×2" plastic tab using DUCO CEMENT®. The final weight of each tress was approximately 2.0 g. The cement was allowed to dry, and the hair tress was combed and trimmed to a length so that six inches of hair was extended below the bottom of the plastic tab. A hole was punched in middle of tab ~¼" from the top. Each tress was rinsed for 15 seconds under 40° C. tap water. Using a pipette, 1.0 g of a 9% sodium lauryl sulfate (active) solution was applied and lathered through the tress for 30 seconds. The tress was rinsed for 30 seconds under running water. Excess water was removed from the tress by passing the tress between the index and middle fingers. The tresses were placed on a tray covered with paper towels and dried overnight. Each tress was hand combed three times with the narrow teeth of an ACE) comb and evaluated using the INSTRON® "WET" and the INSTRON® "DRY" COMBING procedures.

For tests involving the rinse-off conditioner, the hair tress was rinsed with tap water for 15 seconds at 40° C. The test conditioner was applied to the tress in the amount of 0.8 g and the tress was stroked for 30 seconds. The tress was rinsed for 30 seconds under tap water at 40° C. The excess water was removed by pulling the tress through the index and middle fingers. The tresses were allowed to dry separately on a paper towel, overnight at room temperature. The tresses were combed once before performing the INSTRON® study.

INSTRON® COMBING is an industry recognized test for determining hair conditioning by the ease of wet combing and the ease of dry combing. The test employs an INSTRON® strain gauge, which is equipped to measure the force required to comb the hair. Conditioning performance is based on the ability of a particular hair treatment formulation such as a shampoo or a hair conditioner to reduce the force required to comb the hair with the INSTRON® strain gauge. The force is reported as Average Combing Load (ACL). The lower ACL value, the better the conditioning effect imparted by the formulation being tested. Typically, ACL baselines are initially established with "untreated" tresses that have only been washed with the sodium lauryl sulfate solution. The effectiveness of a treatment can be expressed as the ACL of the treated tress or the % Reduction in ACL which is calculated by ((untreated hair ACL-treated hair ACL)/untreated hair ACL) *100.

According to the INSTRON® WET COMBING method, the hair was first wet by dipping it in distilled water and then the hair was detangled by combing the tress three times. The tress was then retangled by dipping in distilled water three times. The excess water was removed by passing the tress through index and middle fingers twice. The tress was then placed on the hanger and INSTRON combed. The "retangle" and "INSTRON® combing" steps were repeated until all data points were collected. An average combing force of three tresses was measured for each treatment. The results of the INSTRON® WET COMBING test conducted with the conditioners of the present invention are shown below in Table 5. Letters in the % ACL Reduction column are used to indicate that the product is superior to other designated products at a 90% confidence level. The results show that the performance of the conditioner containing the polydispersed silk elastin compound of the present invention provided a small reduction in dry combing forces compared to the conditioners that contained the hydrolyzed silk and elastin proteins. The performance of these two conditioners actually showed an increase in combing forces compared to the untreated tress.

TABLE 5

INSTRON® WET COMBING

| Conditioner Tested | ACL Reduction (%)[a] |
|---|---|
| A | −22 |
| B | −32 |
| C | 3 (A, B) |

[a]Letter designations indicate that the conditioner was significantly different from the specified conditioners at a 90% confidence level According to the INSTRON® DRY COMBING method, the hair was detangled by combing the tress 3 times. Then, the hair was retangled by swirling the tress clockwise 3 times and counter clockwise 3 times. The tress was then placed on the hanger and INSTRON® combed. The "retangle" and "INSTRON® combing" steps were repeated until all data points were collected. An average combing force of three tresses was measured for each treatment. The results of the INSTRON® DRY COMBING test conducted with the conditioners are shown below in Table 6. The results show that the performance of the silk elastin composition of the present invention provided a larger reduction in dry combing forces compared to the conditioners that contained hydrolyzed silk protein and hydrolyzed elastin proteins, respectively.

TABLE 6

INSTRON® DRY COMBING

| Conditioner Tested | ACL Reduction (%)[a] |
|---|---|
| A | 20 (B) |
| B | −14 |
| C | 33 (A, B) |

[a]Letter designations indicate that the conditioner was significantly different from the specified conditioners at a 90% confidence level.

Additional rinse-off conditioners were also prepared. The compositions of this second set of rinse-off conditioners are set forth in Table 7.

TABLE 7

Second Set of Rinse-Off Conditioners

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose | 1.5 | 1.5 | 1.5 |
| Cetearyl Alcohol | 1.0 | 1.0 | 1.0 |
| PEG-100 Stearate & Glyceryl Stearate | 1.0 | 1.0 | 1.0 |
| Pure Polydispersed Silk-Elastin Protein[1] | 0.01 | — | — |
| Pure Polydispersed Silk-Elastin Protein[1] | — | 0.1 | — |
| Pure Polydispersed Silk-Elastin Protein[1] | — | — | 1.0 |
| DMDM Hydantoin | 0.2 | 0.2 | 0.2 |

[1]Silk-elastin protein prepared in accordance with Example 2.

INSTRON® wet and dry combing tests were performed using this second set of rinse-off conditioners, as described above. The INSTRON® combing results in Tables 8 and 9 show the effect of concentration for the pure, polydispersed silk elastin protein compound. Table 9 shows that the performance of the protein material provided a reduction in dry combing force at a concentration as low as 0.1% in the rinse-off conditioner formulation, thereby improving the conditioning properties of the hair.

TABLE 8

INSTRON® WET COMBING

| Conditioner Tested | ACL Reduction (%)[a] |
|---|---|
| A | −25 |
| B | −2 |
| C | 3 |

TABLE 9

INSTRON® DRY COMBING

| Conditioner Tested | ACL Reduction (%)[a] |
|---|---|
| A | −5 |
| B | 11 |
| C | 33 (A) |

[a]Letter designation indicates that the conditioner is significantly different to the specified conditioner at a 95% confidence level.

An additional set of rinse-off conditioners were prepared. The compositions of this third set of rinse-off conditioners are set forth in Table 10.

TABLE 10

Third Set of Rinse-Off Conditioners

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose | 1.5 | 1.5 | 1.5 |
| Cetearyl Alcohol | 1.0 | 1.0 | 1.0 |
| PEG-100 Stearate & Glyceryl Stearate | 1.0 | 1.0 | 1.0 |
| Pure Monodispersed Silk Elastin Protein[1] | 0.01 | — | — |
| Pure Monodispersed Silk Elastin Protein[1] | — | 0.1 | — |
| Pure Monodispersed Silk Elastin Protein[1] | — | — | 1.0 |
| DMDM Hydantoin | 0.2 | 0.2 | 0.2 |

[1]Silk Elasin protein prepared in accordance with Example 1.

INSTRON® wet and dry combing tests were performed in conjunction with the procedures described above. The INSTRON® combing results in Tables 11 and 12 show the effect of concentration for the pure, monodispersed silk elastin protein compound. Table 12 shows that the performance of the protein material provided a small reduction in dry combing force at all concentrations in the rinse-off conditioner formulation, thereby improving the conditioning properties of the hair.

TABLE 11

INSTRON® WET COMBING

| Conditioner Tested | ACL Reduction (%)[a] |
|---|---|
| A | −17 |
| B | −4 |
| C | −49 |

[a]Letter designation indicates that the conditioner was significantly different from the specified conditioner at a 95% confidence level.

TABLE 12

INSTRON® DRY COMBING

| Conditioner Tested | ACL Reduction (%) |
|---|---|
| A | 10 |
| B | 9 |
| C | 5 |

Example 12

Efficacy Studies of SELP47K Applied to Skin

This Example describes experiments conducted in an efficacy study to measure changes in the biomechanical properties of skin and the ability of a single application of SELP to diminish the visual effects of aging on skin.

Eleven impaneled subjects (age 35-70 years) showing clear signs of facial skin aging were provided with a non-moisturizing soap, (AVEENO®), one week prior to the study and were instructed to use the provided soap to wash the face and were required to refrain from excessive UV exposure. After a seven-day conditioning phase, subjects were acclimated to the ambient temperature and humidity for thirty minutes. One side of the face of each subject was designated as the measurement side by random selection by computer. After 30-minute acclimation period, baseline digital photographs were taken, and instrumental measurements, skin replica samples and visual evaluations were made. Photographs were taken, with a Canfield Scientific Camera, of the full face, the periorbital area, and the temporal side of eye. Chromameter (Model CR300, Minolta) measurements were taken from the periorbital area directly under the eye (Chardon et aL, Int. J. Cosmet. Sci., 13:191-208 [1991]). Silflo replicas (CuDerm Corporation, Dallas, Tex.) were made from the periorbital area adjacent to the temporal side of the eye (Grove et al., J. Am. Acad. Dermatol., 21:631-637 [1998]; and Sun et al 1997 IFSCC Conference, Mexico). Cutometer (SEM575, Courage and Khazaka, Germany) measurements were taken at the periorbital area at the upper portion of cheekbone. All measurements were performed in triplicate. An assessment of the relative depth and frequency of facial lines was performed by the method of Packman and Gans (Packman and Gans, J. Soc. Cosmet. Chem., 29:79-90 [1978]).

After baseline control data were collected, 5% SELP47K aqueous solution was applied to the face of each subject. A few drops of the SELP47K solution was dispensed onto the fingertips and smoothed into the skin of the face. Subjects were retained in the lab for 30 minutes after application of the SELP47K aqueous solution, at which point a second set of measurements were made.

Image analysis of Silflo replicas was done. Specifically, the fine line factors, which approximate the number and/or length of facial lines in the 10 evaluated bands of skin replica, were measured. At 30 minutes after application of SELP47K, fine line factors decreased by a statistically significant 13% (p=0.05). The statistical comparisons of the fine lines factors are summarized in Table 13.

TABLE 13

Statistical Comparisons of Fine Lines Factors

| | Fine Line Factors | |
|---|---|---|
| | Baseline | 30 Minutes Post |
| Mean | 284 | 246 |
| Variance | 1584 | 2538 |
| Observations | 11 | 11 |
| Pearson Correlation | 0.16 | |
| Hypothesized Mean | 0 | |
| df | 10 | |
| t Stat | 2.18 | |
| P (T <= t) one-tail | 0.03 | |
| t Critical one-tail | 1.81 | |
| P (T <= t) two-tail | 0.05 | |
| t Critical two-tail | 2.23 | |

Evaluation of superficial facial lines was performed by an expert evaluator using the scoring method described by Packman and Gans (supra). A 7% decrease in the superficial facial line score was assessed at the 30-minute post-treatment interval compared to baseline, which was statistically significant at the 91% confidence level (p=0.09). The statistical comparisons of these measured values are summarized in Table 14.

TABLE 14

Statistical Analysis of Superficial Facial Line Scores

|  | Superficial Facial Line Score | |
| --- | --- | --- |
|  | Baseline | 30 Minutes Post |
| Mean | 40 | 37 |
| Variance | 640 | 660 |
| Observations | 11 | 11 |
| Pearson Correlation | 0.98 | |
| Hypothesized Mean | 0 | |
| df | 10 | |
| t Stat | 1.90 | |
| P (T <= t) one-tail | 0.04 | |
| t Critical one-tail | 1.81 | |
| P (T <= t) two-tail | 0.09 | |
| t Critical two-tail | 2.23 | |

Chromometer values for L*, a*, and b* were read and total color value, E, was calculated for each subject. The average a* value (which is directly related to the redness of the skin) decreased with statistical significance by 6% relative to baseline (p=0.024) as shown in Table 15.

TABLE 15

Chromameter Scores

|  | Chromameter a* Score | |
| --- | --- | --- |
|  | Baseline | 30 Minutes Post |
| Mean | 11.05 | 10.39 |
| Variance | 2.08 | 2.74 |
| Observations | 11 | 11 |
| Pearson Correlation | 0.86 | |
| Hypothesized Mean | 0 | |
| df | 10 | |
| t Stat | 2.66 | |
| P (T <= t) one-tail | 1.20E–02 | |
| t Critical one-tail | 1.81 | |
| P (T <= t) two-tail | 2.39E–02 | |
| t Critical two-tail | 2.23 | |

Cutometer results showed an increase in Uv (a measure of viscoelasticity and delayed distention of the skin), indicating an increase in skin softness, and was assessed at a statistical confidence level of 91% (p=0.09) as shown in Table 16.

TABLE 16

Cutometer Scores

|  | Cutometer Uv Score | |
| --- | --- | --- |
|  | Baseline | 30 Minutes Post |
| Mean | 0.09 | 0.106 |
| Variance | 0.000 | 0.001 |
| Observations | 11 | 11 |
| Pearson Correlation | 0.06 | |
| Hypothesized Mean | 0 | |
| df | 10 | |
| t Stat | –1.88 | |
| P (T <= t) one-tail | 0.04 | |
| t Critical one-tail | 1.81 | |
| P (T <= t) two-tail | 0.09 | |
| t Critical two-tail | 2.23 | |

In summary, as observed in the above experiments, the foremost effects of a single treatment with 5% aqueous solution of SELP47K were reductions in both the appearance and the measured number and/or length of fine lines in the periorbital area of the face as well as an indication of improved skin softness and the evenness of tone.

Example 13

Personal Care Compositions

This Example provides various personal care compositions comprising any of the compounds

| BODY WASH | | | |
| --- | --- | --- | --- |
| BODY WASH RAW MATERIAL (INCI Designation) | pH 6.5 Amount | PH 7 Amount | PH 8 Amount |
| Deionized water | QS | QS | QS |
| Sodium Laureth Sulfate | 12 | 15 | 8 |
| Cocamidopropyl Betaine | 8 | 10 | 15 |
| DecylAPG Glucoside (Plantacare 2000 1) | 0 | 2 | 1 |
| Polyquaternium-10 (JR30M) | 0.25 | 0 | 0 |
| Polyquaternium-7 (Mackam 55) | 0 | 0 | 0.7 |
| Preservative, fragrance, color | QS | QS | QS |
| MOISTURIZING BODYWASH RAW MATERIAL (INCI Designation) | pH = 7 Amount | | |
| Deionized Water | QS | | |
| Glycerin | 4.0 | | |
| PEG-6 Caprylic/Capric Glycerides | 4.0 | | |
| Palm Kernel Fatty acids | 3.0 | | |
| Sodium Laureth-3 Sulfate | 45.0 | | |
| Cocamide MEA | 3.0 | | |
| Sodium Lauroamphoacetate | 25.0 | | |
| Soyabean Oil | 10.0 | | |
| Polyquaternium-10 (JR30M) | 0.70 | | |
| Preservative, fragrance, color | QS | | |
| Repeat Sequence Protein Polymer | 1000 ppm | | |
| Repeat Sequence Protein Polymer | 250 ppm | 500 ppm | 1000 ppm |

| BODY LOTION RAW MATERIAL (INCI Designation) | pH 7 Amount | pH 7 Amount | pH 7.5 Amount | pH 7 Amount |
| --- | --- | --- | --- | --- |
| Deionized Water | QS | QS | QS | QS |
| Glycerine | 8 | 8 | 10 | 12 |
| Isohexadecane | 3 | 3 | 3 | 6 |
| Niacinamide | 0 | 3 | 5 | 6 |
| Isopropyl Isostearate | 3 | 3 | 3 | 3 |
| Polyacrylamide (and), Isoparaffin, (and) Laureth-7 (Sepigel 305[2]) | 3 | 3 | 3 | 3 |

-continued

| BODY LOTION RAW MATERIAL (INCI Designation) | pH 7 Amount | pH 7 Amount | pH 7.5 Amount | pH 7 Amount |
|---|---|---|---|---|
| Petrolatum | 4 | 4 | 4 | 2 |
| Nylon 12 | 2 | 2 | 2.5 | 2.5 |
| Dimethicone (DC1403[4]) | 2 | 2 | 2.5 | 2.5 |
| Sucrose Polycottonseed Oil | 1.5 | 1.5 | 1.5 | 1.5 |
| Stearyl Alcohol 97% | 1 | 1 | 1 | 1 |
| D Panthenol | 1 | 1 | 1 | 1 |
| DL-alphaTocophero Acetate | 1 | 1 | 1 | 1 |
| Cetyl Alcohol 95% | 0.5 | 0.5 | 0.5 | 1 |
| Behenyl Alcohol | 1 | 1 | 1 | 0.5 |
| Cetearyl Alcohol (and) Cetearyl GlucosidePL 68/50 | 0.4 | 0.4 | 0.5 | 0.5 |
| Stearic Acid | 0.15 | 0.15 | 0.15 | 0.15 |
| PEG-100-Stearate (MYRJ 59[1]) | 0.15 | 0.15 | 0.15 | 0.15 |
| Preservative, fragrance, color | QS | QS | QS | QS |
| Repeat sequence protein polymers | 250 ppm | 500 ppm | 750 ppm | 1000 ppm |

| LEAVE-ON HAIR CONDITIONER RAW MATERIAL (INCI Designation) | Amount |
|---|---|
| Deionized Water | QS |
| Isostearamidopropyl Morpholine Lactate | 6.0 |
| Hydroxyethylcellulose | 1.0 |
| Preservative, fragrance, color | QS |
| Repeat sequence protein polymers | 1000 ppm |

| CONDITIONING SHAMPOO RAW MATERIAL (INCI Designation) | Amount |
|---|---|
| Deionized Water | QS |
| Sodium Laureth Sulfate 30% | 27.0 |
| Cocamidopropyl Betaine | 3.7 |
| Coco-Glucoside (and) Glyceryl Oleate | 5.0 |
| Coco-Glucoside (and) Glycol Distearate (and) Glycerine | 3.0 |
| Guar Hydroxypropyl Trimonium Chloride | 0.1 |
| Laureth-2 | 1.55 |
| Fragrance, preservative, color | QS |
| Repeat sequence protein polymer | 1000 ppm |

| CREAM RINSE RAW MATERIAL (INCI Designation) | pH 4 Amount |
|---|---|
| Deionized Water | QS |
| Behentrimonium Chloride | 2.0 |
| Trilaureth-4 Phosphate | 1.5 |
| Cetyl alcohol | 2.0 |
| Citric acid | QS |
| Preservative, fragrance, color | QS |
| Repeat sequence protein polymer | 1000 ppm |

| NOURISHING HAIR CONDITIONER/TREATMENT RAW MATERIAL (INCI Designation) | pH 6 Amount |
|---|---|
| Deionized Water | QS |
| Behentrimonium Methosulfate (and) Cetyl Alcohol | 4.0 |
| Wheat germ oil | 1.0 |
| Cetyl alcohol | 0.5 |
| Propylene glycol | 5.0 |
| PEG-60 Lanolin | 1.0 |
| Panthenol | 2.0 |
| Lupin amino acids | 1.0 |
| Cocodimonium Hydroxypropyl Hydrolyzed Wheat Protein | 1.0 |
| Fragrance, preservative, color | QS |
| Repeat sequence protein polymer | 1000 ppm |

| ANTI-DANDRUFF SHAMPOO RAW MATERIAL (INCI Designation) | Amount |
|---|---|
| Deionized Water | QS |
| Magnesium Aluminum Silicate | 1.0 |
| Hydroxypropyl Methylcellulose | 0.8 |
| Sodium Olefin Sulfate 40% | 35.0 |
| Lauramide DEA | 4.0 |
| Soyamide DEA | 1.0 |
| Quaternium-70 Hydrolyzed Collagen | 2.0 |
| Zinc Pyrithione 40% | 4.0 |
| Fragrance, preservative, color | QS |
| Repeat sequence protein polymer | 1000 ppm |

| ULTRA-HIGH MOISTURIZING FACIAL CREAM/LOTION EMULSION RAW MATERIAL (INCI Designation) | pH 7 Amount | pH 7 Amount |
|---|---|---|
| Deionized water | QS | QS |
| Glycerin | 12 | 5 |
| PEG 400[6] | 0 | 10 |
| Niacinamide | 5 | 7 |
| Isohexadecane | 5 | 5 |
| Dimethicone (DC1403[3]) | 3 | 2 |
| Polyacrylamide (and), Isoparaffin (and), Laureth-7 (Sepigel 305[1]) | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Vitamin E (Tocopherol Acetate) | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate (Myrj 59[4]) | 0.15 | 0.15 |
| Preservative, fragrance, color | QS | QS |
| Repeat sequence protein polymer | 250 ppm | 1500 ppm |

| MOISTURIZING CREAM RAW MATERIAL (INCI Designation) | pH 7 Amount | pH 7 Amount | pH 7.5 Amount |
|---|---|---|---|
| Deionized water | QS | QS | QS |
| Glycerine | 3 | 5 | 10 |
| Petrolatum | 3 | 3 | 0 |
| Cetyl Alcohol 95% | 1.5 | 1.5 | 1 |

MOISTURIZING CREAM

| RAW MATERIAL (INCI Designation) | pH 7 Amount | pH 7 Amount | pH 7.5 Amount |
|---|---|---|---|
| Dimethicone Copolyol (DC 3225C[4]) | 2 | 2 | 2 |
| Isopropyl Palmitate | 1 | 1 | 0.5 |
| Carbopolmer 954 (Noveon) | 0.7 | 0.7 | 0.7 |
| Dimethicone (DC 200/350cs[4]) | 1 | 1 | 1 |
| Stearyl Alcohol 97% | 0.5 | 0.5 | 1 |
| Stearic acid | 0.1 | 0.1 | 0.1 |
| PEG-100-stearate (MYRJ 59[1]) | 0.1 | 0.1 | 0.1 |
| Titanium Dioxide | 0.3 | 0.3 | 0.3 |
| Preservative, color, fragrance | QS | QS | QS |
| Repeat sequence protein polymer | 50 ppm | 250 ppm | 1000 ppm |

FACIAL CLEANSING EMULSION

| RAW MATERIAL (INCI Designation) | Amount |
|---|---|
| Water | 69.05 |
| Disodium EDTA | 0.1 |
| Glyceryl polymethacrylate (and) Propylene glycol | 1.0 |
| Glycerin | 2.0 |
| Xanthan gum | 0.5 |
| Hydroxyethyl cellulose | 0.5 |
| Tridecyl neopentanoate | 4.0 |
| Isocetyl stearate | 6.0 |
| Octyl palmitate | 8.0 |
| Glyceryl dilaurate | 4.0 |
| PEG-20 stearate | 2.0 |
| Glyceryl stearate (and) Laureth-23 | 2.0 |
| Lauryl pyrrolidone | 0.5 |
| *Chamomile* extract | 0.2 |
| *Aloe vera* (200x) | 0.05 |
| Fragrance, preservative | QS |
| Repeat sequence protein polymer | 0.1 |

SURFACTANT-BASED FACIAL CLEANSER

| RAW MATERIAL (INCI Designation) | Amount |
|---|---|
| Water | 62.55 |
| Acrylates/Steareth-20 methacrylate copolymer | 3.3 |
| Disodium EDTA | 0.05 |
| Glycerin | 2.0 |
| Glyceryl polymethacrylate (and) Propylene glycol (and) PVM/MA copolymer | 0.5 |
| Sodium laureth sulfate (30%) | 17.5 |
| Cetearyl alcohol | 1.0 |
| Shea butter | 1.0 |
| Disodium oleamido PEG-2 sulfosuccinate | 5.0 |
| Cocoamidopropyl Betaine | 3.0 |
| Sodium lauroyl sarcosinate | 1.0 |
| PEG-7 glyceryl cocoate | 1.0 |
| Isodecyl oleate | 1.5 |
| Peppermint extract | 0.25 |
| Eucalyptus extract | 0.25 |
| Fragrance, preservative, color, pH adjust | QS |
| Repeat sequence protein polymer | 0.1 |

FACIAL EXFOLIATING GEL

| RAW MATERIAL (INCI Designation) | Amount |
|---|---|
| Water | 64.39 |
| Disodium EDTA | 0.05 |
| *Aloe vera* (200x) | 0.01 |
| Benzophenone-4 | 0.25 |
| Propylene glycol | 1.0 |
| Acrylates/C10-30 alkyl acrylate crosspolymer (2%) | 20.0 |
| Glyceryl polymethacrylate (and) Propylene glycol | 10.0 |
| Glyceryl polymethacrylate (and) Propylene glycol (and) PVM/MA copolymer | 1.0 |
| Hydrogenated jojoba oil | 1.5 |
| Fragrance, preservative, color, pH adjust | QS |
| Repeat sequence protein polymer | 0.05 |

FACIAL TONER

| RAW MATERIAL (INCI Designation) | Amount |
|---|---|
| Water | 93.99 |
| Disodium EDTA | 0.1 |
| Butylene glycol | 2.0 |
| *Aloe vera* (200x) | 0.1 |
| Allantoin | 0.1 |
| Benzophenone-4 | 0.5 |
| Witch hazel extract | 0.3 |
| Propylene glycol (and) *Euphrasia* extract (and) Golden seal root extract (and) Green tea extract | 0.01 |
| PEG-40 hydrogenated castor oil | 0.5 |
| Quaternium-22 | 0.5 |
| Sandlewood oil | 0.02 |
| Fragrance, preservative, color, pH adjust | QS |
| Repeat sequence protein polymer | 0.05 |

EXFOLIATING CREAM

| RAW MATERIAL (INCI Designation) | Amount |
|---|---|
| Water | 68.80 |
| Disodium EDTA | 0.1 |
| PVM/MA decadiene crosspolymer | 1.0 |
| Butylene glycol | 3.0 |
| PEG-20 stearate | 1.0 |
| Glyceryl stearate (and) Laureth-23 | 2.0 |
| Diisopropyl adipate | 2.0 |
| Isodecyl oleate | 2.0 |
| Isocetyl stearoyl stearate | 5.0 |
| Myristyl myristate | 1.0 |
| Glyceryl dilaurate | 2.0 |
| Sodium hydroxide, 10% | 2.6 |
| Glyceryl polymethacrylate (and) Propylene glycol | 5.0 |
| Glyceryl polymethacrylate (and) Propylene glycol (and) PVM/MA copolymer | 0.5 |
| Hydrogenated jojoba oil | 3.0 |
| Fragrance, preservative, color, pH adjust | QS |
| Repeat sequence protein polymer | 0.05 |

FACIAL MASK

| RAW MATERIAL (INCI Designation) | Amount |
|---|---|
| Water | 76.4 |
| Disodium EDTA | 0.1 |
| Bentonite | 12.5 |
| Potassium C12-13 Alkyl Phosphate | 5.0 |
| Propylene glycol | 4.0 |
| Sodium Coco PG-Dimonium Chloride Phosphate | 1.0 |
| Fragrance, preservative, color, pH adjust | QS |
| Repeat sequence protein polymer | 0.05 |

AFTER SHAVE BALM

| RAW MATERIAL (INCI Designation) | Amount |
|---|---|
| Water | 82.12 |
| Disodium EDTA | 0.1 |
| Acrylate copolymer | 2.0 |
| Acrylate/Stareth-20 methacrylate copolymer | 1.0 |
| Propylene glycol | 3.0 |
| Sodium hydroxide (10%) | 1.28 |
| Glyceryl stearate (and) Cetyl alcohol (and) Stearyl alcohol (and) Behenyl alcohol (and) Palmitic acid (and) Stearic acid (and) Hydroxyethyl cetearamidopropyldimonium chloride | 3.5 |
| Isocetyl stearate | 1.0 |
| C12-15 alkyl lactate | 1.5 |
| Octyldodecyl stearate | 3.0 |
| Glyceryl polymethacrylate (and) Propylene glycol (and) PVM/MA copolymer | 1.0 |
| Polyquaternium-11 | 0.5 |
| Fragrance, preservative, color, pH adjust | QS |
| Repeat sequence protein polymer | 0.1 |

EYE GEL

| RAW MATERIAL (INCI Designation) | Amount |
|---|---|
| Water | 89.14 |
| VP/Acrylates/Lauryl methacrylate copolymer | 0.5 |
| Glycerin | 5.0 |
| Aminomethyl propanol | 0.3 |
| *Aloe vera* (200x) | 0.05 |
| Benzophenone-4 | 0.1 |
| Glyceryl polymethacrylate (and) Propylene glycol (and) PVM/MA copolymer | 0.2 |
| Butylene glycol (and) Water (and) Witch hazel extract | 0.5 |
| Butylene glycol (and) Water (and) Cucumber extract | 0.3 |
| PEG-40 hydrogenated castor oil | 0.01 |
| Acrylates/Beheneth-25 methacrylate copolymer | 2.4 |
| Fragrance, preservative, color, pH adjust | QS |
| Repeat sequence protein polymer | 1.0 |

HIGH MELTING POINT LIPSTICK

| RAW MATERIAL (INCI Designation) | Amount |
|---|---|
| Ozokerite wax | 5.0 |
| Candelilla wax | 11.0 |
| Octyl dodecanol | 26.0 |
| C30-45 alkyl methicone | 5.0 |
| Cyclomethicone | 4.8 |

HIGH MELTING POINT LIPSTICK

| RAW MATERIAL (INCI Designation) | Amount |
|---|---|
| Petrolatum | 3.0 |
| Lanolin oil | 9.0 |
| Avocado oil | 2.0 |
| Oleyl alcohol | 8.0 |
| Pigment/cyclomethicone | 25.0 |
| Fragrance, preservative | QS |
| Repeat sequence protein polymer | 1.0 |

LIPSTICK

| RAW MATERIAL (INCI Designation) | Amount |
|---|---|
| Candelilla wax | 9.1 |
| Isopropyl myristate | 9.6 |
| Lanolin | 5.0 |
| Beeswax | 4.0 |
| Paraffin (130/135) | 2.0 |
| Ozokerite wax | 2.5 |
| Castor oil | 53.7 |
| Carnauba wax | 1.5 |
| Pigments | 7.5 |
| Mineral oil | 4.0 |
| Fragrance, preservative | QS |
| Repeat sequence protein polymer | 1.0 |

LIP GLOSS

| RAW MATERIAL (INCI Designation) | Amount |
|---|---|
| Bis-diglyceryl polyacyladipate-1 | 43.5 |
| Bis-diglyceryl polyacyladipate-2 | 10 |
| Glycerol ricinoleate | 10 |
| Polyisobutene 1000 | 13 |
| Lanolin wax | 10 |
| Candelilla wax | 2.5 |
| Mica (and) titanium dioxide | 3 |
| d-Panthenol | 5 |
| Fragrance, preservative, color | QS |
| Repeat sequence protein polymer | 1.0 |

LIP GLOSS WITH SUNSCREEN

| RAW MATERIAL (INCI Designation) | Amount |
|---|---|
| Triisostearyl Citrate | 58.4 |
| Candelilla wax | 8.0 |
| Myristyl lactate | 7.5 |
| Microcrystalline wax | 5.0 |
| Carnauba wax | 2.0 |
| Diisopropyl dimmer dilinoleate | 10.0 |
| Mica (and) Bismuth oxychloride (and) Carmine | 6.0 |
| Zinc oxide (microfine) | 2.0 |
| Fragrance, preservative | QS |
| Repeat sequence protein polymer | 1.0 |

LIP BALM

| RAW MATERIAL (INCI Designation) | Amount |
|---|---|
| Petrolatum | 47.3 |
| Isopropyl lanolate | 6.0 |
| Ozokerite wax | 16.5 |
| Candelilla wax | 4.5 |
| Diisopropyl dilinoleate | 25.0 |
| Retinyl palmitate | 0.5 |
| Tocopherol acetate | 0.2 |
| Fragrance, preservative | QS |
| Repeat sequence protein polymer | 1.0 |

WATERPROOF MASCARA

| RAW MATERIAL (INCI Designation) | Amount |
|---|---|
| Water | 49.45 |
| Propylene glycol | 3.0 |
| Triethanolamine (99%) | 3.1 |
| Acrylates/Octylacrylamine Copolymer | 5.0 |
| Diisostearoyl trimethylolpropane siloxy silicate | 5.0 |
| Candelilla wax | 4.5 |
| Beeswax | 5.5 |
| Ozokerite wax | 2.0 |
| Carnauba wax | 1.0 |
| Cetyl alcohol | 3.0 |
| Stearic acid | 5.0 |
| Iron oxides | 11.0 |
| Fragrance, preservative | QS |
| Repeat sequence protein polymer | 2.0 |

ANHYDROUS WATERPROOF MASCARA

| RAW MATERIAL (INCI Designation) | Amount |
|---|---|
| C9-11 Isoparaffin | 30.95 |
| Polyethylene | 11.0 |
| Candelilla wax | 4.5 |
| Hydroxylated lanolin | 0.25 |
| Pentaerythrityl rosinate | 2.0 |
| Zinc stearate | 1.0 |
| Silica silylate | 1.0 |
| Petroleum distillates (and) Quaternium-18 hectorite (and) Propylene Carbonate | 35.0 |
| Iron oxides | 12.0 |
| Fragrance, preservative | QS |
| Repeat sequence protein polymer | 2.0 |

WATER-BASED MASCARA

| RAW MATERIAL (INCI Designation) | Amount |
|---|---|
| Water | 43.32 |
| Polyvinyl pyrrolidone (K30) | 2.0 |
| Hydroxyethyl cellulose | 1.0 |
| Triethanolamine (99%) | 2.0 |
| Disodium EDTA | 0.1 |
| Iron Oxides | 10.0 |
| Stearic acid | 4.5 |
| Glyceryl monostearate | 2.0 |
| Beeswax | 7.0 |

WATER-BASED MASCARA

| RAW MATERIAL (INCI Designation) | Amount |
|---|---|
| Carnauba wax | 4.5 |
| Hydroxylated lanolin | 1.0 |
| Acrylates copolymer | 20.0 |
| Fragrance, preservative | QS |
| Repeat sequence protein polymer | 2.0 |

LIQUID EYELINER

| RAW MATERIAL (INCI Designation) | Amount |
|---|---|
| Water | 50-70 |
| Gellant | 0.5-1.5 |
| Wetting agent(s) | 1-3 |
| Polyol | 4-8 |
| Colorants | 10-20 |
| Alcohol | 5-10 |
| Film former | 3-8 |
| Fragrance, preservative | QS |
| Repeat sequence protein polymer | 2.0 |

NAIL ENAMEL

| RAW MATERIAL (INCI Designation) | Amount |
|---|---|
| Solvent(s) | 40-70 |
| Resin(s) | 10-20 |
| Plasticizer | 3-12 |
| Gellant | 0-2 |
| Colorants | 0-3 |
| Fragrance, preservative | QS |
| Repeat sequence protein polymer | 2.0 |

CUTICLE TREATMENT

| RAW MATERIAL (INCI Designation) | Amount |
|---|---|
| Petrolatum | 34.8 |
| Beeswax | 7.2 |
| Ozokerite wax | 4.3 |
| Candelilla wax | 4.0 |
| Cocoa butter | 1.0 |
| Shea butter | 1.0 |
| Glyceryl dilaurate | 8.0 |
| Ethylhexyl palmitate | 20.0 |
| C12-15 alkyl lactate | 6.0 |
| PVP/Eicosene copolymer | 3.5 |
| Diisopropyl adipate | 2.0 |
| Octinoxate | 7.5 |
| Retinyl palmitate | 0.1 |
| Tocopherol acetate | 0.1 |
| Fragrance, preservative, color, pH adjust | QS |
| Repeat sequence protein polymer | 0.5 |

PRESSED POWDER FORMULATIONS

| | Loose Powder | Pressed Powder | Foundation | Blush | Eye Shadow |
|---|---|---|---|---|---|
| Fillers (eg. talc, mica, seracite) | 70-95 | 40-90 | 40-80 | 40-80 | 40-80 |
| Compression aids (e.g., metallic soaps, waxes) | 0-2.5 | 3-5 | 2-5 | 2-7 | 2-10 |
| Texture enhancers | 10-40 | 5-40 | 10-40 | 10-40 | 0-30 |
| Colorants (e.g., iron oxides, organic colors) | 2-10 | 2-10 | 5-20 | 2-10 | 1-40 |
| Pearls (e.g. titanated mica, bismuth oxychloride) | 0-20 | 0-10 | 0-5 | 0-20 | 0-60 |
| Wet binder (e.g., Octyldodecyl stearoyl stearate, di-PPG3 myristyl ether adipate, isocetyl stearate, cetyl dimethicone) | 0-3 | 2-5 | 2-5 | 3-10 | 3-15 |
| Dry binder (e.g., calcium silicate, kaolin) | 0-2 | 2-5 | 2-5 | 3-8 | 3-8 |
| Fragrance, preservative | QS | QS | QS | QS | QS |
| Repeat sequence protein polymer | 2 | 2 | 2 | 2 | 2 |

WATER-IN-OIL FOUNDATION

| RAW MATERIAL (INCI Designation) | Amount |
|---|---|
| Cyclomethicone | 12.0 |
| Dimethicone | 5.0 |
| Cyclomethicone (and) Dimethicone copolyol | 20.0 |
| Laureth-7 | 0.5 |
| Colorants (hydrophobically treated) | 2.2 |
| Titanium dioxide (and) methicone | 8.5 |
| Talc (and) methicone | 3.3 |
| Water | 37.2 |
| Sodium chloride | 2.0 |
| Propylene glycol | 8.0 |
| Fragrance, preservative | QS |
| Repeat sequence protein polymer | 1 |

ANHYDROUS MAKEUP STICK

| RAW MATERIAL (INCI Designation) | Amount |
|---|---|
| Ozokerite wax | 5.6 |
| Polyethylene | 5.3 |
| Glyceryl dilaurate | 5.5 |
| Isostearyl neopentanoate | 13.0 |
| Octyldodecyl stearoyl stearate | 12.0 |
| Myristyl myristate | 11.0 |
| Ethylhexyl methoxycinnamate | 7.5 |
| PVP/Eicosene copolymer | 0.5 |
| Tocopherol acetate | 0.1 |
| Dimethicone (and) Trimethylsiloxysilicate | 8.0 |
| Cyclopentasiloxane | 9.0 |
| Mica | 10.0 |
| Talc | 1.7 |
| Titanium dioxide (and) Isopropyl titanium triisostearate | 8.86 |
| Iron oxides (and) Isopropyl titanium triisostearate | 1.94 |
| Fragrance, preservative | QS |
| Repeat sequence protein polymer | 1.0 |

WATER-IN-SILICONE FOUNDATION

| RAW MATERIAL (INCI Designation) | Amount |
|---|---|
| Cetyl dimethicone copolyol | 0.45 |
| Polyglycerol-4 isostearate (and) Cetyl dimethicone copolyol (and) Hexyl laurate | 1.75 |
| Polyalkylene polysiloxane copolymer | 0.9 |
| Cetyl dimethicone | 0.9 |
| Beeswax | 0.7 |
| Castor wax (and) hydrogenated castor oil | 0.35 |
| Octyl palmitate | 7.0 |
| Cyclomethicone | 7.95 |
| Phenyl trimethicone | 2.2 |
| Titanium dioxide (and) Caprylyl silane | 7.5 |
| Iron oxides (and) Caprylyl silane | 1.1 |
| Talc (and) Caprylyl silane | 3.8 |
| Cyclomethicone | 7.95 |
| Dimethicone | 1.3 |
| Water | 49.55 |
| Sodium chloride | 0.5 |
| Propylene glycol | 5.3 |
| Fragrance, preservative | QS |
| Repeat sequence protein polymer | 0.5 |

OIL-IN-WATER FOUNDATION

| RAW MATERIAL (INCI Designation) | Amount |
|---|---|
| Water | 59.85 |
| Polyvinylpyrrolidone | 5.0 |
| Magnesium aluminum silicate | 2.0 |
| Xanthan gum | 0.4 |
| Trisodium EDTA | 0.05 |
| Glyceryl polymethacrylate (and) Propylene glycol (and) PVM/MA copolymer | 1.0 |
| Polysorbate 20 | 1.0 |
| Kaolin | 0.8 |
| Butylene glycol | 4.0 |
| Titanium dioxide | 6.05 |
| Iron oxides | 1.15 |
| Dimethicone | 6.0 |
| Ethylhexyl palmitate | 2.0 |
| PEG/PPG-25/25 Dimethicone | 1.0 |
| Tocopherol acetate | 0.1 |
| Retinyl palmitate | 0.1 |
| Silica | 3.0 |
| Cyclopentasiloxane | 5.0 |
| Fragrance, preservative | QS |
| Repeat sequence protein polymer | 1.0 |

SUNSCREEN FORMULAS

| RAW MATERIAL (INCI Designation) | Amount SPF ~25 | SPF ~15 |
|---|---|---|
| Water | 52.65 | 71.10 |
| PVM/MA decadiene crosspolymer | 0.5 | 0.5 |
| Butylene glycol | 3.0 | 3.0 |
| Disodium EDTA | 0.1 | 0.1 |
| PEG-20 stearate | 1.5 | 1.5 |
| Glyceryl stearate (and) Laureth-23 | 2.0 | 2.0 |
| Isostearyl neopentanoate | 1.0 | 1.0 |
| Ethylhexyl palmitate | 2.0 | 2.0 |
| Glyceryl dilaurate | 0.5 | 0.5 |
| Octinoxate | 7.5 | 7.5 |
| Oxybenzone | 2.0 | 2.0 |
| Ethylhexyl salicylate | 3.0 | 3.0 |

SUNSCREEN FORMULAS

| RAW MATERIAL | Amount | |
|---|---|---|
| (INCI Designation) | SPF ~25 | SPF ~15 |
| Sodium hydroxide (10%) | 1.3 | 1.3 |
| Glyceryl polymethacrylate (and) Propylene glycol | 3.0 | 3.0 |
| Glyceryl polymethacrylate (and) Propylene glycol (and) PVM/MA copolymer | 0.5 | 0.5 |
| Styrene/Acrylates copolymer (27% solids) | 18.45 | — |
| Fragrance, preservative | QS | QS |
| Repeat sequence protein polymer | 0.5 | 0.5 |

VERY WATER-RESISTANT SUNSCREEN FORMULAS

| RAW MATERIAL | Amount | |
|---|---|---|
| (INCI Designation) | SPF ~12 | SPF ~22 |
| Water | 65.16 | 46.53 |
| Acrylates copolymer | 3.0 | 3.0 |
| Disodium EDTA | 0.1 | 0.1 |
| Butylene glycol | 2.0 | 2.0 |
| Gylceryl polymethacrylate (and) Propylene glycol (and) PVM/MA copolymer | 1.0 | 1.0 |
| Butylated PVP | 0.05 | 0.05 |
| Glyceryl stearate (and) Behenyl alcohol (and) Palmitic acid (and) Stearic acid (and) Lecithin (and) Lauryl alcohol | 4.5 | 4.5 |
| Tricontanyl PVP | 1.0 | 1.0 |
| Octyl palmitate | 2.0 | 2.0 |
| Octinoxate | 7.5 | 7.5 |
| Oxybenzone | 2.0 | 2.0 |
| Ethylhexyl salicylate | 3.0 | 3.0 |
| Tridecyl neopentanoate | 3.0 | 3.0 |
| Glyceryl dilaurate | 0.5 | 0.5 |
| Sodium hydroxide (10%) | 1.89 | 1.89 |
| Cyclopentasiloxane | 2.0 | 2.0 |
| Butylene glycol | 1.0 | 1.0 |
| Styrene/Acrylates copolymer (27% solids) | 18.45 | — |
| Fragrance, preservative | QS | QS |
| Repeat sequence protein polymer | 0.5 | 0.5 |

WATER-IN-SILICONE SUNSCREEN

| RAW MATERIAL (INCI Designation) | Amount |
|---|---|
| Cetyl PEG/PPG-15/15 butyl ether dimethicone | 2.0 |
| Mineral oil | 3.0 |
| Ethylhexyl palmitate | 1.0 |
| Ethylhexyl salicylate | 5.0 |
| Hydrogenated castor oil | 0.5 |
| Beeswax | 0.5 |
| Octinoxate | 7.5 |
| Polyethylene | 1.0 |
| PEG-30 dipolyhydroxystearate | 2.0 |
| Cyclopentasiloxane | 5.0 |
| Dimethicone | 5.0 |
| Sodium chloride | 0.6 |
| Acrylates/C12-22 alkylmethacrylate copolymer | 0.5 |
| Water | 66.4 |
| Fragrance, preservative | QS |
| Repeat sequence protein polymer | 0.5 |

Example 14

Foundation Formula

In this Example, a water in silicone foundation containing SELP47K is provided. This formulation contains the following ingredients:

| Ingredient | INCI Name | % |
|---|---|---|
| Water Phase | | |
| Dow Corning 9011 Elastomer Blend | Cyclopentasiloxane, PEG-12 Dimethicone Copolymer | 15.00 |
| Dow Corning 245 Fluid | Cyclopentasiloxane | 5.00 |
| Silcare 31 M50 SV | Caprylyl Trimethicone | 6.35 |
| Propylparaben | | 0.05 |
| AS 5811 | Titanium Dioxide, Triethoxycaprylylsilane | 7.50 |
| AS 5131 | Iron Oxides, Triethoxycaprylylsilane | 0.70 |
| AS 5146 | Iron Oxides, Triethoxycaprylylsilane | 0.05 |
| AS 5126 | Iron Oxides, Triethoxycaprylylsilane | 0.35 |
| AS 50230 | Talc, Triethoxycaprylylsilane | 3.50 |
| Oil Phase | | |
| Deionized Water | | 53.30 |
| SELP47K | | 1.80 |
| Butylene Glycol | | 6.00 |
| Methylparaben | | 0.20 |
| Benzoic Acid | | 0.20 |
| | | 100.00 |

The pigments (AS 5811, 5131, 5146, 5126, and 50230; Color Techniques) and propylparaben were dispersed in Silcare 31 M50 SV (Clariant), stirring until wet. The mixture was then passed over a three roll mill at tight setting until particle size is <10 μm. Then, DC 9011 Elastomer Blend (Dow Corning) and DC 245 Fluid were combined in finishing vessel, stirring until homogenous. The color grind was added with slow homogenizer agitation. The water was weighed into a separate vessel and SELP was gradually added with propeller agitation. stirring until dissolved. Methylparaben and benzoic acid were added to butylene glycol. The mixture was warmed slightly, and stirred until dissolved. The mixture was cooled to 30° C. and added to the SELP47K (GC2596-26-A) solution. The water phase was added slowly to the oil phase with rapid agitation. When addition was complete, the preparation was homogenized for five minutes. This preparation is useful as a makeup foundation for application to skin.

Example 15

Mascara Formulation

In this Example, a mascara formulation is provided. The ingredients of both a control preparation and a mascara containing 2% SELP47K (GC2596-26-A) are as follows:

| Trade Name | INCI Name | % Control 1 | 2% SELP 2 |
|---|---|---|---|
| Phase # Water Phase | | | |
| 1 Deionized Water | | 42.96 | 42.96 |
| 2 Butylene Glycol | | 5.00 | 5.00 |

-continued

| Trade Name | INCI Name | % Control 1 | 2% SELP 2 |
|---|---|---|---|
| 2 Methylparaben | | 0.30 | 0.30 |
| 3 33-5198 | (Black) Iron Oxides (Sun) | 10.00 | 10.00 |
| 4 Natrosol 250 MR | Hydroxyethylcellulose (Aqualon) | 0.20 | 0.20 |
| 5 10% KOH | Potassium Hydroxide | 0.01 | 0.01 |
| 6 Arlacel 165 | Glyceryl Stearate, PEG-100 Stearate (Uniqema) | 3.00 | 3.00 |
| 7 10% Citric Acid | | 0.27 | 0.27 |
| Phase # Wax Phase | | | |
| 8 Arlacel 165 | | 1.00 | 1.00 |
| 8 Cerasynt SD | Glyceryl Stearate (ISP) | 3.50 | 3.50 |
| 8 Beeswax, White SP 424 | Beeswax (S&P) | 7.50 | 7.50 |
| 8 Carnauba #1 | Copernica Cerifera (Carnauba) Wax (S&P) | 4.80 | 4.80 |
| 8 Propylparaben | | 0.10 | 0.10 |
| 9 Deionized Water | | 20.00 | — |
| 9 10% SELP/Water | | — | 20.00 |
| 10 Deionized Water | | 1.00 | 1.00 |
| 10 Glydant | DMDM Hydantoin (Lonza) | 0.36 | 0.36 |
| | | 100.00 | 100.00 |

To produce the mascara formulation, the wax phase 8 was combined and heated to 85-90° C. with propeller mixing. The 10% SELP47K solution was prepared by adding SELP47K powder to water while propeller mixing. Phase 1 water was added to a tared stainless steel beaker (approximately 50 g excess was added to compensate for loss). Phase 2 methylparaben was added to butylene glycol and stirred while warming on top of a steam bath until dissolved, then added to the water with slow homomixer agitation. Then, the phase 4 black iron oxide was added, while maintaining agitation. Then, Natrosol was sprinkled in, while maintaining agitation. The 10% KOH was added, and heating was begun to 85° C., with the beaker covered as tightly as possible. When the Natrosol was dissolved, the 10% citric acid was added dropwise, maintaining temperature and agitation. Then, the Arlacel 165 was added slowly and mixed for at least 5 minutes to insure dissolution. At 85-90° C., the wax phase was slowly added to the water phase while homomixing. The temperature and agitation are maintained for 10 minutes. The batch was removed from the steam bath and allowed to cool while homomixing with occasional hand scraping of the beaker walls. At 55° C., the batch was weighed to check for water loss. Mixing was resumed and water was added back, if necessary. At 45° C., phases 9 and 10 were added. Cooling was continued using cold water to 30° C. At this point, continuous hand scraping of beaker walls was necessary.

In this preparation, the small amount of KOH (in Phase 5) is used to raise the pH to disperse the Natrosol which is coated with glyoxal to retard wetting, and prevent agglomeration. In phase 7, the citric acid is added slowly to adjust pH to ~5.5, below the isoelectric point of the iron oxides. In phases 7 and 8, the Arlacel 165 is split between the oil and water phases, as the emulsification is easier to accomplish with surfactant in both phases. In phase 9, the deionized water was added in the control batch instead of SELP47K. The SELP47K solution was prepared while the emulsion was being processed, so it was absolutely fresh. This preparation provides a formulation suitable for use as a mascara.

Example 16

Bioactivity Determination of RSPPs Using Human Skin Fibroblast Cells In-Vitro

In this Example, experiments conducted to determine bioactivity of repeat sequence protein polymers (RSPP) such as SELP47K and others (i.e., GC2596-26-A-E) in procollagen synthesis, matrix metaloprotease-1 (MMP-1) activity, and elastin production as well as elastase activity are described. The RSPP test materials used in these experiments are those shown in Table 1.

As dermal fibroblasts are the main source of extracellular matrix proteins, including large structural proteins such as collagen and elastin, as well as the enzymes that metabolize these proteins (e.g. Matrix Metalloprotease-1 [MMP-1] and elastase) within the skin, these experiments were conducted to determine bioactivity of RSPP in influencing collagen synthesis, elastin production, and MMP-1 activity. An accepted cultured human fibroblast model was used in these experiments.

Initial screening was conducted to identify a test range suitable to determine the effect of a broad range of test material concentrations on cell viability. In particular, these initial screening experiments were conducted in order to ensure that the concentrations of test RSPPs used within the study had a no cytotoxic effect. Cultured fibroblasts were exposed to the test materials for 48 hours and then changes in cell viability were determined using an MTT assay (i.e., a calorimetric analysis of the metabolic activity of the cultured cells, described in greater detail below).

When cells are treated with MTT, it is reduced by the mitochondria, which results in the formation of insoluble purple formazin crystals that are trapped within the cell. The purple crystals are extracted from the cells with isopropanol and the amount of crystal formation quantified spectrophotometrically. The intensity of the purple color is directly proportional to the metabolic activity of the cultured cells, which normally is used as an indication of an increase in the number of viable cells, although it can also indicate an increase in the mitochondrial content of the existing cells (Alley et al., Cancer Res., 48:589-601 1988). A decrease in color intensity can be a sign of toxicity.

Once an experimentally useful range of RSPP test material concentrations was determined, their effect on procollagen synthesis, elastin production and MMP-1 activity were then determined. All three of these markers are released into the cell culture media by the fibroblasts. Thus, after 48 hours of exposure to the test RSPP materials the media were collected and assayed.

Collagen is synthesized as part of a much larger procollagen peptide. As the peptide is processed to form a mature collagen protein, the propeptide portion is cleaved off (type I C-peptide). Both the mature collagen protein and the type I C-peptide fragment are then released into the extracellular environment and accumulate in the culture media. Since there is a 1:1 stoichiometric ratio between the two parts of the procollagen peptide, assaying for type I C-peptide will reflect the amount of collagen synthesized. Type 1 C-peptide can be assayed via an ELISA based method.

Elastin is released by fibroblasts (soluble elastin) into the extracellular space where it is then cross-linked to other elastin proteins to form an extensive network of fibers and sheets (insoluble elastin). Soluble elastin can be readily measured from cell culture medium via a colorimetric assay.

MMP-1 is a zinc and calcium dependent endopeptidase that is produced and released from both dermal fibroblasts and keratinocytes, and functions to break down collagens located in the extracellular matrix. Active MMP-1 released into the culture media can be assayed using a fluorescence-based ELISA. Briefly, antibodies covalently linked to a solid support will bind any MMP-1 (both active and inactive MMP-1) present in spent culture media samples. To quantify the active MMP-1 a fluorogenic substrate linked to a quencher molecule is added and any active MMP-1 present will cleave the peptide linkage between the fluorophore and the quencher molecule. This cleavage will eliminate the quencher molecules ability to inhibit the fluorescent signal of the fluorophore allowing a fluorescent signal that will be proportional to the amount of active MMP-1 present. The MMP-1 standards used with the ELISA kit (R&D Systems) used in the experiments described herein are provided in an inactive form and need to be activated by exposing them to p-aminophenylmercuric before adding the fluorogenic substrate.

The RSPP test materials were also tested to determine their effect(s) on elastase activity. In these experiments, human dermal fibroblasts were used as a source of the elastase enzyme. This enzyme was partially purified from the fibroblasts by lysing the cells in an elastase buffer and retaining the soluble portion of the lysate. Portions of this fibroblast lysate were then incubated with test materials and a synthetic elastase substrate, Suc-$(Ala_3)$-p-Nitroaniline (STANA). Elastase acts upon this substrate to release p-nitroaniline, which can be detected spectrophotometrically by measuring the absorbance at a wavelength of 405 nm. An inhibition of the elastase enzyme is noted by a decrease in the amount of released p-nitroaniline when compared to uninhibited enzyme.

A. Procollagen Synthesis, MMP-1 Activity and Elastin Production By RSPP Test Materials
Preparation of Fibroblasts Fibroblasts (Cascade Biologics, HDFn Cell Line, lot#1C0914) were seeded into the individual wells of either a 96-well plate (for the initial pilot work to determine concentration effects on cell viability) in 100 μl of Fibroblast Growth Media (FGM) or in 12-well plates (for the measurement of collagen, elastin and MMP-1) in 1.0 ml of FGM and incubated overnight at $37\pm2°$ C. and $5\pm1\%$ $CO_2$. On the following day, the medium was removed via aspiration to eliminate any non-adherent cells and replaced with fresh FGM. The cells were grown until confluent, with a media change every 48 to 72 hours. Upon reaching confluency, the cells were treated for 24 hours with Dulbecco's Modified Essential Media (DMEM) supplemented with 1.5% FBS to wash out any effects from the growth factors included in the normal FGM. After this 24-hour wash out period, the cells were treated with the test materials at the specified concentrations dissolved in DMEM with 1.5% FBS. Untreated cells (negative controls) received DMEM with 1.5% FBS. The cells were incubated for 48 hours and at the end of the incubation period cell culture medium was either discarded (pilot work) or collected and stored frozen at $-75°$ C. The test materials were tested in triplicate.

MTT Assay

After the 2-day incubation, the cell culture medium was removed and the fibroblasts were washed twice with PBS to remove any remaining test material. After the final wash, either 100 μl (96-well plates) or 300 μl (12-well plates) of DMEM supplemented with 0.5 mg/ml MTT were added to each well and the cells were incubated for 1 hour at $37\pm2°$ C. and $5\pm1\%$ $CO_2$. After the incubation, the DMEM/MTT solution was removed and the cells were washed again once with PBS and then either 100 μl (96-well plates) or 1 ml (12-well plates) of isopropyl alcohol were added to each well to extract the purple formazin crystals. For the 12-well plates, two hundred microliters of the isopropyl extracts was transferred to a 96-well plate. The 96-well plates were read at 540 nm using isopropyl alcohol as a blank. The mean MTT absorbance value for the negative control cells was calculated and used to represent 100% value for cell viability. The individual MTT values from the cells undergoing the various treatments were then divided by the mean value for the negative control cells and expressed as a percent, to determine the change in cell viability caused by each treatment.

Procollagen Assay

Takara procollagen type IC-peptide ELISA kits were used in these experiments. A series of type I C-peptide standards was prepared ranging from 40 ng/ml to 640 ng/ml. An ELISA microplate was then prepared by removing any unneeded strips from the plate frame. To each well in the plate 100 μl of peroxidase-labeled anti procollagen type I-C peptide was added, followed by 20 μl of either sample (tissue culture media) or standard. The microplate was covered and allowed to incubate for $3\pm0.25$ hours at $37°$ C. After the incubation period, each well was aspirated and washed three times with 400 μl of wash buffer. After the last wash was removed, 100 ρl of peroxidase substrate solution (hydrogen peroxide containing tetramethylbenzidine as a chromagen) were added to each well and the plate was incubated for $15\pm5$ minutes at room temperature. After the incubation period, 100 μl of stop solution (1 N sulfuric acid) was added to each well and the plate was read using a microplate reader at 450 nm. To quantify the amount of procollagen present, a standard curve was generated using known concentrations of procollagen type 1-C peptide. A linear regression was then performed to establish the line that best fit these data points. Mean absorbance values for the test materials and untreated samples was then used to estimate the amount of procollagen type 1-C peptide present in each sample.

MMP-1 Assay

R&D Products MMP-1 Flurokine E fluorometric ELISA kits were used in these experiments. A series of MMP-1 standards was prepared ranging from 0.39 ng/ml to 25 ng/ml and an ELISA microplate was prepared by removing any unneeded strips from the plate frame. In each well, 200 μl of Assay Diluent RD1-64 and 50 μl of each sample were added. For the standards, 100 μl of Assay Diluent RD1-64 and 150 μl of each respective standard were added. The plate was incubated for $3\pm0.25$ hours at room temperature on a rocking platform. At the end of the incubation period, each well was aspirated and then washed four times with 400 μl of wash buffer. Since the MMP-1 enzyme standards included with the assay kit are provided in an inactive form, after the last wash was removed, 200 μl of p-aminophenylmercuric acetate in Reagent Dilution solution was added to the standards to activate MMP-1, while Reagent Dilution solution only was added to the samples and the plate was incubated for $2\pm0.25$ hours at $37\pm2°$ C. After the incubation period, the plate was washed four times as described above. After the last wash, 200 μl of substrate solution were added to each well and the plate was incubated for 17-20 hours at $37\pm2°$ C. (protected from light). At the end of the incubation period, the fluorescence intensity was measured (excitation 320 nm, emission 405 nm) using a fluorometer using a 20 mS integration time. To quantify the amount of MMP-1 activity, a standard curve was generated using known activity levels of MMP-1. A linear regression was performed to establish the line that best fit these data points. Mean absorbance values for the test materials and untreated samples were then used to estimate the amount of MMP-1 activity present in each sample.

Elastin Assay

In these experiments, the Biocolor Fastin Elastin Assay kits were used. A 50 µl aliquot of sample material (cell culture medium for soluble elastin) was mixed with 1.0 ml of cold Fastin Precipitating Reagent in a 1.5-ml microcentrifuge tube. In addition to the spent media samples from the fibroblasts, 50 µl aliquots of the test materials diluted into fresh culture media at the concentrations used in the study were also assayed for elastin content. The sample/Fastin Precipitating Reagent mixture was then incubated overnight in an ice water bath to precipitate the elastin. On the following day, the cold microcentrifuge tubes were spun at 10,000×g for 10 minutes to pack the precipitated elastin and the supernatant was removed via careful aspiration.

One (1) ml of Fastin Dye Reagent, along with 100 µl of 90% saturated ammonium sulphate was added to each tube. The microcentrifuge tubes were mixed with a vortex mixer and then allowed to incubate for at least 60 minutes at room temperature, with gentle mechanical agitation. The Fastin Dye Reagent interacts with unique amino acid sequences in the elastin protein. This elastin-dye complex precipitates in the presence of ammonium sulphate. After the incubation was over, the microcentrifuge tubes were spun at 10,000×g for 10 minutes to separate the precipitated elastin-dye complex from the unbound dye. The supernatant was carefully removed and the tubes were inverted to allow any residual supernatant to drain out.

To release the elastin-bound dye, 1.0 ml of Fastin Destain reagent was added to each microcentrifuge tube. The tubes were capped as quickly as possible, as this reagent contains ammonia and methanol. The tubes were then vortexed. The absorbance of this solution was measured by a plate reader at 490 nm (200 µl volume read).

An elastin standard curve was generated using 12.5, 25, and 50 µg aliquots of an Elastin Standard into microcentrifuge tubes (in duplicate). These samples were treated as described above (Elastin Assay) and the absorbance values were used to generate a standard curve of known concentrations. To derive the standard curve for the elastin assay, the absorbance was plotted against the elastin concentration in µg/ml for the standards. A linear regression was performed to establish the line that best fit these data points. Mean absorbance values for the test materials and untreated samples were then used to estimate the amount of elastin present in each sample.

B. Elastase Activity Experiments

Fibroblast Cell Culture Procedure

Fibroblasts (Cascade Biologics, HDFn Cell Line, lot#1C0914) were seeded in a 75-cm$^2$ flask and grown in FGM and cultured at 37±2° C. and 5±1% $CO_2$. Cells were expanded and passed until a sufficient number of cells had been grown (not exceeding 10 passages). When a sufficient number of cells had been grown, the fibroblast lysate containing the elastase enzyme was prepared as follows:

Fibroblast Lysate Procedure

The fibroblasts were washed twice with 15 ml of phosphate buffered saline with each wash removed via aspiration. Ice cold PBS (7.5 ml) was then added to the flask and the cells were detached with a cell scraper. The detached cells/PBS was transferred to a 15 ml centrifuge tube on ice. The flask was rinsed again with 7.5 ml of PBS, which was also transferred to the 15 ml tube. The tube was then centrifuged at 1,200 RPM for 5 minutes and the supernatant was removed via aspiration. The pellet of cells was resuspended in 2 ml of ice-cold 2× elastase buffer and sonicated for 10 seconds (maximum setting) to lyse the cells. The sonication was repeated until the contents of the tube were clear while the tube was maintained on ice. The tube was then centrifuged at 2,200 RPM for 10 minutes at 4° C. and the supernatant was transferred to a new centrifuge tube (this portion of the fibroblast lysate contained the elastase enzyme) and kept on ice. The protein concentration of the fibroblast lysate was determined using the Pierce BCA Protein Assay kit (see below for details) and the fibroblast lysate was stored at −75° C. until used (for up to 1 year). Bicinchoninic Acid (BCA) Protein Assay Fifty volumes of Reagent A (BCA) were combined with 1 volume of Reagent B (4% (w/v) $CuSO_4$–$5H_2O$) in a 15-ml centrifuge tube. For the assay, proteins reduce Cu(II) to Cu(I) in a concentration dependent manner. BCA then reacts with the Cu(I) to form a purple colored complex with a maximum absorbance at 562 nm. Two hundred microliters of this combined reagent were dispensed into each well of a 96-well plate. Next, 10 µl of each of the standards were added into their respective wells (standards were made using 2 mg/ml bovine serum albumin dissolved in elastase buffer, and then a series of 50% dilutions was made down to 0.0078 mg/ml). Ten µl of elastase buffer was added to two wells to serve as blanks. The standards and blank were prepared in duplicate, while lysate samples were prepared in triplicate. The plate was covered, incubated it at 37±2° C. for 30±5 minutes and then read using a microplate reader at 540 nm.

Determination of Elastase Activity in Lysate-Range Finding

Upon determining the protein concentration of the lysate, a small sample was obtained and the elastase activity of the lysate was determined at 1×, 0.5× and 0.25× concentrations. The activity was determined for each of the different concentrations in exactly the same way that the uninhibited sample was treated in the elastase assay (see below). First, 100 µl of lysate was loaded into three wells, while 100 µl of 2× Elastase buffer was added to three additional wells to serve as blanks. Then, 100 µl of diluted DMSO (1 part DMSO, 49 parts deionized water) was added to all six wells used and the 96-well plate was incubated for 15 minutes at 37±2° C. Then, 4 µl of STANA was added to each well used, and the 96-well plate was returned to the incubator for 1.25 hours. After 1.25 hours, the well plate was removed and read in a 96-well plate reader at 405 nm. The mean absorbances were plotted versus concentration. These values were used to estimate a concentration that will produce a spectrophotometric measurement of 0.4 to 0.5 using a linear regression analysis of the best-fit line through all three (1×, 0.5× and 0.25×) data points. The remaining fibroblast lysate was diluted to the appropriate concentration to elicit the desired level of activity.

Test Material Preparation

For this assay, test materials were prepared in deionized water at 2× their final desired concentration. Since each material was tested at final concentrations of 1%, 0.5% and 0.1%, they were prepared at stock concentrations of 2%, 1% and 0.2%. 10 mM and 3 µM phosphoramidon served as the positive control, while a 50 fold dilution of DMSO in deionized water served as a negative (uninhibited) control.

As these testing materials were hypothesized to potential inhibit the breakdown of STANA by the elastase enzyme via a competitive mechanism, the STANA substrate was mixed with the test materials so that they were added to the assay simultaneously. The STANA substrate was mixed with the stock test material solutions at a ratio of 4 µl of STANA for every 100 µl of stock test material solution.

Elastase Enzyme Assay, Modified Procedure

Six wells in a 96-well plate were reserved for each concentration of test material. In three of the wells 100 µl of fibroblast lysate (lysate lot 082103) in 2× elastase buffer were added, while in the three remaining wells, 100 µl of 2× elastase buffer alone were added. After the wells were prepared with lysate or buffer, 100 µl of test material solution, phosphoramidon control, or diluted DMSO was added to the 6 wells reserved for each respective test. The plate was then covered and incubated at 37±2° C. The change in absorbance at 405 nm was measured at 0 minutes, 30 minutes, 60 minutes, 90 minutes and 120 minutes using a microplate reader.

For the elastase assay, the mean absorbance values for the three wells containing the various test materials and the fibroblast lysate were used as an index of elastase activity. The remaining three wells, containing the test materials and the elastase buffer were used to determine the amount of background absorbance due to either the test material itself or the non-specific breakdown of STANA. To correct the absorbance value associated with elastase activity, the background absorbance value was subtracted. To determine the percent of elastase inhibition induced by the test material, the following equation was used:

(1−(elastase activity with test material/elastase activity in untreated controls))×100

C. Results

The results from the initial pilot cell viability dose response experiment are presented in Table 17.

TABLE 17

Initial Pilot Cell Viability Dose Response Results

| Concentration | Test Material | | | | |
|---|---|---|---|---|---|
| | GC 2596-26-A | GC 2596-26-B | GC 2596-26-C | GC 2596-26-D | GC 2596-26-E |
| 1% | 138 ± 7 | 79 ± 17 | 180 ± 6 | n/a | 6 ± 1 |
| 0.5% | 171 ± 4 | 120 ± 5 | 180 ± 12 | n/a | 17 ± 4 |
| 0.14% | 101 ± 4 | 92 ± 4 | 113 ± 8 | 154 ± 24 | 61 ± 7 |
| 0.07% | 96 ± 6 | 101 ± 3 | 107 ± 10 | 145 ± 11 | 75 ± 9 |
| 0.014% | 99 ± 10 | 98 ± 5 | 106 ± 9 | 145 ± 12 | 124 ± 7 |
| 0.007% | 101 ± 5 | 92 ± 10 | 97 ± 8 | 138 ± 9 | 113 ± 6 |
| 0.0014% | 99 ± 1 | 99 ± 11 | 107 ± 10 | 130 ± 15 | 117 ± 10 |

The values are presented as a percent of untreated cells, which are used to represent 100% cell viability. A value above 100% indicates that the material either stimulated cell proliferation or an increase in mitochondrial activity. Based upon the results from this initial pilot work, suitable concentrations of the test materials were chosen for the remaining experiments.

The results from the MTT Assay are presented in Table 18. As in Table 17, the values are again presented as a percent of untreated cells, which are used to represent 100% cell viability. The results for the collagen synthesis assay are presented in Table 19, while the results for the MMP-1 activity assay are presented in Table 20. Finally, the results for elastin metabolism are presented in Table 21 (elastin production assay) and Table 22 (elastase inhibition assay). In these Tables, "A" represents GC2596-26-A, while "B" represents GC2596-26-B, "C" represents GC2596-26-C, "D" represents GC2596-26-D, and "E" represents GC2596-26-E.

TABLE 18

MTT Assay Results

| Treatment | Percent Viability |
|---|---|
| 1% A | 120 ± 4 |
| 0.5% A | 122 ± 3 |
| 0.1% A | 98 ± 3 |

TABLE 18-continued

MTT Assay Results

| Treatment | Percent Viability |
|---|---|
| 1% B | 77 ± 4 |
| 0.5% B | 95 ± 2 |
| 0.1% B | 102 ± 4 |
| 1% C | 127 ± 3 |
| 0.5% C | 123 ± 4 |
| 0.1% C | 102 ± 4 |
| 0.014% D | 106 ± 5 |
| 0.007% D | 103 ± 2 |
| 0.0014% D | 100 ± 3 |
| 0.01% E | 93 ± 2 |
| 0.005% E | 100 ± 2 |
| 0.001% E | 101 ± 3 |

TABLE 19

Procollagen Assay Results

| Treatment | Type-1 C Peptide (ng/ml) |
|---|---|
| Untreated | 873 ± 111 |
| 1% A | 687 ± 49 |
| 0.5% A | 715 ± 72 |
| 0.1% A | 932 ± 116 |
| 1% B | 990 ± 40 |
| 0.5% B | 1366 ± 127 |
| 0.1% B | 1370 ± 169 |
| 1% C | 714 ± 120 |
| 0.5% C | 900 ± 143 |
| 0.1% C | 817 ± 55 |
| 0.014% D | 829 ± 171 |
| 0.007% D | 908 ± 94 |
| 0.0014% D | 894 ± 156 |
| 0.01% E | 956 ± 110 |
| 0.005% E | 1162 ± 194 |
| 0.001% E | 838 ± 75 |

TABLE 20

MMP-1 Assay Results

| Treatment | MMP-1 Activity (ng/ml) |
|---|---|
| Untreated | 0.11 ± 0.05 |
| 1% A | 0.12 ± 0.05 |
| 0.5% A | 0.09 ± 0.04 |
| 0.1% A | 0.10 ± 0.02 |
| 1% B | 0.12 ± 0.04 |
| 0.5% B | 0.10 ± 0.02 |
| 0.1% B | 0.09 ± 0.03 |
| 1% C | 0.12 ± 0.02 |
| 0.5% C | 0.11 ± 0.02 |
| 0.1% C | 0.10 ± 0.03 |
| 0.014% D | −0.03 ± 0.01 |
| 0.007% D | −0.02 ± 0.02 |
| 0.0014% D | −0.01 ± 0.01 |
| 0.01% E | 0.00 ± 0.02 |
| 0.005% E | −0.01 ± 0.02 |
| 0.001% E | 0.04 ± 0.05 |

TABLE 21

Elastin Assay Results

| Treatment | Elastin (µg/ml media) |
|---|---|
| Untreated | 69 ± 2 |
| 1% A | 360 ± 67 |
| 0.5% A | 102 ± 10 |
| 0.1% A | 61 ± 16 |

TABLE 21-continued

Elastin Assay Results

| Treatment | Elastin (µg/ml media) |
|---|---|
| 1% B | 43 ± 12 |
| 0.5% B | 47 ± 9 |
| 0.1% B | 67 ± 7 |
| 1% C | 63 ± 15 |
| 0.5% C | 70 ± 10 |
| 0.1% C | 68 ± 7 |
| 0.014% D | 68 ± 10 |
| 0.007% D | 69 ± 4 |
| 0.0014% D | 72 ± 12 |
| 0.01% E | 50 ± 18 |
| 0.005% E | 59 ± 5 |
| 0.001% E | 63 ± 10 |
| 1% A media only | −1 |
| 1% B media only | −1 |
| 1% C media only | −1 |
| 0.014% D media only | −1 |
| 0.01% E media only | −1 |

TABLE 22

Elastase Inhibition Assay Results

| Treatment | Percent Inhibition |
|---|---|
| 1% A | −16 |
| 0.5% A | −11 |
| 0.1% A | −19 |
| 1% B | −22 |
| 0.5% B | −20 |
| 0.1% B | −16 |
| 1% C | 26 |
| 0.5% C | 20 |
| 0.1% C | 19 |
| 1% E | −5 |
| 0.5% E | −20 |
| 0.1% E | −13 |
| 100 uM Phosphoramidon | 96 |
| 30 nM Phosphoramidon | 43 |

D. Summary of Data and Results

The initial dose response work (See, Table 17) with this set of peptides revealed a broad range of effects. Peptides GC2596-26-A, GC2596-26-C and GC2596-26-D were observed to strongly stimulate increases in the number of viable cells in a dose dependent manner. In contrast, peptides GC2596-26-B and GC2596-26-E) were observed to reduce the number of viable cells, with peptide B only having this effect at the highest concentration tested. GC2596-26-E had adverse effects at concentrations equal to or greater than 0.07%.

In view of these initial results, peptides GC2596-26-A, GC2596-26-B and GC2596-26-C were tested at 1%, 0.5% and 0.1% concentrations, while peptide GC2596-26-D was tested at 0.014%, 0.007% and 0.0014%, and GC2596-26-E was tested at 0.01%, 0.005% and 0.001% for the cell culture based assays. After 48 hours of incubation with the materials, the culture media were collected for analysis and the cells were again subjected to an MTT assay. The results for the second cell viability assay (See, Table 18) were confirmed the earlier results shown in Table 17, at the concentrations tested.

In the next set of experiments, the effect of the RSPP test materials on collagen synthesis was assessed (See, Table 19). Of these, RSPP test material GC2596-26-B showed improvement in collagen synthesis. Collagen synthesis was observed to be elevated at the 0.5% and 0.1% concentrations. However, at the 1% concentration, the amount of collagen synthesis declined back down to a level similar to the untreated group. The reason for this decline in collagen synthesis at the 1% concentration may possibly be related to the negative effect on cell viability that this material is also observed to have at this concentration, as shown in Table 23, below. Thus, when a ratio of collagen synthesis to viability is taken into account, RSPP test material GC2596-26-B improves collagen synthesis at all of the concentrations tested (i.e., as compared to the control).

TABLE 23

Test Results for Test Material GC2596-26-B

| Treatment | Viability Score | Collagen Score |
|---|---|---|
| 1% B | 77 | 990 |
| 0.5% B | 95 | 1366 |
| 0.1% B | 102 | 1370 |

Since the collagen content of the skin is regulated not only by the rate of collagen synthesis, but also on the rate of collagen breakdown, the effect of the materials on MMP-1 (collagenase) activity was also determined (See, Table 20). RSPP test materials GC2596-26-D and GC2596-26-E resulted in an almost complete loss of detectable MMP-1 activity in the samples. Although it is not intended that the present invention be limited to any particular mechanism, possible explanations include down-regulation of the gene expression of MMP-1, thereby shutting off the production of this enzyme. Another hypothesis is that the peptide prevented activation of any MMP-1 produced. Normally, MMP-1 is synthesized and released in an inactive form that must be activated extracellularly by MMP-3. If these two RSPP test materials were inhibiting MMP-3, then this would also have the effect of preventing MMP-1 activation.

Aside from collagen, another major component of the skins extracellular matrix is elastin. Like collagen, the elastin content of the skin is determined both by its rate of synthesis and its rate of degradation by elastase. With respect to elastin synthesis (See, Table 21), RSPP test material GC2596-26-A was observed to stimulate an excellent increase. On the degradation side (See, Table 22), RSPP test material GC2596-26-C was observed to inhibit the elastase enzyme, with an inhibition level of about 20%.

With respect to the elastin production assay, it should be noted that there was some concern that the RSPP test materials themselves might interfere with the assay since they contain sequences similar to elastin. Table 21 shows the results of assaying culture media supplemented with the highest concentrations of each of the test materials and for all 5 RSPP test materials there was no elastin detected. Thus, there appeared to be no interference with the assay methods due to the RSPP tested materials.

Example 17

UVB Protective Effect of SELP47K-P4 RSPP

This Example describes experiments conducted to assess the ability of SELP47K-P4 RSPP (GC 2596-26-D) to exert a protective effect by promoting cell survival after UVB exposure.

In these experiments, the test material was tested at six concentrations with two duplicate sets of cells prepared. The first set of cells was exposed to approximately 50 mj/cm$^2$ of UVB, which has been shown to reduce the number of viable cells by up to 50%, followed immediately by the application of either the test material, 20 µM Trolox (an anti-oxidant, used as a positive control), or left untreated (untreated controls). The second set of cells did not receive a dose of UVB and was just exposed to either the test material, Trolox, or left untreated. Changes in cell viability were then determined 48 hours post material application via an MTT assay, as described above.

As discussed in greater detail herein, the results suggested that the RSPP test material GC2596-26-D was capable of both improving cell survival when it was applied after UVB exposure, and also able to induce cell proliferation in a dose dependent manner. Therefore, the aim of the follow-up study, was to determine if treatment with the test material before or during UVB exposure provided any additional survival benefit(s). Four different treatment regiments were employed using different combinations of pretreatment with the test material prior to UVB exposure and treatment with the material during UVB exposure. Cell survival was again assessed via an MTT assay 48 hours after the UVB insult. In addition, this second study also incorporated the use of 2',7'-dichloro-dihydrofluorescein diacetate (DCF), which is a relatively non-fluorescent dye that can be loaded into cells and becomes fluorescent upon exposure to the reactive oxygen species (ROS) generated during UVB exposure (Carini et al., Il Farmaco 55:526-534 [2000]; and Chan et al., J. Cell. Biochem., 90:327-338 [2003]). The diacetate form of the dye can freely traverse cell membranes, however once inside of the cell intracellular esterases will cleave off the acetate side groups trapping the DCF dye within the cell. The results confirmed the UVB protective effect of the RSPP test material 2596-26-D when applied post UVB exposure, and also indicated that its protective effect was improved when the material was also present both before and/or during UVB exposure.

Preparation of Fibroblasts

Fibroblasts were seeded into the individual wells of a 96 well plate in 100 µl FGM, and incubated overnight at 37±2° C. and 5±1% $CO_2$. On the following day, the media were removed via aspiration to eliminate any non-adherent cells and replaced with 100 µl of fresh FGM. The cells were grown until confluent, with a media change every 48 to 72 hours.

UVB Exposure and Treatment Protocol

An UVLM-26 lamp was used as the source of UVB light. UV light intensity was measured using a UVX radiometer coupled to a UVB sensor probe (UV Products) to determine the time required to deliver an approximate dose of 50 mj/$cm^2$. Prior to UVB exposure, the FGM was replaced with 100 µl PBS. After exposure, the PBS was removed and replaced with FGM supplemented with either the test materials, 20 µM Trolox, or left unsupplemented. A duplicate set of cells was also prepared and treated as described above, with the exception that they were not exposed to UVB light. This second set was used to assess any changes in cell viability induced by the test materials alone. The cells were allowed to incubate with the test materials for 48 hours, and then changes in cell viability were determined via an MTT assay. The non-UVB exposed cells treated with unsupplemented FGM were used to represent 100% cell viability.

For this initial study the RSPP test material GC2596-26-D was tested at the following six combinations: 0.14%, 0.07%, 0.014%, 0.007%, 0.0014% and 0.0007%.

UVB Exposure and Pretreatment Protocol

Two sets of duplicate cells were prepared using the four treatment protocols outlined in Table 24. One set of cells was used for an MTT assay while the other set of cells was used to measure the formation of ROS using the fluorescent DCF dye indicator.

TABLE 24

| | Treatment Protocols | | |
|---|---|---|---|
| Treatment | 24 hour pretreatment with test material | Material present during UVB exposure | Material present for 48 hours after UVB exposure |
| 1 | + | − | + |
| 2 | + | + | + |
| 3 | − | − | + |
| 4 | − | + | + |

In Table 24, "+" indicates that the material was present, while "−" indicates that the material was absent.

For this follow up study, the material was tested at concentrations of 0.14% and 0.014%. During the pretreatment phase, the test material was diluted in FGM (for treatments 1 and 2). Prior to UVB exposure the FGM was replaced with 100 µl PBS (supplemented with the test material for treatments 2 and 4) using the same UVB exposure protocol as described above. After exposure, the PBS was removed and replaced with FGM supplemented with either the test materials or left unsupplemented. The cells were allowed to incubate with the test materials for 48 hours to assess changes in cell viability via an MTT assay and to determine changes in ROS formation via the fluorescent DCF dye indicator. For the MTT assay, cells that were not exposed to UVB or treated with test materials were used to represent 100% cell viability.

At the end of the 48 hour incubation period, the cells were photographed to record any changes in cell morphology.

MTT Assay

After the 48-hour incubation, the cell culture medium was removed and the fibroblasts were washed with PBS to remove any remaining test material. After the final wash, 100 µl of DMEM supplemented with 0.5 mg/ml MTT was added to each well, and the cells were incubated for 1 to 2 hours at approx. 37±2° C. and 5±1% $CO_2$. After the incubation period, the DMEM/MTT solution was removed and the cells were washed again, once with PBS and then 50 µl of isopropyl alcohol was added to the well to extract the purple formazin crystals. The 96-well plate was then read at 540 nm using isopropyl alcohol as a blank.

The mean MTT absorbance value for the negative control cells (non-UVB exposed and non test material treated cells) was calculated and used to represent 100% value for cell number. The individual MTT values from the cells undergoing the various treatments was then divided by the mean value for the negative control cells and expressed as a percent, to determine the change in cell viability caused by each treatment. MTT scores for each treatment are expressed as means±the standard deviation of the mean.

The results of the initial MTT Assay for are presented in Table 25, below. The values are expressed as mean viability±standard deviation with an n=4 for each treatment.

TABLE 25

| | Initial MTT Assay Results | |
|---|---|---|
| Treatment | −UVB Percent Viability | +UVB Percent Viability |
| Untreated | 100 ± 6 | 55 ± 9 |
| 0.14% | 154 ± 24 | 104 ± 11 |
| 0.07% | 145 ± 11 | 90 ± 20 |
| 0.014% | 145 ± 12 | 83 ± 8 |
| 0.007% | 138 ± 9 | 81 ± 12 |
| 0.0014% | 130 ± 15 | 76 ± 13 |
| 0.0007% | 131 ± 7 | 69 ± 9 |
| 20 µM Trolox | 120 ± 11 | 77 ± 9 |

The results for the follow-up MTT Assay are presented in Table 26. The values are expressed as mean viability±standard deviation with an n=4 for each treatment. The T followed by a number indicates which treatment group the data belong to (See, Table 24).

TABLE 26

Follow-Up MTT Assay Results

| Treatment | Percent Viability |
|---|---|
| No UVB | 100 ± 27 |
| UVB | 79 ± 19 |
| T1 0.14% | 122 ± 20 |
| T1 0.014% | 85 ± 7 |
| T2 0.14% | 126 ± 25 |
| T2 0.014% | 78 ± 4 |
| T3 0.14% | 97 ± 14 |
| T3 0.014% | 88 ± 17 |
| T4 0.14% | 121 ± 19 |
| T4 0.014% | 86 ± 6 |

Fluorescent DCF Dye Assay

One hour prior to UVB exposure, the cell culture media were removed and the wells were washed with PBS to remove any residual RSPP test material in the set of cells used for the DCF assay. A 20 mM stock of DCF prepared in DMSO was diluted to 10 µM using PBS and 100 µl of this solution were added to each well. The plate was then returned to the incubator for 1 hour, to allow sufficient time for the cells to take up and trap the dye. After the 1-hour incubation, the cells were washed with PBS to remove any unincorporated dye and then exposed to UVB using the protocol described above. Forty-eight hours later, the 96-well plate was read using a fluorometer set for an excitation wavelength of 485 nm and an emission wavelength of 518 nm. The duplicate set of wells run for the MTT assay served as non-dye loaded blanks to account for any background fluorescence due to the cells or the test material.

The mean fluorescence intensity was determined for each of the treatment groups (measured in relative fluorescence units or "RFU"). Since the test material was shown to induce cell proliferation, the RFU values were expressed as a ratio to the 48-hour MTT values, to normalize as best as possible for any changes in cell number that occurred.

The results for the DCF Assay are presented in Table 27. Values are expressed as the ratio of mean RFU to mean percent viability for each individual treatment.

TABLE 27

DCF Assay Results

| Treatment | RFU/Viability |
|---|---|
| No UVB | 0.031 |
| UVB | 0.057 |
| T1 0.14% | 0.038 |
| T1 0.014% | 0.038 |
| T2 0.14% | 0.032 |
| T2 0.014% | 0.035 |
| T3 0.14% | 0.039 |
| T3 0.014% | 0.053 |
| T4 0.14% | 0.026 |
| T4 0.014% | 0.052 |

The purpose of these studies was to determine if RSPP test material GC2596-26-D describe above could provide protection against UVB-induced damage in cultured dermal fibroblasts. In the initial study, two duplicate sets of cultured fibroblasts were exposed to six concentrations of the test material. The first set of cells was exposed to approximately 50 mj/cm$^2$ of UVB, followed immediately by the application of either the test material, 20 µM Trolox (an anti-oxidant, used as a positive control), or left untreated (untreated controls). The second set of cells did not receive a dose of UVB and was only exposed to either the test material, Trolox, or left untreated. Changes in cell viability were then determined 48 hours post material application via an MTT assay.

Table 25 shows the results for this first study. With respect to the untreated cells, the dose of UVB was observed to induce an approximate 45% decrease in the number of viable cells (Untreated −UVB vs. Untreated +UVB). However, in the presence of the test material, this decrease in the number of viable cells induced by +UVB appears to be inhibited in a dose-dependent manner. This effect was most prominent at the highest concentration of test material used (0.14%), where the level of cell viability (104%) is nearly identical to the untreated −UVB exposed cells and almost twice the level of the untreated +UVB exposed cells. As the concentration of the test material decreased, so did the apparent protective effect, although even at the lowest level of the material, 0.0007%, the number of viable cells is still slightly greater than the +UVB untreated controls (69% vs. 55%, respectively).

It was also observed that in the absence of UVB light, RSPP test material GC2596-26-D could also stimulate cell proliferation in a dose dependent manner. At the highest concentration tested (0.14%), the number of viable cells in the −UVB condition was observed to be 54% greater than the −UVB untreated cells. This stimulation effect was apparent over the entire range of material D tested, with the level of proliferation decreasing as the concentration of the material decreased.

Although it is not intended that the present invention be limited to any particular mechanism, it is hypothesized that the material protects the cells by limiting the amount of damage or facilitates the repair of the damage. Thus, the population of viable cells is better maintained than it is in the untreated condition. This hypothesis is supported by the fact that the increase in the number of viable cells tends to be greater between the +UVB untreated and the +UVB 0.14% test material conditions (50% viability vs. 100% viability, respectively, double the number of viable cells) than in the −UVB untreated and the −UVB test material conditions (100% viability vs. 150% viability, respectively, only a 50% increase). This suggests that in the presence of UVB there is a greater increase in the number of viable cells than can be accounted for by purely stimulating cell proliferation in the surviving cells alone, and supports the explanation that the RSPP test material GC2596-26-D does provide protection against UVB induced damage.

Since the results of the initial MTT study suggested that the RSPP test material GC2596-26-D was capable of improving cell survival when it was applied after UVB exposure, a follow up study was conducted to determine if treatment with the test material before or during UVB exposure provided any additional survival benefit. Four different treatment regiments were employed using different combinations of pre-treatment with the test material prior to UVB exposure and treatment with the material during UVB exposure. Cell survival was again assessed via an MTT assay 48 hours after the UVB insult. In addition, this second study also incorporated the use of 2',7'-dichloro-dihydrofluorescein diacetate (DCF), which is a relatively non-fluorescent dye that can be loaded into cells and becomes fluorescent upon exposure to the reactive oxygen species (ROS) generated during UVB exposure (Carini et al., supra; and Chan et al., supra). The diacetate form of the dye can freely traverse cell membranes, however once inside of the cell intracellular esterases will cleave off the acetate side groups trapping the DCF dye within the cell.

The results from the follow up experiments confirmed the UVB protective effect of the test material when applied post UVB exposure, and also indicated that its protective effect was improved when the material was also present both before and/or during UVB exposure. In this follow up study, Treatment 3 was identical to the treatment regimen used in the initial experiments, with the test material being applied after the UVB exposure, and shows similar results with respect to the MTT assay (See, Table 26). At the 0.14% concentration, cell viability after UVB exposure was again found to be close to 100% after the UVB exposure (vs. 104% in the initial study), and at the 0.014% concentration, cell viability was 88% (vs. 83% in the initial study). At both concentrations the amount of cell survival was greater than the amount of cell survival in the untreated cells. In addition, the use of the DCF dye allowed for an estimate of the amount of oxidative damage occurring within the cell as a result of the UVB exposure (See, Table 27). For this marker, the greater the value of the ratio, the greater the extent of the ROS formation within the cell. With respect to Treatment 3, both concentrations of the test material were observed to reduce the amount of ROS formed in a concentration-dependent manner, when compared to the +UVB control. These results confirm observations from the earlier study and further support that the test material 2596-26-D can provide UVB protection.

Treatments 1 and 2 incorporated a 24-hour pretreatment phase with the test material prior to the UVB exposure, with treatment 2 also having the test material present during the UVB exposure phase as well. When the material was present at 0.14%, cell viabilities in both treatments were greater than both the +UVB and −UVB controls. This may be mainly due to the fact that since this material stimulates cell proliferation, the cells undergoing the 24-hour pretreatment were growing at a faster rate than the rest of the cells in the experiment. However, the data from the DCF assay indicates that this pretreatment was effective in reducing the amount of ROS formation. Interestingly, the DCF assay also indicates that the material effectively reduced ROS formation at the 0.014% concentration, although the data from the MTT assay only shows a small increase in cell viability with this concentration of material D. Both Treatment 1 and 2 produced similar results, with Treatment 2 resulting in slightly less ROS formation, suggesting that the 24 hour pretreatment alone may be sufficient in providing protection and that having the material present again during UVB exposure may only provide minimal additional benefits.

The final Treatment (i.e., Treatment 4), involved having the material present during the UVB exposure. At 0.14% concentration, cell viability and ROS formation is comparable to Treatments 1 and 2 and clearly demonstrates a UVB protective effect. Thus it appears that having the material around at the 0.14% concentration either for 24 hour before exposure, or just during exposure provides a similar level of protection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, cosmetic formulations, protein biology, and molecular biology, as well as related fields are intended to be within the scope of the present invention.

SEQUENCE LISTING

```
<160> NUMBER OF SEQ ID NOS: 37

<210> SEQ ID NO 1
<211> LENGTH: 6
<212> TYPE: PRT
<213> ORGANISM: Artificial Sequence
<220> FEATURE:
<223> OTHER INFORMATION: synthetic silk-like protein

<400> SEQUENCE: 1

Ser Gly Ala Gly Ala Gly
1               5

<210> SEQ ID NO 2
<211> LENGTH: 59
<212> TYPE: PRT
<213> ORGANISM: Unknown
<220> FEATURE:
<223> OTHER INFORMATION: silk fibroin protein

<400> SEQUENCE: 2

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45
```

```
Gly Ala Gly Ala Gly Ser Gly Ala Ala Gly Tyr
        50                  55
```

```
<210> SEQ ID NO 3
<211> LENGTH: 5
<212> TYPE: PRT
<213> ORGANISM: Artificial Sequence
<220> FEATURE:
<223> OTHER INFORMATION: synthetic elastin-like protein

<400> SEQUENCE: 3

Gly Val Gly Val Pro
1               5
```

```
<210> SEQ ID NO 4
<211> LENGTH: 10
<212> TYPE: PRT
<213> ORGANISM: Artificial Sequence
<220> FEATURE:
<223> OTHER INFORMATION: synthetic abductin-like protein
<220> FEATURE:
<221> NAME/KEY: VARIANT
<222> LOCATION: 10
<223> OTHER INFORMATION: Xaa = Any Amino Acid

<400> SEQUENCE: 4

Gly Gly Phe Gly Gly Met Gly Gly Gly Xaa
1               5                   10
```

```
<210> SEQ ID NO 5
<211> LENGTH: 5
<212> TYPE: PRT
<213> ORGANISM: Artificial Sequence
<220> FEATURE:
<223> OTHER INFORMATION: synthetic byssus-like protein

<400> SEQUENCE: 5

Gly Pro Gly Gly Gly
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: synthetic gluten-like protein

<400> SEQUENCE: 6

Pro Gly Gln Gly Gln Gln
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: synthetic gluten-like protein

<400> SEQUENCE: 7

Gly Tyr Tyr Pro Thr Ser Pro Gln Gln
1               5
```

```
<210> SEQ ID NO 8
<211> LENGTH: 3
<212> TYPE: PRT
<213> ORGANISM: Artificial Sequence
<220> FEATURE:
<223> OTHER INFORMATION: synthetic gluten-like protein
```

<400> SEQUENCE: 8

Gly Gln Gln
1

<210> SEQ ID NO 9
<211> LENGTH: 28
<212> TYPE: PRT
<213> ORGANISM: Artificial Sequence
<220> FEATURE:
<223> OTHER INFORMATION: synthetic titin-like protein

<400> SEQUENCE: 9

Pro Pro Ala Lys Val Pro Glu Val Pro Lys Lys Pro Val Pro Glu Glu
1               5                   10                  15

Lys Val Pro Val Pro Val Pro Lys Lys Pro Glu Ala
            20                  25

<210> SEQ ID NO 10
<211> LENGTH: 12
<212> TYPE: PRT
<213> ORGANISM: Artificial Sequence
<220> FEATURE:
<223> OTHER INFORMATION: synthetic extensin-like protein

<400> SEQUENCE: 10

Ser Pro Pro Pro Pro Ser Pro Lys Tyr Val Tyr Lys
1               5                   10

<210> SEQ ID NO 11
<211> LENGTH: 4
<212> TYPE: PRT
<213> ORGANISM: Artificial Sequence
<220> FEATURE:
<223> OTHER INFORMATION: synthetic fibronectin-like protein

<400> SEQUENCE: 11

Arg Gly Asp Ser
1

<210> SEQ ID NO 12
<211> LENGTH: 5
<212> TYPE: PRT
<213> ORGANISM: Unknown
<220> FEATURE:
<223> OTHER INFORMATION: gliadin

<400> SEQUENCE: 12

Pro Gln Gln Pro Tyr
1               5

<210> SEQ ID NO 13
<211> LENGTH: 5
<212> TYPE: PRT
<213> ORGANISM: Unknown
<220> FEATURE:
<223> OTHER INFORMATION: glue polypeptide

<400> SEQUENCE: 13

Pro Thr Thr Thr Lys
1               5

<210> SEQ ID NO 14
<211> LENGTH: 8
<212> TYPE: PRT
<213> ORGANISM: Unknown
<220> FEATURE:

```
<223> OTHER INFORMATION: ice nucleating protein

<400> SEQUENCE: 14

Ala Gly Tyr Gly Ser Thr Gly Thr
1               5

<210> SEQ ID NO 15
<211> LENGTH: 8
<212> TYPE: PRT
<213> ORGANISM: Unknown
<220> FEATURE:
<223> OTHER INFORMATION: keratin

<400> SEQUENCE: 15

Tyr Gly Gly Ser Ser Gly Gly Gly
1               5

<210> SEQ ID NO 16
<211> LENGTH: 5
<212> TYPE: PRT
<213> ORGANISM: Unknown
<220> FEATURE:
<223> OTHER INFORMATION: keratin

<400> SEQUENCE: 16

Phe Gly Gly Gly Ser
1               5

<210> SEQ ID NO 17
<211> LENGTH: 6
<212> TYPE: PRT
<213> ORGANISM: Unknown
<220> FEATURE:
<223> OTHER INFORMATION: mucin

<400> SEQUENCE: 17

Thr Thr Thr Pro Asp Val
1               5

<210> SEQ ID NO 18
<211> LENGTH: 7
<212> TYPE: PRT
<213> ORGANISM: Unknown
<220> FEATURE:
<223> OTHER INFORMATION: RNA polymerase II

<400> SEQUENCE: 18

Tyr Ser Pro Thr Ser Pro Ser
1               5

<210> SEQ ID NO 19
<211> LENGTH: 780
<212> TYPE: PRT
<213> ORGANISM: Unknown
<220> FEATURE:
<223> OTHER INFORMATION: SELP 47K

<400> SEQUENCE: 19

Gly Ala Gly Ala Gly Ser Gly Ala Gly Ala Ser Gly Val Gly Val
1               5                   10                  15

Pro Gly Val Gly Val Pro Gly Val Gly Val Pro Gly Lys Gly Val Pro
            20                  25                  30

Gly Val Gly Pro Gly Val Gly Pro Gly Val Gly Pro Gly Val Gly Pro
        35                  40                  45

Gly Ala Gly Ala Gly Ser Gly Ala Gly Ala Gly Ser Gly Ala Gly Ala
    50                  55                  60
```

```
Gly Ser Gly Ala Gly Ala Gly Ser Gly Val Gly Val Pro Gly Val Gly
65                  70                  75                  80

Val Pro Gly Val Gly Val Pro Gly Lys Gly Val Pro Gly Val Gly Pro
                85                  90                  95

Gly Val Gly Pro Gly Val Gly Pro Gly Val Gly Pro Gly Ala Gly Ala
                100                 105                 110

Gly Ser Gly Ala Gly Ala Gly Ser Gly Ala Gly Ala Gly Ser Gly Ala
                115                 120                 125

Gly Ala Gly Ser Gly Val Gly Val Pro Gly Val Gly Val Pro Gly Val
            130                 135                 140

Gly Val Pro Gly Lys Gly Val Pro Gly Val Gly Pro Gly Val Gly Pro
145                 150                 155                 160

Gly Val Gly Pro Gly Val Gly Pro Gly Ala Gly Ala Gly Ser Gly Ala
                165                 170                 175

Gly Ala Gly Ser Gly Ala Gly Ala Gly Ser Gly Ala Gly Ala Gly Ser
            180                 185                 190

Gly Val Gly Val Pro Gly Val Gly Val Pro Gly Val Gly Val Pro Gly
        195                 200                 205

Lys Gly Val Pro Gly Val Gly Pro Gly Val Gly Pro Gly Val Gly Pro
    210                 215                 220

Gly Val Gly Pro Gly Ala Gly Ala Gly Ser Gly Ala Gly Ala Gly Ser
225                 230                 235                 240

Gly Ala Gly Ala Gly Ser Gly Ala Gly Ala Gly Ser Gly Val Gly Val
                245                 250                 255

Pro Gly Val Gly Val Pro Gly Val Gly Val Pro Gly Lys Gly Val Pro
                260                 265                 270

Gly Val Gly Pro Gly Val Gly Pro Gly Val Gly Pro Gly Val Gly Pro
            275                 280                 285

Gly Ala Gly Ala Gly Ser Gly Ala Gly Ala Gly Ser Gly Ala Gly Ala
290                 295                 300

Gly Ser Gly Ala Gly Ala Gly Ser Gly Val Gly Val Pro Gly Val Gly
305                 310                 315                 320

Val Pro Gly Val Gly Val Pro Gly Lys Gly Val Pro Gly Val Gly Pro
                325                 330                 335

Gly Val Gly Pro Gly Val Gly Pro Gly Val Gly Pro Gly Ala Gly Ala
                340                 345                 350

Gly Ser Gly Ala Gly Ala Gly Ser Gly Ala Gly Ala Gly Ser Gly Ala
                355                 360                 365

Gly Ala Gly Ser Gly Val Gly Val Pro Gly Val Gly Val Pro Gly Val
            370                 375                 380

Gly Val Pro Gly Lys Gly Val Pro Gly Val Gly Pro Gly Val Gly Pro
385                 390                 395                 400

Gly Val Gly Pro Gly Val Gly Pro Gly Ala Gly Ala Gly Ser Gly Ala
                405                 410                 415

Gly Ala Gly Ser Gly Ala Gly Ala Gly Ser Gly Ala Gly Ala Gly Ser
            420                 425                 430

Gly Val Gly Val Pro Gly Val Gly Val Pro Gly Val Gly Val Pro Gly
        435                 440                 445

Lys Gly Val Pro Gly Val Gly Pro Gly Val Gly Pro Gly Val Gly Pro
    450                 455                 460

Gly Val Gly Pro Gly Ala Gly Ala Gly Ser Gly Ala Gly Ala Gly Ser
465                 470                 475                 480

Gly Ala Gly Ala Gly Ser Gly Ala Gly Ala Gly Ser Gly Val Gly Val
```

```
                485                 490                 495
Pro Gly Val Gly Val Pro Gly Val Gly Val Pro Gly Lys Gly Val Pro
            500                 505                 510
Gly Val Gly Pro Gly Val Gly Pro Gly Val Gly Pro Gly Val Gly Pro
            515                 520                 525
Gly Ala Gly Ala Gly Ser Gly Ala Gly Ala Gly Ser Gly Ala Gly Ala
            530                 535                 540
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
                565                 570                 575
Gly Val Gly Pro Gly Val Gly Pro Gly Val Gly Pro Gly Ala Gly Ala
            580                 585                 590
Gly Ser Gly Ala Gly Ala Gly Ser Gly Ala Gly Ala Gly Ser Gly Ala
            595                 600                 605
Gly Ala Gly Ser Gly Val Gly Val Pro Gly Val Gly Val Pro Gly Val
            610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
                645                 650                 655
Gly Ala Gly Ser Gly Ala Gly Ala Gly Ser Gly Ala Gly Ala Gly Ser
            660                 665                 670
Gly Val Gly Val Pro Gly Val Gly Val Pro Gly Val Gly Val Pro Gly
            675                 680                 685
Lys Gly Val Pro Gly Val Gly Pro Gly Val Gly Pro Gly Val Gly Pro
690                 695                 700
Gly Val Gly Pro Gly Ala Gly Ala Gly Ser Gly Ala Gly Ala Gly Ser
705                 710                 715                 720
Gly Ala Gly Ala Gly Ser Gly Ala Gly Ala Gly Ser Gly Val Gly Val
                725                 730                 735
Pro Gly Val Gly Val Pro Gly Val Gly Val Pro Gly Lys Gly Val Pro
            740                 745                 750
Gly Val Gly Pro Gly Val Gly Pro Gly Val Gly Pro Gly Val Gly Pro
            755                 760                 765
Gly Ala Gly Ala Gly Ser Gly Ala Gly Ala Gly Ser
            770                 775                 780

<210> SEQ ID NO 20
<211> LENGTH: 3
<212> TYPE: PRT
<213> ORGANISM: Artificial Sequence
<220> FEATURE:
<223> OTHER INFORMATION: synthetic abductin-like protein
<220> FEATURE:
<221> NAME/KEY: VARIANT
<222> LOCATION: 1
<223> OTHER INFORMATION: Xaa = Any Amino Acid, preferably Ala or Pro
<220> FEATURE:
<221> NAME/KEY: VARIANT
<222> LOCATION: 2
<223> OTHER INFORMATION: Xaa = Any Amino Acid, preferably Pro or
      hydroxy-Pro

<400> SEQUENCE: 20

Gly Xaa Xaa
 1

<210> SEQ ID NO 21
```

```
<211> LENGTH: 39
<212> TYPE: DNA
<213> ORGANISM: Artificial Sequence
<220> FEATURE:
<223> OTHER INFORMATION: primer

<400> SEQUENCE: 21
gggagttggt gtacctggag aaggtgttcc gggggtagg                          39

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
cctacccccg gaacaccttc tccaggtaca ccaactccc                          39

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
gggagttggg gtacctggac gaggtgttcc gggggtagg                          39

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24 cctaccccccc caaggtggag ctccaggtac cccaactccc                        40

<210> SEQ ID NO 25
<211> LENGTH: 884
<212> TYPE: PRT
<213> ORGANISM: Unknown
<220> FEATURE:
<223> OTHER INFORMATION: SELP 47E-13

<400> SEQUENCE: 25
```

Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
             20                  25                  30

Met Gly Ala Gly Ser Gly Ala Gly Ala Gly Ser Gly Val Gly Val Pro
         35                  40                  45

Gly Val Gly Val Pro Gly Val Gly Val Pro Gly Val Gly Val Pro Gly
     50                  55                  60

Glu Gly Val Pro Gly Val Gly Val Pro Gly Val Gly Glu Pro Gly Val
 65                  70                  75                  80

Gly Val Pro Gly Ala Gly Ala Gly Ser Gly Ala Gly Ala Gly Ser Gly
                 85                  90                  95

Ala Gly Ala Gly Ser Gly Ala Gly Ala Gly Ser Gly Val Gly Val Pro
                100                 105                 110

Gly Val Gly Val Pro Gly Val Gly Val Pro Gly Val Gly Val Pro Gly
            115                 120                 125

-continued

```
Glu Gly Val Pro Gly Val Gly Val Pro Gly Val Glu Pro Gly Val
130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
                165                 170                 175
Gly Val Gly Val Pro Gly Val Gly Val Pro Gly Val Gly Val Pro Gly
                180                 185                 190
Glu Gly Val Pro Gly Val Gly Val Pro Gly Val Gly Glu Pro Gly Val
                195                 200                 205
Gly Val Pro Gly Ala Gly Ala Gly Ser Gly Ala Gly Ala Gly Ser Gly
210                 215                 220
Ala Gly Ala Gly Ser Gly Ala Gly Ala Gly Ser Gly Val Gly Val Pro
225                 230                 235                 240
Gly Val Gly Val Pro Gly Val Gly Val Pro Gly Val Gly Val Pro Gly
                245                 250                 255
Glu Gly Val Pro Gly Val Gly Val Pro Gly Val Gly Glu Pro Gly Val
                260                 265                 270
Gly Val Pro Gly Ala Gly Ala Gly Ser Gly Ala Gly Ala Gly Ser Gly
                275                 280                 285
Ala Gly Ala Gly Ser Gly Ala Gly Ala Gly Ser Gly Val Gly Val Pro
290                 295                 300
Gly Val Gly Val Pro Gly Val Gly Val Pro Gly Val Gly Val Pro Gly
305                 310                 315                 320
Glu Gly Val Pro Gly Val Gly Val Pro Gly Val Gly Glu Pro Gly Val
                325                 330                 335
Gly Val Pro Gly Ala Gly Ala Gly Ser Gly Ala Gly Ala Gly Ser Gly
                340                 345                 350
Ala Gly Ala Gly Ser Gly Ala Gly Ala Gly Ser Gly Val Gly Val Pro
                355                 360                 365
Gly Val Gly Val Pro Gly Val Gly Val Pro Gly Val Gly Val Pro Gly
                370                 375                 380
Glu Gly Val Pro Gly Val Gly Val Pro Gly Val Gly Glu Pro Gly Val
385                 390                 395                 400
Gly Val Pro Gly Ala Gly Ala Gly Ser Gly Ala Gly Ala Gly Ser Gly
                405                 410                 415
Ala Gly Ala Gly Ser Gly Ala Gly Ala Gly Ser Gly Val Gly Val Pro
                420                 425                 430
Gly Val Gly Val Pro Gly Val Gly Val Pro Gly Val Gly Val Pro Gly
                435                 440                 445
Glu Gly Val Pro Gly Val Gly Val Pro Gly Val Gly Glu Pro Gly Val
                450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
                485                 490                 495
Gly Val Gly Val Pro Gly Val Gly Val Pro Gly Val Gly Val Pro Gly
                500                 505                 510
Glu Gly Val Pro Gly Val Gly Val Pro Gly Val Gly Glu Pro Gly Val
                515                 520                 525
Gly Val Pro Gly Ala Gly Ala Gly Ser Gly Ala Gly Ala Gly Ser Gly
                530                 535                 540
Ala Gly Ala Gly Ser Gly Ala Gly Ala Gly Ser Gly Val Gly Val Pro
545                 550                 555                 560
```

Gly Val Gly Val Pro Gly Val Gly Val Pro Gly Val Gly Val Pro Gly
                565                 570                 575

Glu Gly Val Pro Gly Val Gly Val Pro Gly Val Gly Glu Pro Gly Val
            580                 585                 590

Gly Val Pro Gly Ala Gly Ala Gly Ser Gly Ala Gly Ala Gly Ser Gly
        595                 600                 605

Ala Gly Ala Gly Ser Gly Ala Gly Ala Gly Ser Gly Val Gly Val Pro
    610                 615                 620

Gly Val Gly Val Pro Gly Val Gly Val Pro Gly Val Gly Val Pro Gly
625                 630                 635                 640

Glu Gly Val Pro Gly Val Gly Val Pro Gly Val Gly Glu Pro Gly Val
            645                 650                 655

Gly Val Pro Gly Ala Gly Ala Gly Ser Gly Ala Gly Ala Gly Ser Gly
        660                 665                 670

Ala Gly Ala Gly Ser Gly Ala Gly Ala Gly Ser Gly Val Gly Val Pro
    675                 680                 685

Gly Val Gly Val Pro Gly Val Gly Val Pro Gly Val Gly Val Pro Gly
        690                 695                 700

Glu Gly Val Pro Gly Val Gly Val Pro Gly Val Gly Glu Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Val Gly Val Pro
        740                 745                 750

Gly Val Gly Val Pro Gly Val Gly Val Pro Gly Val Gly Val Pro Gly
    755                 760                 765

Glu Gly Val Pro Gly Val Gly Val Pro Gly Val Gly Glu Pro Gly Val
        770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
            805                 810                 815

Gly Val Gly Val Pro Gly Val Gly Val Pro Gly Val Gly Val Pro Gly
        820                 825                 830

Glu Gly Val Pro Gly Val Gly Val Pro Gly Val Gly Glu Pro Gly Val
    835                 840                 845

Gly Val Pro Gly Ala Gly Ala Gly Ser Gly Ala Gly Ala Gly Ser Gly
850                 855                 860

Ala Gly Ala Met Asp Pro Gly Arg Tyr Gln Asp Leu Arg Ser His His
865                 870                 875                 880

His His His His

<210> SEQ ID NO 26
<211> LENGTH: 246
<212> TYPE: PRT
<213> ORGANISM: Unknown
<220> FEATURE:
<223> OTHER INFORMATION: SELP 47R-3

<400> SEQUENCE: 26

Met Pro Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Pro
             20                  25                  30

Met Gly Ala Gly Ala Gly Ser Gly Ala Gly Ala Gly Ser Gly Val Gly

-continued

```
                35                  40                  45
Val Pro Gly Val Gly Val Pro Gly Val Gly Val Pro Gly Val Gly Val
 50                  55                  60

Pro Gly Arg Gly Val Pro Gly Val Gly Val Pro Gly Val Gly Val Pro
 65                  70                  75                  80

Gly Val Gly Val Pro Gly Ala Gly Ala Gly Ser Gly Ala Gly Ala Gly
                 85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
            115                 120                 125

Pro Gly Arg Gly Val Pro Gly Val Gly Val Pro Gly Val Gly Val Pro
130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Arg Gly Val Pro Gly Val Gly Val Pro Gly Val Gly Val Pro
            195                 200                 205

Gly Val Gly Val Pro Gly Ala Gly Ala Gly Ser Gly Ala Gly Ala Gly
        210                 215                 220

Ser Gly Ala Gly Ala Met Asp Pro Gly Arg Tyr Gln Asp Leu Arg Ser
225                 230                 235                 240

His His His His His His
                245

<210> SEQ ID NO 27
<211> LENGTH: 244
<212> TYPE: PRT
<213> ORGANISM: Unknown
<220> FEATURE:
<223> OTHER INFORMATION: SELP-47K-3

<400> SEQUENCE: 27

Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
 50                  55                  60

Lys Gly Val Pro Gly Val Gly Val Pro Gly Val Gly Val Pro Gly Val
 65                  70                  75                  80

Gly Val Pro Gly Ala Gly Ala Gly Ser Gly Ala Gly Ala Gly Ser Gly
                 85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
            115                 120                 125

Lys Gly Val Pro Gly Val Gly Val Pro Gly Val Gly Val Pro Gly Val
        130                 135                 140

Gly Val Pro Gly Ala Gly Ala Gly Ser Gly Ala Gly Ala Gly Ser Gly
145                 150                 155                 160
```

```
Ala Gly Ala Gly Ser Gly Ala Gly Ser Gly Val Gly Val Pro
            165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
210                 215                 220

Ala Gly Ala Met Asp Pro Gly Arg Tyr Gln Asp Leu Arg Ser His His
225                 230                 235                 240

His His His His
```

<210> SEQ ID NO 28
<211> LENGTH: 246
<212> TYPE: PRT
<213> ORGANISM: Unknown
<220> FEATURE:
<223> OTHER INFORMATION: SELP 47E-3

<400> SEQUENCE: 28

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
            35                  40                  45

Val Pro Gly Val Gly Val Pro Gly Val Gly Val Pro Gly Val Gly Val
 50                  55                  60

Pro Gly Glu Gly Val Pro Gly Val Gly Val Pro Gly Val Gly Val Pro
65                   70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
            115                 120                 125

Pro Gly Glu Gly Val Pro Gly Val Gly Val Pro Gly Val Gly Val Pro
            130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
            165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
            195                 200                 205

Gly Val Gly Val Pro Gly Ala Gly Ala Gly Ser Gly Ala Gly Ala Gly
            210                 215                 220

Ser Gly Ala Gly Ala Met Asp Pro Gly Arg Tyr Gln Asp Leu Arg Ser
225                 230                 235                 240

His His His His His His
                245
```

<210> SEQ ID NO 29
<211> LENGTH: 1063
<212> TYPE: PRT

<213> ORGANISM: Artificial Sequence
<220> FEATURE:
<223> OTHER INFORMATION: synthetic collagen-like protein

<400> SEQUENCE: 29

```
Met Asp Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Pro
             20                  25                  30

Met Gly Ala His Gly Pro Ala Gly Pro Lys Gly Ala His Gly Pro Ala
         35                  40                  45

Gly Pro Lys Gly Ala Gln Gly Pro Ala Gly Pro Gly Gly Ala Gln Gly
     50                  55                  60

Pro Ala Gly Pro Gly Gly Ala Gln Gly Pro Ala Gly Pro Gly Gly Ala
 65                  70                  75                  80

Gln Gly Pro Ala Gly Pro Gly Gly Ala Gln Gly Pro Ala Gly Pro Gly
                 85                  90                  95

Gly Ala Gln Gly Pro Ala Gly Pro Gly Gly Ala Gln Gly Pro Ala Gly
            100                 105                 110

Pro Gly Gly Ala Gln Gly Pro Ala Gly Pro Gly Gly Ala Gln Gly Pro
        115                 120                 125

Ala Gly Pro Gly Gly Ala Gln Gly Pro Ala Gly Pro Gly Gly Ala Gln
130                 135                 140

Gly Pro Ala Gly Pro Gly Gly Ala Gln Gly Pro Ala Gly Pro Gly Gly
145                 150                 155                 160

Ala Gln Gly Pro Ala Gly Pro Gly Gly Ala Gln Gly Pro Ala Gly Pro
                165                 170                 175

Gly Gly Ala Gln Gly Pro Ala Gly Pro Gly Gly Ala Gln Gly Pro Ala
            180                 185                 190

Gly Pro Gly Gly Ala Gln Gly Pro Ala Gly Pro Gly Gly Ala Gln Gly
        195                 200                 205

Pro Ala Gly Pro Gly Gly Ala Gln Gly Pro Ala Gly Pro Gly Gly Ala
    210                 215                 220

Gln Gly Pro Ala Gly Pro Gly Gly Ala Gln Gly Pro Ala Gly Pro Gly
225                 230                 235                 240

Gly Ala Gln Gly Pro Ala Gly Pro Gly Gly Ala Gln Gly Pro Ala Gly
                245                 250                 255

Pro Gly Gly Ala Gln Gly Pro Ala Gly Pro Gly Gly Ala His Gly Pro
            260                 265                 270

Ala Gly Pro Lys Gly Ala His Gly Pro Ala Gly Pro Lys Gly Ala His
        275                 280                 285

Gly Pro Ala Gly Pro Lys Gly Ala His Gly Pro Ala Gly Pro Lys Gly
    290                 295                 300

Ala Gln Gly Pro Ala Gly Pro Gly Gly Ala Gln Gly Pro Ala Gly Pro
305                 310                 315                 320

Gly Gly Ala Gln Gly Pro Ala Gly Pro Gly Gly Ala Gln Gly Pro Ala
                325                 330                 335

Gly Pro Gly Gly Ala Gln Gly Pro Ala Gly Pro Gly Gly Ala Gln Gly
            340                 345                 350

Pro Ala Gly Pro Gly Gly Ala Gln Gly Pro Ala Gly Pro Gly Gly Ala
        355                 360                 365

Gln Gly Pro Ala Gly Pro Gly Gly Ala Gln Gly Pro Ala Gly Pro Gly
    370                 375                 380

Gly Ala Gln Gly Pro Ala Gly Pro Gly Gly Ala Gln Gly Pro Ala Gly
385                 390                 395                 400
```

```
Pro Gly Gly Ala Gln Gly Pro Ala Gly Pro Gly Gly Ala Gln Gly Pro
                405                 410                 415
Ala Gly Pro Gly Gly Ala Gln Gly Pro Ala Gly Pro Gly Gly Ala Gln
            420                 425                 430
Gly Pro Ala Gly Pro Gly Gly Ala Gln Gly Pro Ala Gly Pro Gly Gly
        435                 440                 445
Ala Gln Gly Pro Ala Gly Pro Gly Gly Ala Gln Gly Pro Ala Gly Pro
    450                 455                 460
Gly Gly Ala Gln Gly Pro Ala Gly Pro Gly Gly Ala Gln Gly Pro Ala
465                 470                 475                 480
Gly Pro Gly Gly Ala Gln Gly Pro Ala Gly Pro Gly Gly Ala Gln Gly
                485                 490                 495
Pro Ala Gly Pro Gly Gly Ala Gln Gly Pro Ala Gly Pro Gly Gly Ala
            500                 505                 510
Gln Gly Pro Ala Gly Pro Gly Gly Ala His Gly Pro Ala Gly Pro Lys
        515                 520                 525
Gly Ala His Gly Pro Ala Gly Pro Lys Gly Ala His Gly Pro Ala Gly
    530                 535                 540
Pro Lys Gly Ala His Gly Pro Ala Gly Pro Lys Gly Ala Gln Gly Pro
545                 550                 555                 560
Ala Gly Pro Gly Gly Ala Gln Gly Pro Ala Gly Pro Gly Gly Ala Gln
                565                 570                 575
Gly Pro Ala Gly Pro Gly Gly Ala Gln Gly Pro Ala Gly Pro Gly Gly
            580                 585                 590
Ala Gln Gly Pro Ala Gly Pro Gly Gly Ala Gln Gly Pro Ala Gly Pro
        595                 600                 605
Gly Gly Ala Gln Gly Pro Ala Gly Pro Gly Gly Ala Gln Gly Pro Ala
    610                 615                 620
Gly Pro Gly Gly Ala Gln Gly Pro Ala Gly Pro Gly Gly Ala Gln Gly
625                 630                 635                 640
Pro Ala Gly Pro Gly Gly Ala Gln Gly Pro Ala Gly Pro Gly Gly Ala
                645                 650                 655
Gln Gly Pro Ala Gly Pro Gly Gly Ala Gln Gly Pro Ala Gly Pro Gly
            660                 665                 670
Gly Ala Gln Gly Pro Ala Gly Pro Gly Gly Ala Gln Gly Pro Ala Gly
        675                 680                 685
Pro Gly Gly Ala Gln Gly Pro Ala Gly Pro Gly Gly Ala Gln Gly Pro
    690                 695                 700
Ala Gly Pro Gly Gly Ala Gln Gly Pro Ala Gly Pro Gly Gly Ala Gln
705                 710                 715                 720
Gly Pro Ala Gly Pro Gly Gly Ala Gln Gly Pro Ala Gly Pro Gly Gly
                725                 730                 735
Ala Gln Gly Pro Ala Gly Pro Gly Gly Ala Gln Gly Pro Ala Gly Pro
            740                 745                 750
Gly Gly Ala Gln Gly Pro Ala Gly Pro Gly Gly Ala Gln Gly Pro Ala
        755                 760                 765
Gly Pro Gly Gly Ala His Gly Pro Ala Gly Pro Lys Gly Ala His Gly
    770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
                805                 810                 815
Gly Ala Gln Gly Pro Ala Gly Pro Gly Gly Ala Gln Gly Pro Ala Gly
```

-continued

```
                820                 825                 830
Pro Gly Gly Ala Gln Gly Pro Ala Gly Pro Gly Gly Ala Gln Gly Pro
            835                 840                 845
Ala Gly Pro Gly Gly Ala Gln Gly Pro Ala Gly Pro Gly Gly Ala Gln
        850                 855                 860
Gly Pro Ala Gly Pro Gly Gly Ala Gln Gly Pro Ala Gly Pro Gly Gly
865                 870                 875                 880
Ala Gln Gly Pro Ala Gly Pro Gly Gly Ala Gln Gly Pro Ala Gly Pro
                885                 890                 895
Gly Gly Ala Gln Gly Pro Ala Gly Pro Gly Gly Ala Gln Gly Pro Ala
            900                 905                 910
Gly Pro Gly Gly Ala Gln Gly Pro Ala Gly Pro Gly Gly Ala Gln Gly
        915                 920                 925
Pro Ala Gly Pro Gly Gly Ala Gln Gly Pro Ala Gly Pro Gly Gly Ala
    930                 935                 940
Gln Gly Pro Ala Gly Pro Gly Gly Ala Gln Gly Pro Ala Gly Pro Gly
945                 950                 955                 960
Gly Ala Gln Gly Pro Ala Gly Pro Gly Gly Ala Gln Gly Pro Ala Gly
                965                 970                 975
Pro Gly Gly Ala Gln Gly Pro Ala Gly Pro Gly Gly Ala Gln Gly Pro
            980                 985                 990
Ala Gly Pro Gly Gly Ala Gln Gly Pro Ala Gly Pro Gly Gly Ala Gln
        995                 1000                1005
Gly Pro Ala Gly Pro Gly Gly Ala Gln Gly Pro Ala Gly Pro Gly Gly
        1010                1015                1020
Ala His Gly Pro Ala Gly Pro Lys Gly Ala His Gly Pro Ala Gly Pro
1025                1030                1035                1040
Lys Met Asp Pro Gly Arg Tyr Gln Leu Ser Ala Gly Arg Tyr His Tyr
                1045                1050                1055
Gln Leu Val Trp Cys Gln Lys
            1060

<210> SEQ ID NO 30
<211> LENGTH: 1038
<212> TYPE: PRT
<213> ORGANISM: Unknown
<220> FEATURE:
<223> OTHER INFORMATION: SELP 67K

<400> SEQUENCE: 30

Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
            20                  25                  30
Met Gly Val Gly Val Pro Gly Val Gly Val Pro Gly Val Gly Val Pro
        35                  40                  45
Gly Val Gly Val Pro Gly Lys Gly Val Pro Gly Val Gly Val Pro Gly
    50                  55                  60
Val Gly Val Pro Gly Val Gly Val Pro Gly Ala Gly Ala Gly Ser Gly
65                  70                  75                  80
Ala Gly Ala Gly Ser Gly Ala Gly Ala Gly Ser Gly Ala Gly Ala Gly
                85                  90                  95
Ser Gly Ala Gly Ala Gly Ser Gly Ala Gly Ala Gly Ser Gly Val Gly
            100                 105                 110
Val Pro Gly Val Gly Val Pro Gly Val Gly Val Pro Gly Val Gly Val
        115                 120                 125
```

-continued

```
Pro Gly Lys Gly Val Pro Gly Val Gly Val Pro Gly Val Gly Val Pro
        130                 135                 140
Gly Val Gly Val Pro Gly Ala Gly Ala Gly Ser Gly Ala Gly Ala Gly
145                 150                 155                 160
Ser Gly Ala Gly Ala Gly Ser Gly Ala Gly Ala Gly Ser Gly Ala Gly
                165                 170                 175
Ala Gly Ser Gly Ala Gly Ala Gly Ser Gly Val Gly Val Pro Gly Val
            180                 185                 190
Gly Val Pro Gly Val Gly Val Pro Gly Val Gly Val Pro Gly Lys Gly
        195                 200                 205
Val Pro Gly Val Gly Val Pro Gly Val Gly Val Pro Gly Val Gly Val
210                 215                 220
Pro Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Gly Ala Gly Ser Gly
                245                 250                 255
Ala Gly Ala Gly Ser Gly Val Gly Val Pro Gly Val Gly Val Pro Gly
            260                 265                 270
Val Gly Val Pro Gly Val Gly Val Pro Gly Lys Gly Val Pro Gly Val
        275                 280                 285
Gly Val Pro Gly Val Gly Val Pro Gly Val Gly Val Pro Gly Ala Gly
        290                 295                 300
Ala Gly Ser Gly Ala Gly Ala Gly Ser Gly Ala Gly Ala Gly Ser Gly
305                 310                 315                 320
Ala Gly Ala Gly Ser Gly Ala Gly Ala Gly Ser Gly Ala Gly Ala Gly
                325                 330                 335
Ser Gly Val Gly Val Pro Gly Val Gly Val Pro Gly Val Gly Val Pro
            340                 345                 350
Gly Val Gly Val Pro Gly Lys Gly Val Pro Gly Val Gly Val Pro Gly
        355                 360                 365
Val Gly Val Pro Gly Val Gly Val Pro Gly Ala Gly Ala Gly Ser Gly
        370                 375                 380
Ala Gly Ala Gly Ser Gly Ala Gly Ala Gly Ser Gly Ala Gly Ala Gly
385                 390                 395                 400
Ser Gly Ala Gly Ala Gly Ser Gly Ala Gly Ala Gly Ser Gly Val Gly
                405                 410                 415
Val Pro Gly Val Gly Val Pro Gly Val Gly Val Pro Gly Val Gly Val
            420                 425                 430
Pro Gly Lys Gly Val Pro Gly Val Gly Val Pro Gly Val Gly Val Pro
        435                 440                 445
Gly Val Gly Val Pro Gly Ala Gly Ala Gly Ser Gly Ala Gly Ala Gly
        450                 455                 460
Ser Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
                485                 490                 495
Gly Val Pro Gly Val Gly Val Pro Gly Val Gly Val Pro Gly Lys Gly
            500                 505                 510
Val Pro Gly Val Gly Val Pro Gly Val Gly Val Pro Gly Val Gly Val
        515                 520                 525
Pro Gly Ala Gly Ala Gly Ser Gly Ala Gly Ala Gly Ser Gly Ala Gly
        530                 535                 540
Ala Gly Ser Gly Ala Gly Ala Gly Ser Gly Ala Gly Ala Gly Ser Gly
```

```
                          545                 550                 555                 560
               Ala Gly Ala Gly Ser Gly Val Gly Val Pro Gly Val Gly Val Pro Gly
                              565                 570                 575
               Val Gly Val Pro Gly Val Gly Val Pro Gly Lys Gly Val Pro Gly Val
                              580                 585                 590
               Gly Val Pro Gly Val Gly Val Pro Gly Val Gly Val Pro Gly Ala Gly
                              595                 600                 605
               Ala Gly Ser Gly Ala Gly Ala Gly Ser Gly Ala Gly Ala Gly Ser Gly
                              610                 615                 620
               Ala Gly Ala Gly Ser Gly Ala Gly Ala Gly Ser Gly Ala Gly Ala Gly
               625                 630                 635                 640
               Ser Gly Val Gly Val Pro Gly Val Gly Val Pro Gly Val Gly Val Pro
                                  645                 650                 655
               Gly Val Gly Val Pro Gly Lys Gly Val Pro Gly Val Gly Val Pro Gly
                              660                 665                 670
               Val Gly Val Pro Gly Val Gly Val Pro Gly Ala Gly Ala Gly Ser Gly
                              675                 680                 685
               Ala Gly Ala Gly Ser Gly Ala Gly Ala Gly Ser Gly Ala Gly Ala Gly
                              690                 695                 700
               Ser Gly Ala Gly Ala Gly Ser Gly Ala Gly Ala Gly Ser Gly Val Gly
               705                 710                 715                 720
               Val Pro Gly Val Gly Val Pro Gly Val Gly Val Pro Gly Val Gly Val
                              725                 730                 735
               Pro Gly Lys Gly Val Pro Gly Val Gly Val Pro Gly Val Gly Val Pro
                              740                 745                 750
               Gly Val Gly Val Pro Gly Ala Gly Ala Gly Ser Gly Ala Gly Ala Gly
                              755                 760                 765
               Ser Gly Ala Gly Ala Gly Ser Gly Ala Gly Ala Gly Ser Gly Ala Gly
                              770                 775                 780
               Ala Gly Ser Gly Ala Gly Ala Gly Ser Gly Val Gly Val Pro Gly Val
               785                 790                 795                 800
               Gly Val Pro Gly Val Gly Val Pro Gly Val Gly Val Pro Gly Lys Gly
                              805                 810                 815
               Val Pro Gly Val Gly Val Pro Gly Val Gly Val Pro Gly Val Gly Val
                              820                 825                 830
               Pro Gly Ala Gly Ala Gly Ser Gly Ala Gly Ala Gly Ser Gly Ala Gly
                              835                 840                 845
               Ala Gly Ser Gly Ala Gly Ala Gly Ser Gly Ala Gly Ala Gly Ser Gly
                              850                 855                 860
               Ala Gly Ala Gly Ser Gly Val Gly Val Pro Gly Val Gly Val Pro Gly
               865                 870                 875                 880
               Val Gly Val Pro Gly Val Gly Val Pro Gly Lys Gly Val Pro Gly Val
                              885                 890                 895
               Gly Val Pro Gly Val Gly Val Pro Gly Val Gly Val Pro Gly Ala Gly
                              900                 905                 910
               Ala Gly Ser Gly Ala Gly Ala Gly Ser Gly Ala Gly Ala Gly Ser Gly
                              915                 920                 925
               Ala Gly Ala Gly Ser Gly Ala Gly Ala Gly Ser Gly Ala Gly Ala Gly
                              930                 935                 940
               Ser Gly Val Gly Val Pro Gly Val Gly Val Pro Gly Val Gly Val Pro
               945                 950                 955                 960
               Gly Val Gly Val Pro Gly Lys Gly Val Pro Gly Val Gly Val Pro Gly
                              965                 970                 975
```

-continued

```
Val Gly Val Pro Gly Val Gly Val Pro Gly Ala Gly Ala Gly Ser Gly
            980                 985                 990

Ala Gly Ala Gly Ser Gly Ala Gly Ala Gly Ser Gly Ala Gly Ala Gly
        995                1000                1005

Ser Gly Ala Gly Ala Gly Ser Gly Ala Gly Ala Gly Ser Met Asp Pro
   1010                1015                1020

Gly Arg Tyr Gln Asp Leu Arg Ser His His His His His His
1025                1030                1035

<210> SEQ ID NO 31
<211> LENGTH: 965
<212> TYPE: PRT
<213> ORGANISM: Artificial Sequence
<220> FEATURE:
<223> OTHER INFORMATION: SELP 58

<400> SEQUENCE: 31

Met Asp Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Pro
             20                  25                  30

Met Gly Val Gly Val Pro Gly Val Gly Val Pro Gly Val Gly Val Pro
         35                  40                  45

Gly Val Gly Val Pro Gly Val Gly Val Pro Gly Val Gly Val Pro Gly
     50                  55                  60

Val Gly Val Pro Gly Val Gly Val Pro Gly Ala Gly Ala Gly Ser Gly
 65                  70                  75                  80

Ala Gly Ala Gly Ser Gly Ala Gly Ala Gly Ser Gly Ala Gly Ala Gly
                 85                  90                  95

Ser Gly Ala Gly Ala Gly Ser Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
   130                 135                 140

Ala Gly Ala Gly Ser Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
   210                 215                 220

Ser Gly Ala Gly Ala Gly Ser Gly Ala Gly Ala Gly Ser Gly Ala Gly
225                 230                 235                 240

Ala Gly Ser Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Ala Gly Ala Gly
        275                 280                 285

Ser Gly Ala Gly Ala Gly Ser Gly Ala Gly Ala Gly Ser Gly Ala Gly
   290                 295                 300

Ala Gly Ser Gly Ala Gly Ala Gly Ser Gly Val Gly Val Pro Gly Val
```

-continued

```
                305                 310                 315                 320
Gly Val Pro Gly Val Gly Val Pro Gly Val Gly Val Pro Gly Val Gly
                    325                 330                 335
Val Pro Gly Val Gly Val Pro Gly Val Gly Val Pro Gly Val Gly Val
                    340                 345                 350
Pro Gly Ala Gly Ala Gly Ser Gly Ala Gly Ala Gly Ser Gly Ala Gly
                    355                 360                 365
Ala Gly Ser Gly Ala Gly Ala Gly Ser Gly Ala Gly Ala Gly Ser Gly
                    370                 375                 380
Val Gly Val Pro Gly Val Gly Val Pro Gly Val Gly Val Pro Gly Val
385                 390                 395                 400
Gly Val Pro Gly Val Gly Val Pro Gly Val Gly Val Pro Gly Val Gly
                    405                 410                 415
Val Pro Gly Val Gly Val Pro Gly Ala Gly Ala Gly Ser Gly Ala Gly
                    420                 425                 430
Ala Gly Ser Gly Ala Gly Ala Gly Ser Gly Ala Gly Ala Gly Ser Gly
                    435                 440                 445
Ala Gly Ala Gly Ser Gly Val Gly Val Pro Gly Val Gly Val Pro Gly
                    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Ala Gly
                    485                 490                 495
Ala Gly Ser Gly Ala Gly Ala Gly Ser Gly Ala Gly Ala Gly Ser Gly
                    500                 505                 510
Ala Gly Ala Gly Ser Gly Ala Gly Ala Gly Ser Gly Val Gly Val Pro
                    515                 520                 525
Gly Val Gly Val Pro Gly Val Gly Val Pro Gly Val Gly Val Pro Gly
                    530                 535                 540
Val Gly Val Pro Gly Val Gly Val Pro Gly Val Gly Val Pro Gly Val
545                 550                 555                 560
Gly Val Pro Gly Ala Gly Ala Gly Ser Gly Ala Gly Ala Gly Ser Gly
                    565                 570                 575
Ala Gly Ala Gly Ser Gly Ala Gly Ala Gly Ser Gly Ala Gly Ala Gly
                    580                 585                 590
Ser Gly Val Gly Val Pro Gly Val Gly Val Pro Gly Val Gly Val Pro
                    595                 600                 605
Gly Val Gly Val Pro Gly Val Gly Val Pro Gly Val Gly Val Pro Gly
                    610                 615                 620
Val Gly Val Pro Gly Val Gly Val Pro Gly Ala Gly Ala Gly Ser Gly
625                 630                 635                 640
Ala Gly Ala Gly Ser Gly Ala Gly Ala Gly Ser Gly Ala Gly Ala Gly
                    645                 650                 655
Ser Gly Ala Gly Ala Gly Ser Gly Val Gly Val Pro Gly Val Gly Val
                    660                 665                 670
Pro Gly Val Gly Val Pro Gly Val Gly Val Pro Gly Val Gly Val Pro
                    675                 680                 685
Gly Val Gly Val Pro Gly Val Gly Val Pro Gly Val Gly Val Pro Gly
                    690                 695                 700
Ala Gly Ala Gly Ser Gly Ala Gly Ala Gly Ser Gly Ala Gly Ala Gly
705                 710                 715                 720
Ser Gly Ala Gly Ala Gly Ser Gly Ala Gly Ala Gly Ser Gly Val Gly
                    725                 730                 735
```

-continued

```
Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
            755                 760                 765

Gly Val Gly Val Pro Gly Ala Gly Ala Gly Ser Gly Ala Gly Ala Gly
            770                 775                 780

Ser Gly Ala Gly Ala Gly Ser Gly Ala Gly Ala Gly Ser Gly Ala Gly
785                 790                 795                 800

Ala Gly Ser Gly Val Gly Val Pro Gly Val Gly Val Pro Gly Val Gly
                805                 810                 815

Val Pro Gly Val Gly Val Pro Gly Val Gly Val Pro Gly Val Gly Val
            820                 825                 830

Pro Gly Val Gly Val Pro Gly Val Gly Val Pro Gly Ala Gly Ala Gly
            835                 840                 845

Ser Gly Ala Gly Ala Gly Ser Gly Ala Gly Ala Gly Ser Gly Ala Gly
850                 855                 860

Ala Gly Ser Gly Ala Gly Ala Gly Ser Gly Val Gly Val Pro Gly Val
865                 870                 875                 880

Gly Val Pro Gly Val Gly Val Pro Gly Val Gly Val Pro Gly Val Gly
                885                 890                 895

Val Pro Gly Val Gly Val Pro Gly Val Gly Val Pro Gly Val Gly Val
            900                 905                 910

Pro Gly Ala Gly Ala Gly Ser Gly Ala Gly Ala Gly Ser Gly Ala Gly
            915                 920                 925

Ala Gly Ser Gly Ala Gly Ala Gly Ser Gly Ala Gly Ala Gly Ser Met
            930                 935                 940

Asp Pro Gly Arg Tyr Gln Leu Ser Ala Gly Arg Tyr His Tyr Gln Leu
945                 950                 955                 960

Val Trp Cys Gln Lys
                965

<210> SEQ ID NO 32
<211> LENGTH: 1016
<212> TYPE: PRT
<213> ORGANISM: Unknown
<220> FEATURE:
<223> OTHER INFORMATION: SELP 47K-P4

<400> SEQUENCE: 32

Met Asp Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Ala Leu Ser
            35                  40                  45

Tyr Pro Gly Val Gly Val Pro Gly Val Gly Val Pro Gly Val Gly Val
        50                  55                  60

Pro Gly Val Gly Val Pro Gly Lys Gly Val Pro Gly Val Gly Val Pro
65                  70                  75                  80

Gly Val Gly Val Pro Gly Val Gly Val Pro Ala Leu Ser Tyr Pro Gly
                85                  90                  95

Ala Gly Ala Gly Ser Gly Ala Gly Ala Gly Ser Gly Ala Gly Ala Gly
            100                 105                 110

Ser Gly Ala Gly Ala Gly Ser Ala Leu Ser Tyr Pro Gly Val Gly Val
            115                 120                 125

Pro Gly Val Gly Val Pro Gly Val Gly Val Pro Gly Val Gly Val Pro
```

-continued

```
            130                 135                 140
Gly Lys Gly Val Pro Gly Val Gly Val Pro Gly Val Gly Val Pro Gly
145                 150                 155                 160

Val Gly Val Pro Ala Leu Ser Tyr Pro Gly Ala Gly Ala Gly Ser Gly
                165                 170                 175

Ala Gly Ala Gly Ser Gly Ala Gly Ser Gly Ala Gly Ala Gly Ser Gly
                180                 185                 190

Ser Ala Leu Ser Tyr Pro Gly Val Gly Val Pro Gly Val Gly Val Pro
                195                 200                 205

Gly Val Gly Val Pro Gly Val Gly Val Pro Gly Lys Gly Val Pro Gly
210                 215                 220

Val Gly Val Pro Gly Val Gly Val Pro Gly Val Gly Val Pro Ala Leu
225                 230                 235                 240

Ser Tyr Pro Gly Ala Gly Ala Gly Ser Gly Ala Gly Ala Gly Ser Gly
                245                 250                 255

Ala Gly Ala Gly Ser Gly Ala Gly Ser Ala Leu Ser Tyr Pro
                260                 265                 270

Gly Val Gly Val Pro Gly Val Gly Val Pro Gly Val Gly Val Pro Gly
                275                 280                 285

Val Gly Val Pro Gly Lys Gly Val Pro Gly Val Gly Val Pro Gly Val
                290                 295                 300

Gly Val Pro Gly Val Gly Val Pro Ala Leu Ser Tyr Pro Gly Ala Gly
305                 310                 315                 320

Ala Gly Ser Gly Ala Gly Ala Gly Ser Gly Ala Gly Ala Gly Ser Gly
                325                 330                 335

Ala Gly Ala Gly Ser Ala Leu Ser Tyr Pro Gly Val Gly Val Pro Gly
                340                 345                 350

Val Gly Val Pro Gly Val Gly Val Pro Gly Val Gly Val Pro Gly Lys
                355                 360                 365

Gly Val Pro Gly Val Gly Val Pro Gly Val Gly Val Pro Gly Val Gly
                370                 375                 380

Val Pro Ala Leu Ser Tyr Pro Gly Ala Gly Ala Gly Ser Gly Ala Gly
385                 390                 395                 400

Ala Gly Ser Gly Ala Gly Ala Gly Ser Gly Ala Gly Ala Gly Ser Ala
                405                 410                 415

Leu Ser Tyr Pro Gly Val Gly Val Pro Gly Val Gly Val Pro Gly Val
                420                 425                 430

Gly Val Pro Gly Val Gly Val Pro Gly Lys Gly Val Pro Gly Val Gly
                435                 440                 445

Val Pro Gly Val Gly Val Pro Gly Val Gly Val Pro Ala Leu Ser Tyr
450                 455                 460

Pro Gly Ala Gly Ala Gly Ser Gly Ala Gly Ala Gly Ser Gly Ala Gly
465                 470                 475                 480

Ala Gly Ser Gly Ala Gly Ala Gly Ser Ala Leu Ser Tyr Pro Gly Val
                485                 490                 495

Gly Val Pro Gly Val Gly Val Pro Gly Val Gly Val Pro Gly Val Gly
                500                 505                 510

Val Pro Gly Lys Gly Val Pro Gly Val Gly Val Pro Gly Val Gly Val
                515                 520                 525

Pro Gly Val Gly Val Pro Ala Leu Ser Tyr Pro Gly Ala Gly Ala Gly
                530                 535                 540

Ser Gly Ala Gly Ala Gly Ser Gly Ala Gly Ala Gly Ser Gly Ala Gly
545                 550                 555                 560
```

```
Ala Gly Ser Ala Leu Ser Tyr Pro Gly Val Gly Val Pro Gly Val Gly
                565                 570                 575
Val Pro Gly Val Gly Val Pro Gly Val Gly Val Pro Gly Lys Gly Val
            580                 585                 590
Pro Gly Val Gly Val Pro Gly Val Gly Val Pro Gly Val Gly Val Pro
        595                 600                 605
Ala Leu Ser Tyr Pro Gly Ala Gly Ala Gly Ser Gly Ala Gly Ala Gly
    610                 615                 620
Ser Gly Ala Gly Ala Gly Ser Gly Ala Gly Ala Gly Ser Ala Leu Ser
625                 630                 635                 640
Tyr Pro Gly Val Gly Val Pro Gly Val Gly Val Pro Gly Val Gly Val
                645                 650                 655
Pro Gly Val Gly Val Pro Gly Lys Gly Val Pro Gly Val Gly Val Pro
            660                 665                 670
Gly Val Gly Val Pro Gly Val Gly Val Pro Ala Leu Ser Tyr Pro Gly
        675                 680                 685
Ala Gly Ala Gly Ser Gly Ala Gly Ala Gly Ser Gly Ala Gly Ala Gly
    690                 695                 700
Ser Gly Ala Gly Ala Gly Ser Ala Leu Ser Tyr Pro Gly Val Gly Val
705                 710                 715                 720
Pro Gly Val Gly Val Pro Gly Val Gly Val Pro Gly Val Gly Val Pro
                725                 730                 735
Gly Lys Gly Val Pro Gly Val Gly Val Pro Gly Val Gly Val Pro Gly
            740                 745                 750
Val Gly Val Pro Ala Leu Ser Tyr Pro Gly Ala Gly Ala Gly Ser Gly
        755                 760                 765
Ala Gly Ala Gly Ser Gly Ala Gly Ala Gly Ser Gly Ala Gly Ala Gly
    770                 775                 780
Ser Ala Leu Ser Tyr Pro Gly Val Gly Val Pro Gly Val Gly Val Pro
785                 790                 795                 800
Gly Val Gly Val Pro Gly Val Gly Val Pro Gly Lys Gly Val Pro Gly
                805                 810                 815
Val Gly Val Pro Gly Val Gly Val Pro Gly Val Gly Val Pro Ala Leu
            820                 825                 830
Ser Tyr Pro Gly Ala Gly Ala Gly Ser Gly Ala Gly Ala Gly Ser Gly
        835                 840                 845
Ala Gly Ala Gly Ser Gly Ala Gly Ala Gly Ser Ala Leu Ser Tyr Pro
    850                 855                 860
Gly Val Gly Val Pro Gly Val Gly Val Pro Gly Val Gly Val Pro Gly
865                 870                 875                 880
Val Gly Val Pro Gly Lys Gly Val Pro Gly Val Gly Val Pro Gly Val
                885                 890                 895
Gly Val Pro Gly Val Gly Val Pro Ala Leu Ser Tyr Pro Gly Ala Gly
            900                 905                 910
Ala Gly Ser Gly Ala Gly Ala Gly Ser Gly Ala Gly Ala Gly Ser Gly
        915                 920                 925
Ala Gly Ala Gly Ser Ala Leu Ser Tyr Pro Gly Val Gly Val Pro Gly
    930                 935                 940
Val Gly Val Pro Gly Val Gly Val Pro Gly Val Gly Val Pro Gly Lys
945                 950                 955                 960
Gly Val Pro Gly Val Gly Val Pro Gly Val Gly Val Pro Gly Val Gly
                965                 970                 975
Val Pro Ala Leu Ser Tyr Pro Gly Ala Gly Ala Gly Ser Gly Ala Gly
            980                 985                 990
```

Ala Gly Ser Gly Ala Gly Ala Met Asp Pro Gly Arg Tyr Gln Asp Leu
    995                 1000                1005

Arg Ser His His His His His His
    1010            1015

<210> SEQ ID NO 33
<211> LENGTH: 3051
<212> TYPE: DNA
<213> ORGANISM: Unknown
<220> FEATURE:
<223> OTHER INFORMATION: DNA encoding SELP 47K-P4

<400> SEQUENCE: 33

| | | | | |
|---|---|---|---|---|
| atggatcccg | tcgttttaca | acgtcgtgac | tgggaaaacc | ctggcgttac ccaacttaat | 60 |
| cgccttgcag | cacatccccc | tttcgccagc | gatccgatgg | gagcgggtgc cggttctggt | 120 |
| gcaggcgcgg | gctctgcgct | gagctatccg | ggtgttggag | tgccaggtgt cggtgttccg | 180 |
| ggtgtaggcg | ttccgggagt | tggtgtacct | ggaaaaggtg | ttccggggt aggtgtgccg | 240 |
| ggcgttggag | taccaggtgt | aggcgtcccg | gcgctgagct | atccgggagc gggtgctggt | 300 |
| agcggcgcag | gcgcgggctc | tggagcgggt | gccggttctg | gtgcaggcgc gggctctgcg | 360 |
| ctgagctatc | cggtgttgg | agtgccaggt | gtcggtgttc | cgggtgtagg cgttccggga | 420 |
| gttggtgtac | ctggaaaagg | tgttccgggg | gtaggtgtgc | cggggttgg agtaccaggt | 480 |
| gtaggcgtcc | cggcgctgag | ctatccggga | gcgggtgctg | gtagcggcgc aggcgcgggc | 540 |
| tctggagcgg | gtgccggttc | tggtgcaggc | gcgggctctg | cgctgagcta tccgggtgtt | 600 |
| ggagtgccag | gtgtcggtgt | tccgggtgta | ggcgttccgg | gagttggtgt acctggaaaa | 660 |
| ggtgttccgg | gggtaggtgt | gccgggcgtt | ggagtaccag | gtgtaggcgt cccggcgctg | 720 |
| agctatccgg | gagcgggtgc | tggtagcggc | gcaggcgcgg | gctctggagc gggtgccggt | 780 |
| tctggtgcag | gcgcgggctc | tgcgctgagc | tatccgggtg | ttggagtgcc aggtgtcggt | 840 |
| gttccgggtg | taggcgttcc | gggagttggt | gtacctggaa | aaggtgttcc ggggtaggt | 900 |
| gtgccgggcg | ttggagtacc | aggtgtaggc | gtcccggcgc | tgagctatcc gggagcgggt | 960 |
| gctggtagcg | gcgcaggcgc | gggctctgga | gcgggtgccg | gttctggtgc aggcgcgggc | 1020 |
| tctgcgctga | gctatccggg | tgttggagtg | ccaggtgtcg | gtgttccggg tgtaggcgtt | 1080 |
| ccgggagttg | gtgtacctgg | aaaaggtgtt | ccggggtag | gtgtgccggg cgttggagta | 1140 |
| ccaggtgtag | gcgtcccggc | gctgagctat | ccgggagcgg | gtgctggtag cggcgcaggc | 1200 |
| gcgggctctg | gagcgggtgc | cggttctggt | gcaggcgcgg | gctctgcgct gagctatccg | 1260 |
| ggtgttggag | tgccaggtgt | cggtgttccg | ggtgtaggcg | ttccgggagt tggtgtacct | 1320 |
| ggaaaaggtg | ttccggggt | aggtgtgccg | ggcgttggag | taccaggtgt aggcgtcccg | 1380 |
| gcgctgagct | atccgggagc | gggtgctggt | agcggcgcag | gcgcgggctc tggagcgggt | 1440 |
| gccggttctg | gtgcaggcgc | gggctctgcg | ctgagctatc | cggtgttgg agtgccaggt | 1500 |
| gtcggtgttc | cgggtgtagg | cgttccggga | gttggtgtac | ctggaaaagg tgttccgggg | 1560 |
| gtaggtgtgc | cgggcgttgg | agtaccaggt | gtaggcgtcc | cggcgctgag ctatccggga | 1620 |
| gcgggtgctg | gtagcggcgc | aggcgcgggc | tctggagcgg | gtgccggttc tggtgcaggc | 1680 |
| gcgggctctg | cgctgagcta | tccgggtgtt | ggagtgccag | gtgtcggtgt tccgggtgta | 1740 |
| ggcgttccgg | gagttggtgt | acctggaaaa | ggtgttccgg | gggtaggtgt gccgggcgtt | 1800 |
| ggagtaccag | gtgtaggcgt | cccggcgctg | agctatccgg | gagcgggtgc tggtagcggc | 1860 |
| gcaggcgcgg | gctctggagc | gggtgccggt | tctggtgcag | gcgcgggctc tgcgctgagc | 1920 |

-continued

```
tatccgggtg ttggagtgcc aggtgtcggt gttccgggtg taggcgttcc gggagttggt    1980
gtacctggaa aaggtgttcc ggggtaggt gtgccgggcg ttggagtacc aggtgtaggc    2040
gtcccggcgc tgagctatcc gggagcgggt gctggtagcg cgcaggcgc gggctctgga    2100 gcgggtgccg gttctggtgc aggcgcgggc tctgcgctga gctatccggg tgttggagtg    2160
ccaggtgtcg gtgttccggg tgtaggcgtt ccgggagttg gtgtacctgg aaaaggtgtt    2220 ccggggtag gtgtgccggg cgttggagta ccaggtgtag gcgtcccggc gctgagctat    2280 ccggagcgg gtgctggtag cggcgcaggc gcgggctctg gagcgggtgc cggttctggt    2340
gcaggcgcgg gctctgcgct gagctatccg ggtgttggag tgccaggtgt cggtgttccg    2400
ggtgtaggcg ttccgggagt tggtgtacct ggaaaaggtg ttccgggggt aggtgtgccg    2460
ggcgttggag taccaggtgt aggcgtcccg gcgctgagct atccgggagc gggtgctggt    2520
agcggcgcag gcgcgggctc tggagcgggt gccggttctg gtgcaggcgc gggctctgcg    2580
ctgagctatc cggtgttgg agtgccaggt gtcggtgttc cggtgtagg cgttccggga    2640 gttggtgtac ctggaaaagg tgttccgggg taggtgtgc cgggcgttgg agtaccaggt    2700
gtaggcgtcc cggcgctgag ctatccggga gcgggtgctg gtagcggcgc aggcgcgggc    2760
tctggagcgg gtgccggttc tggtgcaggc gcgggctctg cgctgagcta tccgggtgtt    2820
ggagtgccag gtgtcggtgt tccgggtgta ggcgttccgg gagttggtgt acctggaaaa    2880
ggtgttccgg gggtaggtgt gccgggcgtt ggagtaccag gtgtaggcgt cccggcgctg    2940
agctatccgg gagcgggtgc tggtagcggc gcaggcgcgg gctctggagc gggtgccatg    3000
gacccgggtc gatatcagga tcttagatct catcaccatc accatcacta a             3051
```

<210> SEQ ID NO 34
<211> LENGTH: 1063
<212> TYPE: PRT
<213> ORGANISM: Unknown
<220> FEATURE:
<223> OTHER INFORMATION: silk-elastin repeat sequence protein copolymer

<400> SEQUENCE: 34

```
Met Asp Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Pro
             20                  25                  30

Met Gly Ala His Gly Pro Ala Gly Pro Lys Gly Ala His Gly Pro Ala
         35                  40                  45

Gly Pro Lys Gly Ala Gln Gly Pro Ala Gly Pro Gly Gly Ala Gln Gly
     50                  55                  60

Pro Ala Gly Pro Gly Gly Ala Gln Gly Pro Ala Gly Pro Gly Gly Ala
 65                  70                  75                  80

Gln Gly Pro Ala Gly Pro Gly Gly Ala Gln Gly Pro Ala Gly Pro Gly
                 85                  90                  95

Gly Ala Gln Gly Pro Ala Gly Pro Gly Gly Ala Gln Gly Pro Ala Gly
            100                 105                 110

Pro Gly Gly Ala Gln Gly Pro Ala Gly Pro Gly Gly Ala Gln Gly Pro
        115                 120                 125

Ala Gly Pro Gly Gly Ala Gln Gly Pro Ala Gly Pro Gly Gly Ala Gln
    130                 135                 140

Gly Pro Ala Gly Pro Gly Gly Ala Gln Gly Pro Ala Gly Pro Gly Gly
145                 150                 155                 160

Ala Gln Gly Pro Ala Gly Pro Gly Gly Ala Gln Gly Pro Ala Gly Pro
```

```
                165                 170                 175
Gly Gly Ala Gln Gly Pro Ala Gly Pro Gly Gly Ala Gln Gly Pro Ala
            180                 185                 190
Gly Pro Gly Gly Ala Gln Gly Pro Ala Gly Pro Gly Gly Ala Gln Gly
            195                 200                 205
Pro Ala Gly Pro Gly Gly Ala Gln Gly Pro Ala Gly Pro Gly Gly Ala
            210                 215                 220
Gln Gly Pro Ala Gly Pro Gly Gly Ala Gln Gly Pro Ala Gly Pro Gly
225                 230                 235                 240
Gly Ala Gln Gly Pro Ala Gly Pro Gly Gly Ala Gln Gly Pro Ala Gly
            245                 250                 255
Pro Gly Gly Ala Gln Gly Pro Ala Gly Pro Gly Gly Ala His Gly Pro
            260                 265                 270
Ala Gly Pro Lys Gly Ala His Gly Pro Ala Gly Pro Lys Gly Ala His
            275                 280                 285
Gly Pro Ala Gly Pro Lys Gly Ala His Gly Pro Ala Gly Pro Lys Gly
            290                 295                 300
Ala Gln Gly Pro Ala Gly Pro Gly Gly Ala Gln Gly Pro Ala Gly Pro
305                 310                 315                 320
Gly Gly Ala Gln Gly Pro Ala Gly Pro Gly Gly Ala Gln Gly Pro Ala
            325                 330                 335
Gly Pro Gly Gly Ala Gln Gly Pro Ala Gly Pro Gly Gly Ala Gln Gly
            340                 345                 350
Pro Ala Gly Pro Gly Gly Ala Gln Gly Pro Ala Gly Pro Gly Gly Ala
            355                 360                 365
Gln Gly Pro Ala Gly Pro Gly Gly Ala Gln Gly Pro Ala Gly Pro Gly
            370                 375                 380
Gly Ala Gln Gly Pro Ala Gly Pro Gly Gly Ala Gln Gly Pro Ala Gly
385                 390                 395                 400
Pro Gly Gly Ala Gln Gly Pro Ala Gly Pro Gly Gly Ala Gln Gly Pro
            405                 410                 415
Ala Gly Pro Gly Gly Ala Gln Gly Pro Ala Gly Pro Gly Gly Ala Gln
            420                 425                 430
Gly Pro Ala Gly Pro Gly Gly Ala Gln Gly Pro Ala Gly Pro Gly Gly
            435                 440                 445
Ala Gln Gly Pro Ala Gly Pro Gly Gly Ala Gln Gly Pro Ala Gly Pro
            450                 455                 460
Gly Gly Ala Gln Gly Pro Ala Gly Pro Gly Gly Ala Gln Gly Pro Ala
465                 470                 475                 480
Gly Pro Gly Gly Ala Gln Gly Pro Ala Gly Pro Gly Gly Ala Gln Gly
            485                 490                 495
Pro Ala Gly Pro Gly Gly Ala Gln Gly Pro Ala Gly Pro Gly Gly Ala
            500                 505                 510
Gln Gly Pro Ala Gly Pro Gly Gly Ala His Gly Pro Ala Gly Pro Lys
            515                 520                 525
Gly Ala His Gly Pro Ala Gly Pro Lys Gly Ala His Gly Pro Ala Gly
            530                 535                 540
Pro Lys Gly Ala His Gly Pro Ala Gly Pro Lys Gly Ala Gln Gly Pro
545                 550                 555                 560
Ala Gly Pro Gly Gly Ala Gln Gly Pro Ala Gly Pro Gly Gly Ala Gln
            565                 570                 575
Gly Pro Ala Gly Pro Gly Gly Ala Gln Gly Pro Ala Gly Pro Gly Gly
            580                 585                 590
```

```
Ala Gln Gly Pro Ala Gly Pro Gly Gly Ala Gln Gly Pro Ala Gly Pro
            595                 600                 605
Gly Gly Ala Gln Gly Pro Ala Gly Pro Gly Gly Ala Gln Gly Pro Ala
            610                 615                 620
Gly Pro Gly Gly Ala Gln Gly Pro Ala Gly Pro Gly Gly Ala Gln Gly
625                 630                 635                 640
Pro Ala Gly Pro Gly Gly Ala Gln Gly Pro Ala Gly Pro Gly Gly Ala
            645                 650                 655
Gln Gly Pro Ala Gly Pro Gly Gly Ala Gln Gly Pro Ala Gly Pro Gly
            660                 665                 670
Gly Ala Gln Gly Pro Ala Gly Pro Gly Gly Ala Gln Gly Pro Ala Gly
            675                 680                 685
Pro Gly Gly Ala Gln Gly Pro Ala Gly Pro Gly Gly Ala Gln Gly Pro
            690                 695                 700
Ala Gly Pro Gly Gly Ala Gln Gly Pro Ala Gly Pro Gly Gly Ala Gln
705                 710                 715                 720
Gly Pro Ala Gly Pro Gly Gly Ala Gln Gly Pro Ala Gly Pro Gly Gly
            725                 730                 735
Ala Gln Gly Pro Ala Gly Pro Gly Gly Ala Gln Gly Pro Ala Gly Pro
            740                 745                 750
Gly Gly Ala Gln Gly Pro Ala Gly Pro Gly Gly Ala Gln Gly Pro Ala
            755                 760                 765
Gly Pro Gly Gly Ala His Gly Pro Ala Gly Pro Lys Gly Ala His Gly
            770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
            805                 810                 815
Gly Ala Gln Gly Pro Ala Gly Pro Gly Gly Ala Gln Gly Pro Ala Gly
            820                 825                 830
Pro Gly Gly Ala Gln Gly Pro Ala Gly Pro Gly Gly Ala Gln Gly Pro
            835                 840                 845
Ala Gly Pro Gly Gly Ala Gln Gly Pro Ala Gly Pro Gly Gly Ala Gln
            850                 855                 860
Gly Pro Ala Gly Pro Gly Gly Ala Gln Gly Pro Ala Gly Pro Gly Gly
865                 870                 875                 880
Ala Gln Gly Pro Ala Gly Pro Gly Gly Ala Gln Gly Pro Ala Gly Pro
            885                 890                 895
Gly Gly Ala Gln Gly Pro Ala Gly Pro Gly Gly Ala Gln Gly Pro Ala
            900                 905                 910
Gly Pro Gly Gly Ala Gln Gly Pro Ala Gly Pro Gly Gly Ala Gln Gly
            915                 920                 925
Pro Ala Gly Pro Gly Gly Ala Gln Gly Pro Ala Gly Pro Gly Gly Ala
            930                 935                 940
Gln Gly Pro Ala Gly Pro Gly Gly Ala Gln Gly Pro Ala Gly Pro Gly
945                 950                 955                 960
Gly Ala Gln Gly Pro Ala Gly Pro Gly Gly Ala Gln Gly Pro Ala Gly
            965                 970                 975
Pro Gly Gly Ala Gln Gly Pro Ala Gly Pro Gly Gly Ala Gln Gly Pro
            980                 985                 990
Ala Gly Pro Gly Gly Ala Gln Gly Pro Ala Gly Pro Gly Gly Ala Gln
            995                 1000                1005
Gly Pro Ala Gly Pro Gly Gly Ala Gln Gly Pro Ala Gly Pro Gly Gly
            1010                1015                1020
```

```
Ala His Gly Pro Ala Gly Pro Lys Gly Ala His Gly Pro Ala Gly Pro
1025                1030                1035                1040

Lys Met Asp Pro Gly Arg Tyr Gln Leu Ser Ala Gly Arg Tyr His Tyr
                1045                1050                1055

Gln Leu Val Trp Cys Gln Lys
            1060

<210> SEQ ID NO 35
<211> LENGTH: 3024
<212> TYPE: DNA
<213> ORGANISM: Unknown
<220> FEATURE:
<223> OTHER INFORMATION: DNA encoding silk-elastin repeat sequence

<400> SEQUENCE: 35
ggcgcgcatg gcccggcggg cccgaaaggc gcgcatggcc cggcgggccc gaaaggcgcg      60
cagggcccgg cggcccggg cggcgcgcag ggcccggcgg gcccgggcgg cgcgcagggc     120
ccggcgggcc cggcggcgc gcagggcccg gcgggcccgg cgcgcgca gggcccggcg        180 ggcccgggcg gcgcgcaggg cccggcgggc cggcggcgg cgcagggccc ggcgggcccg      240
ggcggcgcgc agggcccggc gggcccgggc ggcgcgcagg gccggcggg cccggcggc       300 gcgcagggcc cggcgggccc ggcggcgcg cagggcccgg cgggcccggg cggcgcgcag      360
ggcccggcgg gcccggcgg cgcgcagggc cggcggcgg cccggcggc gcagggcccg        420 gcgggcccgg gcggcgcgca gggcccggcg ggcccgggcg gcgcgcaggg cccggcgggc     480 ccggcggcg cgcagggccc ggcgggcccg gcggcgcgc agggcccggc gggcccgggc       540
ggcgcgcagg gcccggcggg cccggcggc gcagggccc cggcgggccc gggcggcgcg       600
cagggcccgg cgggcccggg cggcgcgcag gccggcgg gccgggcgg cgcgcagggc        660 ccggcgggcc cggcggcgc gcagggcccg gcgggcccgg cggcgcgca tggcccggcg       720 ggcccgaaag gcgcgcatgg cccggcgggc cgaaaggcg cgcatggccc ggcgggcccg      780
aaaggcgcgc atggcccggc gggcccgaaa ggcgcgcagg gcccggcggg cccgggcggc     840
gcgcagggcc cggcgggccc gggcggcgcg cagggcccgg cggcccggg cggcgcgcag      900 ggcccggcgg gcccgggcgg cgcgcagggc ccggcgggcc cggcggcgc gcagggcccg      960 gcgggcccgg gcggcgcgca gggcccggcg ggcccgggcg gcgcgcaggg cccggcgggc    1020 ccggcggcg cgcagggccc ggcgggcccg gcggcgcgc agggcccggc gggcccgggc      1080
ggcgcgcagg gcccggcggg cccggcggc gcagggcccc cggcgggccc gggcggcgcg    1140
cagggcccgg cgggcccggg cggcgcgcag gccggcgg gccgggcgg cgcgcagggc       1200 ccggcgggcc cggcggcgc gcagggcccg gcgggcccgg cgcgcgca gggcccggcg       1260 ggcccgggcg gcgcgcaggg cccggcgggc cggcggcgg cgcagggccc ggcgggcccg     1320
ggcggcgcgc agggcccggc gggcccgggc ggcgcgcagg gccggcggg cccggcggc      1380 gcgcagggcc cggcgggccc gggcggcgcg catggcccgg cgggcccgaa aggcgcgcat    1440
ggcccggcgg gccggcgg cgcgcatggc ccggcgggcc cgaaaggcgc gcatggcccg      1500
gcgggcccga aaggcgcgca tggcccggcg ggcccgaaag gcgcgcatgg cccggcgggc    1560
ccgaaaggcg cgcagggccc ggcgggcccg gcggcgcg agggcccggc gggcccgggc      1620
ggcgcgcagg gcccggcggg cccgggcggc gcagggcccc cggcgggccc gggcggcgcg    1680
cagggcccgg cgggcccggg cggcgcgcag gccccggcgg gcccgggcgg cgcgcagggc    1740
ccggcgggcc cggcggcgc gcagggcccg gcgggcccgg gcggcgcgca gggcccggcg    1800
```

-continued

```
ggcccgggcg gcgcgcaggg cccggcgggc ccggcggcg cgcagggccc ggcgggcccg   1860
ggcggcgcgc agggcccggc gggcccgggc ggcgcgcagg gcccggcggg cccggcgggc   1920
gcgcagggcc cggcgggccc gggcggcgcg cagggcccgg cgggcccggg cggcgcgcag   1980
ggcccggcgg gcccggcgg cgcgcagggc ccggcgggcc cggcggcgc gcagggcccg   2040 gcgggcccgg gcggcgcgca gggcccggcg gcccgggcg gcgcgcaggg cccggcgggc   2100 ccggcggcg cgcagggccc ggcgggcccg ggcggcgcgc agggcccggc gggcccgggc   2160
ggcgcgcagg gcccggcggg cccggcggc gcgcagggcc ggcgggccc ggcggcgcg   2220 catggcccgg cgggcccgaa aggcgcgcat ggcccggcgg gccgaaaagg cgcgcatggc   2280
ccggcgggcc cgaaaggcgc gcatggcccg gcgggcccga aaggcgcgca gggcccggcg   2340
ggcccgggcg gcgcgcaggg cccggcgggc ccggcggcg cgcagggccc ggcgggcccg   2400
ggcggcgcgc agggcccggc gggcccgggc ggcgcgcagg gcccggcggg cccgggcggc   2460
gcgcagggcc cggcgggccc gggcggcgcg cagggcccgg cgggcccggg cggcgcgcag   2520
ggcccggcgg gcccggcgg cgcgcagggc ccggcgggcc cggcggcgc gcagggcccg   2580 gcgggcccgg gcggcgcgca gggcccggcg gcccgggcg gcgcgcaggg cccggcgggc   2640 ccggcggcg cgcagggccc ggcgggcccg ggcggcgcgc agggcccggc gggcccgggc   2700
ggcgcgcagg gcccggcggg cccggcggc gcgcagggcc ggcgggccc ggcggcgcg   2760 cagggcccgg cgggcccggg cggcgcgcag gccccggcgg gcccgggcgg cgcgcagggc   2820
ccggcgggcc cggcggcgc gcagggcccg gcgggcccgg gcggcgcgca gggcccggcg   2880
ggcccgggcg gcgcgcaggg cccggcgggc ccggcggcg cgcagggccc ggcgggcccg   2940
ggcggcgcgc agggcccggc gggcccgggc ggcgcgcatg gcccggcggg cccgaaaggc   3000
gcgcatggcc cggcgggccc gaaa                                       3024
```

<210> SEQ ID NO 36
<211> LENGTH: 5
<212> TYPE: PRT
<213> ORGANISM: Artificial Sequence
<220> FEATURE:
<223> OTHER INFORMATION: repeat sequence

<400> SEQUENCE: 36

Ala Leu Ser Tyr Pro
1               5

<210> SEQ ID NO 37
<211> LENGTH: 1080
<212> TYPE: PRT
<213> ORGANISM: Artificial Sequence
<220> FEATURE:
<223> OTHER INFORMATION: synthetic collagen-like peptide

<400> SEQUENCE: 37

Gly Ala His Gly Pro Ala Gly Pro Lys Gly Ala His Gly Pro Ala Gly
1               5                   10                  15

Pro Lys Gly Ala His Gly Pro Ala Gly Pro Lys Gly Ala His Gly Pro
                20                  25                  30

Ala Gly Pro Lys Gly Ala Gln Gly Pro Ala Gly Pro Gly Gly Ala Gln
            35                  40                  45

Gly Pro Ala Gly Pro Gly Gly Ala Gln Gly Pro Ala Gly Pro Gly Gly
        50                  55                  60

Ala Gln Gly Pro Ala Gly Pro Gly Gly Ala Gln Gly Pro Ala Gly Pro
65                  70                  75                  80

```
Gly Gly Ala Gln Gly Pro Ala Gly Pro Gly Ala Gln Gly Pro Ala
                85                  90                  95
Gly Pro Gly Gly Ala Gln Gly Pro Ala Gly Pro Gly Gly Ala Gln Gly
            100                 105                 110
Pro Ala Gly Pro Gly Gly Ala Gln Gly Pro Ala Gly Pro Gly Gly Ala
        115                 120                 125
Gln Gly Pro Ala Gly Pro Gly Gly Ala Gln Gly Pro Ala Gly Pro Gly
130                 135                 140
Gly Ala Gln Gly Pro Ala Gly Pro Gly Gly Ala Gln Gly Pro Ala Gly
145                 150                 155                 160
Pro Gly Gly Ala Gln Gly Pro Ala Gly Pro Gly Gly Ala Gln Gly Pro
            165                 170                 175
Ala Gly Pro Gly Gly Ala Gln Gly Pro Ala Gly Pro Gly Gly Ala Gln
        180                 185                 190
Gly Pro Ala Gly Pro Gly Gly Ala Gln Gly Pro Ala Gly Pro Gly Gly
    195                 200                 205
Ala Gln Gly Pro Ala Gly Pro Gly Gly Ala Gln Gly Pro Ala Gly Pro
210                 215                 220
Gly Gly Ala Gln Gly Pro Ala Gly Pro Gly Gly Ala Gln Gly Pro Ala
225                 230                 235                 240
Gly Pro Gly Gly Ala Gln Gly Pro Ala Gly Pro Gly Gly Ala His Gly
            245                 250                 255
Pro Ala Gly Pro Lys Gly Ala His Gly Pro Ala Gly Pro Lys Gly Ala
        260                 265                 270
His Gly Pro Ala Gly Pro Lys Gly Ala His Gly Pro Ala Gly Pro Lys
    275                 280                 285
Gly Ala His Gly Pro Ala Gly Pro Lys Gly Ala His Gly Pro Ala Gly
290                 295                 300
Pro Lys Gly Ala Gln Gly Pro Ala Gly Pro Gly Gly Ala Gln Gly Pro
305                 310                 315                 320
Ala Gly Pro Gly Gly Ala Gln Gly Pro Ala Gly Pro Gly Gly Ala Gln
            325                 330                 335
Gly Pro Ala Gly Pro Gly Gly Ala Gln Gly Pro Ala Gly Pro Gly Gly
        340                 345                 350
Ala Gln Gly Pro Ala Gly Pro Gly Gly Ala Gln Gly Pro Ala Gly Pro
    355                 360                 365
Gly Gly Ala Gln Gly Pro Ala Gly Pro Gly Gly Ala Gln Gly Pro Ala
370                 375                 380
Gly Pro Gly Gly Ala Gln Gly Pro Ala Gly Pro Gly Gly Ala Gln Gly
385                 390                 395                 400
Pro Ala Gly Pro Gly Gly Ala Gln Gly Pro Ala Gly Pro Gly Gly Ala
            405                 410                 415
Gln Gly Pro Ala Gly Pro Gly Gly Ala Gln Gly Pro Ala Gly Pro Gly
        420                 425                 430
Gly Ala Gln Gly Pro Ala Gly Pro Gly Gly Ala Gln Gly Pro Ala Gly
    435                 440                 445
Pro Gly Gly Ala Gln Gly Pro Ala Gly Pro Gly Gly Ala Gln Gly Pro
    450                 455                 460
Ala Gly Pro Gly Gly Ala Gln Gly Pro Ala Gly Pro Gly Gly Ala Gln
465                 470                 475                 480
Gly Pro Ala Gly Pro Gly Gly Ala Gln Gly Pro Ala Gly Pro Gly Gly
            485                 490                 495
Ala Gln Gly Pro Ala Gly Pro Gly Gly Ala Gln Gly Pro Ala Gly Pro
        500                 505                 510
```

```
Gly Gly Ala Gln Gly Pro Ala Gly Pro Gly Ala His Gly Pro Ala
        515                 520                 525
Gly Pro Lys Gly Ala His Gly Pro Ala Gly Pro Lys Gly Ala His Gly
        530                 535                 540
Pro Ala Gly Pro Lys Gly Ala His Gly Pro Ala Gly Pro Lys Gly Ala
545                 550                 555                 560
His Gly Pro Ala Gly Pro Lys Gly Ala His Gly Pro Ala Gly Pro Lys
                565                 570                 575
Gly Ala Gln Gly Pro Ala Gly Pro Gly Ala Gln Gly Pro Ala Gly
            580                 585                 590
Pro Gly Gly Ala Gln Gly Pro Ala Gly Pro Gly Ala Gln Gly Pro
        595                 600                 605
Ala Gly Pro Gly Gly Ala Gln Gly Pro Ala Gly Pro Gly Gly Ala Gln
        610                 615                 620
Gly Pro Ala Gly Pro Gly Gly Ala Gln Gly Pro Ala Gly Pro Gly Gly
625                 630                 635                 640
Ala Gln Gly Pro Ala Gly Pro Gly Gly Ala Gln Gly Pro Ala Gly Pro
                645                 650                 655
Gly Gly Ala Gln Gly Pro Ala Gly Pro Gly Gly Ala Gln Gly Pro Ala
            660                 665                 670
Gly Pro Gly Gly Ala Gln Gly Pro Ala Gly Pro Gly Gly Ala Gln Gly
        675                 680                 685
Pro Ala Gly Pro Gly Gly Ala Gln Gly Pro Ala Gly Pro Gly Gly Ala
        690                 695                 700
Gln Gly Pro Ala Gly Pro Gly Gly Ala Gln Gly Pro Ala Gly Pro Gly
705                 710                 715                 720
Gly Ala Gln Gly Pro Ala Gly Pro Gly Gly Ala Gln Gly Pro Ala Gly
                725                 730                 735
Pro Gly Gly Ala Gln Gly Pro Ala Gly Pro Gly Gly Ala Gln Gly Pro
            740                 745                 750
Ala Gly Pro Gly Gly Ala Gln Gly Pro Ala Gly Pro Gly Gly Ala Gln
        755                 760                 765
Gly Pro Ala Gly Pro Gly Gly Ala Gln Gly Pro Ala Gly Pro Gly Gly
        770                 775                 780
Ala Gln Gly Pro Ala Gly Pro Gly Gly Ala His Gly Pro Ala Gly Pro
785                 790                 795                 800
Lys Gly Ala His Gly Pro Ala Gly Pro Lys Gly Ala His Gly Pro Ala
                805                 810                 815
Gly Pro Lys Gly Ala His Gly Pro Ala Gly Pro Lys Gly Ala His Gly
            820                 825                 830
Pro Ala Gly Pro Lys Gly Ala His Gly Pro Ala Gly Pro Lys Gly Ala
        835                 840                 845
Gln Gly Pro Ala Gly Pro Gly Ala Gln Gly Pro Ala Gly Pro Gly
850                 855                 860
Gly Ala Gln Gly Pro Ala Gly Pro Gly Gly Ala Gln Gly Pro Ala Gly
865                 870                 875                 880
Pro Gly Gly Ala Gln Gly Pro Ala Gly Pro Gly Gly Ala Gln Gly Pro
                885                 890                 895
Ala Gly Pro Gly Gly Ala Gln Gly Pro Ala Gly Pro Gly Gly Ala Gln
            900                 905                 910
Gly Pro Ala Gly Pro Gly Gly Ala Gln Gly Pro Ala Gly Pro Gly Gly
        915                 920                 925
Ala Gln Gly Pro Ala Gly Pro Gly Gly Ala Gln Gly Pro Ala Gly Pro
```

-continued

```
                     930                 935                 940
Gly Gly Ala Gln Gly Pro Ala Gly Pro Gly Gly Ala Gln Gly Pro Ala
945                 950                 955                 960

Gly Pro Gly Gly Ala Gln Gly Pro Ala Gly Pro Gly Gly Ala Gln Gly
                965                 970                 975

Pro Ala Gly Pro Gly Gly Ala Gln Gly Pro Ala Gly Pro Gly Gly Ala
                980                 985                 990

Gln Gly Pro Ala Gly Pro Gly Gly Ala Gln Gly Pro Ala Gly Pro Gly
            995                1000                1005

Gly Ala Gln Gly Pro Ala Gly Pro Gly Gly Ala Gln Gly Pro Ala Gly
        1010                1015                1020

Pro Gly Gly Ala Gln Gly Pro Ala Gly Pro Gly Gly Ala Gln Gly Pro
1025                1030                1035                1040

Ala Gly Pro Gly Gly Ala Gln Gly Pro Ala Gly Pro Gly Gly Ala Gln
                1045                1050                1055

Gly Pro Ala Gly Pro Gly Gly Ala His Gly Pro Ala Gly Pro Lys Gly
                1060                1065                1070

Ala His Gly Pro Ala Gly Pro Lys
            1075                1080
```

What is claimed is:

1. A method for protecting skin from environmental damage comprising the steps of a) providing skin to be exposed to environmental damage; b) providing a composition comprising a repeat sequence protein polymer, wherein said repeat sequence protein polymer comprises SEQ ID NO. 19 and wherein said repeat sequence protein polymer provides a cosmetic benefit; and c) applying said composition to said skin.

2. The method of claim 1, wherein said environmental damage comprises damage due to exposure to radiation.

3. The method of claim 2, wherein said radiation comprises ultraviolet light.

4. The method of claim 1, wherein said environmental damage comprises damage due to exposure to chemicals or free radicals.

* * * * *